(12) United States Patent
Lu et al.

(10) Patent No.: US 9,719,090 B2
(45) Date of Patent: Aug. 1, 2017

(54) METHODS OF TRANS-DIFFERENTIATING A TERMINALLY DIFFERENTIATED TARGET CELL TO A NEURON

(71) Applicant: The Board of Trustees of the Leland Stanford Junior University, Stanford, CA (US)

(72) Inventors: Bingwei Lu, Stanford, CA (US); Stephan Gehrke, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/654,998

(22) PCT Filed: Dec. 20, 2013

(86) PCT No.: PCT/US2013/077215
§ 371 (c)(1),
(2) Date: Jun. 23, 2015

(87) PCT Pub. No.: WO2014/105751
PCT Pub. Date: Jul. 3, 2014

(65) Prior Publication Data
US 2015/0344878 A1 Dec. 3, 2015

Related U.S. Application Data

(60) Provisional application No. 61/747,138, filed on Dec. 28, 2012.

(51) Int. Cl.
| | |
|---|---|
| *C12N 5/00* | (2006.01) |
| *C12N 15/113* | (2010.01) |
| *A61K 31/7105* | (2006.01) |
| *C12N 5/0793* | (2010.01) |
| *A61K 45/06* | (2006.01) |
| *A61K 35/30* | (2015.01) |
| *A61K 31/13* | (2006.01) |
| *A61K 31/198* | (2006.01) |
| *A61K 31/713* | (2006.01) |

(52) U.S. Cl.
CPC ............ *C12N 15/113* (2013.01); *A61K 31/13* (2013.01); *A61K 31/198* (2013.01); *A61K 31/713* (2013.01); *A61K 31/7105* (2013.01); *A61K 35/30* (2013.01); *A61K 45/06* (2013.01); *C12N 5/0619* (2013.01); *C12N 2310/14* (2013.01); *C12N 2320/30* (2013.01); *C12N 2501/60* (2013.01); *C12N 2501/998* (2013.01); *C12N 2503/02* (2013.01); *C12N 2506/1307* (2013.01)

(58) Field of Classification Search
CPC .......................... C12N 5/0619; C12N 15/113
See application file for complete search history.

(56) References Cited

U.S. PATENT DOCUMENTS

| | | |
|---|---|---|
| 2002/0049176 A1 | 4/2002 | Anderson et al. |
| 2005/0261217 A1 | 11/2005 | Dobie et al. |
| 2011/0159592 A1 | 6/2011 | You et al. |

OTHER PUBLICATIONS

Printout from Google search "differentiate definition".google.Com/search?q=differentiate+definition&sourceid=7&rls=com. pp. 1-2, Jun. 21, 2016.*
D'Souza, Arginine et al., Arginine/Serine-rich Protein Interaction Domain-dependent Modulation of a Tau Exon 10 Splicing Enhancer, The Journal of Biological Chemistry, Feb. 3, 2006, vol. 281, No. 5, pp. 2460-2469.
Garcia-Rodriquez et al., Puf3p, a Pumilio family RNA binding protein, localizes to mitochondria and reulates mitochondrial biogenesis and motility in budding yeast, The Journal of Cell Biology, Jan. 15, 2007, vol. 176, No. 2, pp. 197-207.
Schwartz, Catherine, Derivation, Enrichment, and Characterization of Dopaminergic Neurons from Pluripotent Stem Cells, Thesis for Doctoral Degree, Department of Medical Biochemistry and Biophysics, Karolinska Institute, Stockholm, Sweden, 2010.
Swistowski et al., Efficient Generation of Functional Dopaminergic Neurons from Human Induced Pluripotent Stem Cells Under Defined Conditions, Stem Cells, Oct. 1, 2010, vol. 28, pp. 1893-1904.
Valentine, et al., Hereditary Early-Onset Parkinsons Disease Caused by Mutations in PINK1, Science May 21, 2004, vol. 304, pp. 1158-1160.
Yin et al., Ventral Mesencephalon-Enriched Genes That Regulate the Development of Dopaminergic Neurons in Vivo, the Journal of Neuroscience, Apr. 22, 2009, vol. 29, pp. 5170-5182.

* cited by examiner

*Primary Examiner* — Marcia S Noble
(74) *Attorney, Agent, or Firm* — Bret E. Field; Bozicevic, Field & Francis LLP

(57) ABSTRACT

Methods and compositions are provided for the treatment of a mitochondrial disease in an individual with the mitochondrial disease. Aspects of the methods include administering an inhibitor of a Pumilio-like protein and/or an inhibitor of a serine/arginine-rich family of pre-mRNA splicing factor (SR) protein to a subject. Also provided are methods, compositions, systems and kits for transdifferentiating target cells to neurons, which find use in producing neurons for the development of new therapies, for experimental evaluation, as a source of lineage- and cell-specific products, and the like, for example, for use in treating human disorders of the CNS.

11 Claims, 21 Drawing Sheets
(1 of 21 Drawing Sheet(s) Filed in Color)

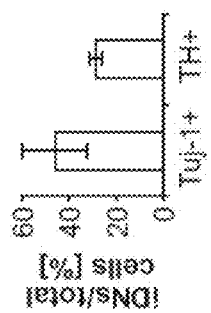
FIG. 1d
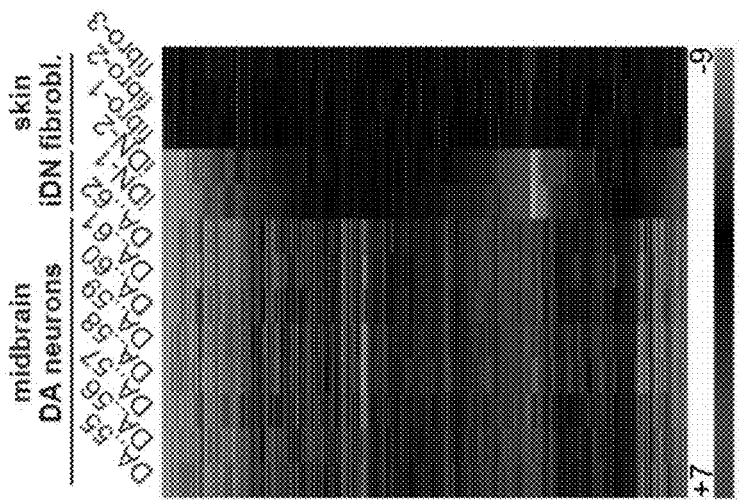
FIG. 1g
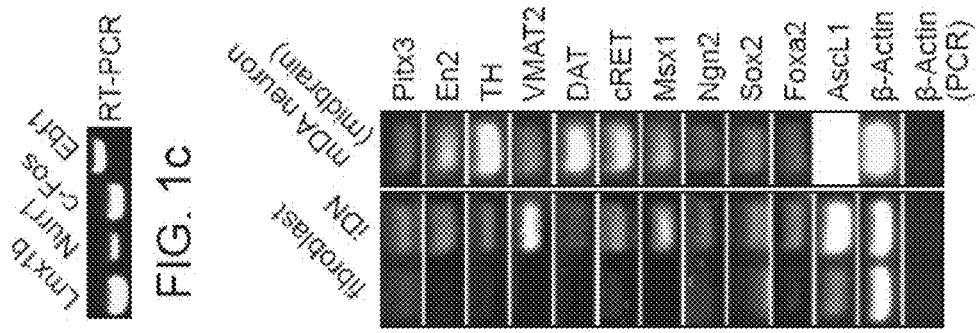
FIG. 1c
FIG. 1f
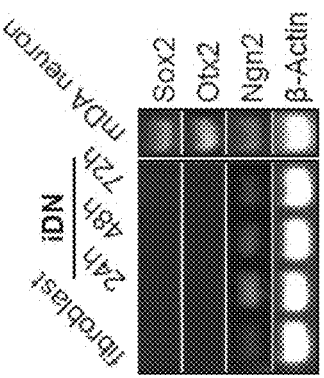
FIG. 1e

METHODS OF TRANS-DIFFERENTIATING A TERMINALLY DIFFERENTIATED TARGET CELL TO A NEURON

CROSS REFERENCE TO RELATED APPLICATIONS

This application is a 371 Application of PCT International Patent Application Serial No. PCTUS2013/077215, filed Dec. 20, 2015, which claims priority to the filing date of the U.S. Provisional Application Ser. No. 61/747,138 filed Dec. 28, 2012; the full disclosure of which is herein incorporated by reference.

FIELD OF THE INVENTION

Provided herein are compositions and method for the treatment of mitochondrial diseases in a subject.

Also provided herein are compositions and methods for differentiating cells, for example, somatic cells, to neurons.

BACKGROUND

Mitochondrial dysfunction can result in a host of debilitating mitochondrial diseases or disorders characterized by poor growth, loss of muscle coordination, muscle weakness, visual problems, hearing problems, learning disabilities, heart disease, liver disease, kidney disease, gastrointestinal disorders, respiratory disorders, neurological problems, autonomic dysfunction, and/or dementia. In many instances, these mitochondrial diseases are caused by acquired or inherited mutations in mitochondrial DNA or in nuclear genes that code for mitochondrial components or for cellular components that act as quality control checkpoints of mitochondrial function. For example, the mitochondrial disease Parkinson's disease (PD) is a common neurodegenerative movement disorder affecting 1% of the population above the age of 60 that has be linked to acquired or spontaneous mutations in mitochondrial genes or nuclear genes relevant to mitochondrial function. PD is characterized by the preferential loss and degeneration of dopaminergic neurons of the substantia nigra (SN) pars compacta and formation of Lewy bodies. PD patients exhibit resting tremor, bradykinesia, muscle rigidity and postural instability.

Although research is ongoing, treatment options are currently limited; vitamins are frequently prescribed, though the evidence for their effectiveness is limited. Rescuing dysfunctional mitochondria provides one approach for treating mitochondrial diseases or disorders. Membrane penetrating antioxidants and pyruvate are two examples of treatment options for improving mitochondrial dysfunction. As such, there is a need for the development of new therapeutic agents and methods for the treatment of mitochondrial disease.

Neurons produced by the transdifferentiation of pluripotent stem cells or non-neuronal somatic cells may be useful for the development of therapeutics, for experimental evaluation, for transplantation, as a source of lineage- and cell-specific products, and the like, to treat human disorders, for example neurodegenerative disorders such as Parkinson's Disease. Somatic cells generated from induced pluripotent stem cells, however, can undergo cell proliferation that can, in turn, cause new genomic alterations. Methods of somatic cell to somatic cell transdifferentiation often involve an intermediate step of de-differentiation to a pluripotent cell stage before further differentiation to the somatic cell type of interest. Such reprogramming steps can be slow and inefficient, requiring significant time and manipulation in vivo. Accordingly, there is a need for a method to transdifferentiate a non-neuronal cell directly to post-mitotic neuron.

SUMMARY

Methods and compositions are provided for the treatment of a mitochondrial disease in an individual with the mitochondrial disease. Aspects of the methods include administering an inhibitor of a Pumilio-like protein and/or an inhibitor of a serine/arginine-rich family of pre-mRNA splicing factor (SR) protein to a subject. Also provided are methods, compositions, systems and kits for transdifferentiating target cells to neurons, which find use in producing neurons for the development of new therapies, for experimental evaluation, as a source of lineage- and cell-specific products, and the like, for example, for use in treating human disorders of the CNS.

In some aspects, a method is provided for treatment of a mitochondrial disease in a subject having a mitochondrial disease comprising administering a therapeutically effective amount of an inhibitor of a Pumilio-like protein and/or an inhibitor of an SR protein to the subject. In some embodiments, the inhibitor of the Pumilio-like protein is an inhibitor of Pumilio-1 (PUM1). In some embodiments, the inhibitor of the SR protein is an inhibitor of Splicing Factor 2 (SF2). In certain embodiments, the inhibitor of a Pumilio-like protein and/or the inhibitor of an SR protein is an antibody or fragment thereof. In other embodiments, the inhibitor is a nucleic acid. In yet other embodiments, the inhibitor is a small molecule.

In certain embodiments, the mitochondrial disease is Parkinson's Disease (PD). In some such embodiments, the PD is a familial form of PD, e.g. a PTEN-induced putative kinase 1 (PINK-1)-associated form of PD, a Parkin-associated form of PD, an LRRK2-associated form of PD, an alpha-Synuclein (SNCA)-associated form of PD, a ubiquitin carboxy-terminal hydrolase L1 (UCHL1)-associated form of PD, a parkinson protein 7 (PARK7, DJ-1) associated form of PD, an ATP13A2-associated form of PD, a phospholipase A2, group VI (PLA2G6)-associated form of PD, a DnaJ (Hsp40) homolog, subfamily C, member 6 (DNAJC6, PARK19)-associated form of PD; a eukaryotic translation initiation factor 4 gamma, 1 (EIF4G1, PARK18)-associated form of PD; a F-box protein 7 (FBXO7)-associated form of PD; a GRB10 interacting GYF protein 2 (GIGYF2)-associated form of PD; a HtrA serine peptidase 2 (HTRA2)-associated form of PD; a synaptojanin 1 (SYNJ1)-associated form of PD; and a vacuolar protein sorting 35 homolog (VPS35)-associated form of PD. In other such embodiments, the PD is a sporadic form of Parkinson's Disease, for example, it is associated with a sporadic mutation in one of the aforementioned genes. In certain such embodiments, the subject inhibitor(s) is administered to the midbrain and/or putamen of the subject.

In some embodiments, the method further comprises the step of administering a therapeutically effective amount of one or more additional therapeutics for the treatment of the mitochondrial disease. In some embodiments, the additional therapeutic is selected from the group consisting of levodopa, a dopamine agonist, a MAO-B inhibitor, amantadine, and an anticholinergic, a Parkin agonist, a PINK1 agonist, an 4E-BP1 agonist, a Drp1 agonist, an Atg1 agonist, a Miro antagonist, a TauS2A agonist, a Rbf1 agonist, a Dp antagonist, an E2f1 antagonist, a Polo-like kinase 2 antagonist and a Notch agonist. In some embodiments, the subject inhibitor(s) are provided at the same time as the additional therapeutic. In some embodiments, the subject inhibitor(s) are provided before the additional therapeutic. In some embodiments, the subject inhibitor(s) are provide after the additional therapeutic.

In another aspect, provided herein is a pharmaceutical composition comprising an inhibitor of a Pumilio-like protein and/or an inhibitor of an SR protein and a pharmaceutically acceptable carrier, which finds use in the treatment of a mitochondrial disease.

In another aspect, provided herein is a method of differentiating target cells to neurons comprising the step of introducing a LIM homeobox transcription factor (Lmx) agent, a nuclear receptor subfamily 4 (NR4) agent, a c-Fos agent, and an Early B Cell Factor (EBF) agent into the target cell under conditions suitable to cause the target cell to differentiate into a neuron. In some embodiments the Lmx agent is an Lmx1 b agent. In some embodiments, the NR4 agent is a Nurr1 agent. In some embodiments, the EBF agent is an EBF1 agent. In certain embodiments, the target cell is a non-neuronal somatic cell. In particular embodiments, the somatic cell is a human somatic cell. In certain embodiments, the target cell is a fibroblast. In one embodiment, the neuron is a dopaminergic neuron. In some embodiments, the LIM homeobox transcription factor agent is an Lmx polypeptide, the Nuclear receptor subfamily 4 agent is a NR4 polypeptide, the c-Fos agent is a c-Fos polypeptide, and the Early B Cell Factor (EBF) agent is an EBF polypeptide. In some embodiments, the LIM homeobox transcription factor agent is a nucleic acid, i.e. a DNA or an RNA encoding a Lmx protein, the Nuclear receptor subfamily 4 agent is a nucleic acid, i.e. a DNA or an RNA, encoding a NR4 protein, the c-Fos agent is a nucleic acid, i.e. a DNA or an RNA, encoding c-Fos, and the Early B Cell Factor (EBF) agent is a nucleic acid, i.e. a DNA or an RNA, encoding an EBF protein. In certain embodiments, the nucleic acids encoding Lmx, Nurr, c-Fos, and EBF proteins are introduced into the somatic cell by transduction. In certain embodiments, the nucleic acids are introduced into the non-neuronal somatic cell by a virus. In some embodiments, the method finds use in preparing cells for the screening of candidate agents for the treatment of diseases of the nervous system, for example, mitochondrial diseases affecting neurons of the CNS.

In another aspect, provided herein is a neuron differentiation (ND) cocktail comprising a LIM homeobox transcription factor (Lmx) agent, a nuclear receptor agent, a c-Fos agent, and an Early B Cell Factor (EBF) agent. In certain embodiments, the Lmx agent is an Lmx1 b agent, the nuclear receptor agent is a Nurr1 agent, and the EBF agent is an EBF1 agent. In some embodiments, the cocktail finds use in preparing cells for the screening of candidate agents for the treatment of diseases of the nervous system, for example, mitochondrial diseases affecting neurons of the CNS.

In yet another aspect, provided herein is a method for screening candidate agents for the treatment of mitochondrial disease of the CNS, e.g. Parkinson's Disease (PD), Neuropathy ataxia retinitis pigmentosa (NARP), Leber's hereditary optic neuropathy (LHON), comprising the steps of contacting a neuron with a candidate agent, wherein the neuron is derived from a cell of a subject with a mitochondrial disease; and assessing a parameter of the neuron. In certain embodiments, the cell is a non-neuronal somatic cell, e.g. a fibroblast. In some embodiments, the parameter is the amount of mitochondrial-bound RNA in the neuron cell; the distribution and morphology of mitochondria in the processes of the neuron; or the ATP levels of the neurons. In certain embodiments, the non-neuronal somatic cell is from a subject with a mutation in a gene associated with Parkinson's disease. In some such embodiments, the gene is PTEN-induced putative kinase 1 (PINK-1); Parkin (RBR E3 ubiquitin protein ligase, PARK2); leucine-rich repeat kinase 2 (LRRK2); alpha-Synuclein (SNCA, PARK4); ubiquitin carboxy-terminal hydrolase L1 (UCHL1); parkinson protein 7 (PARK7, DJ-1); ATPase type 13A2 (ATP13A2); phospholipase A2, group VI (PLA2G6); DnaJ (Hsp40) homolog, subfamily C, member 6 (DNAJC6, PARK19); eukaryotic translation initiation factor 4 gamma, 1 (EIF4G1, PARK18); F-box protein 7 (FBXO7); GRB10 interacting GYF protein 2 (GIGYF2); HtrA serine peptidase 2 (HTRA2); synaptojanin 1 (SYNJ1); or vacuolar protein sorting 35 homolog (VPS35).

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to scale. On the contrary, the dimensions of the various features are arbitrarily expanded or reduced for clarity. Included in the drawings are the following Figures.

FIG. 1a-1g shows the transdifferentiation of human adult fibroblasts into dopaminergic neurons (DA neurons). FIG. 1a is an immunohistochemical analysis of the induced dopaminergic neurons (iDNs) using anti-Tuj-1 and anti-TH. Phase contrast and immunofluorescence images are shown. FIG. 1b shows immunohistochemistry of the induced dopaminergic neurons using antibodies against TH, VMAT2, DAT, and PSD-95. FIG. 1c is an RT-PCR analysis of introduced transcription factor expression in human fibroblast three days after induction. FIG. 1d is a quantification of Tuj-1 positive and TH/Tuj-1 double positive induced DA neurons (iDNs) as percentage of all cells. The data represents four independent experiments. FIG. 1e shows an RT-PCR analysis of neuronal progenitor markers Sox2 and Otx2 in fibroblasts 24, 48, and 72 hours after the induction of transfected transcription factors. Mouse midbrain DA neurons (mDA neurons) serve as positive control. β-Actin serves as internal control. FIG. 1f shows an RT-PCR analysis of DA neurons marker gene expression in adult human fibroblast, induced human DA neurons (iDNs), and mouse midbrain DA neurons (P27). β-Actin was included as internal control and also as a control for genomic DNA contamination (PCR). FIG. 1g shows a comparative analysis of the mRNA profiles of induced DA neurons (iDNs), adult human midbrain dopaminergic neurons (mDA), and adult human fibroblasts (fibro). Red indicates up-regulated and green indicates down-regulated genes. mRNA profiles of fibroblasts have been averaged and used as standard.

FIG. 2a is a comparison of mitochondrial morphology in fibroblast and converted iDNs from control and PD subject carrying a PINK1(G309D) mutation. Cells were co-infected with lenti-virus expressing the mitochondrial reporter mito-GFP. FIG. 2b is a quantification of the number of mitochondrial aggregates larger than 90 μm in diameter in the periphery of fibroblasts and iDNs. For each sample at least 4 cells were analyzed (*P<0.05). FIG. 2c is an analysis of signal intensity ratios of mito-GFP versus Tuj-1 in neurites of iDNs in the proximal to distal direction relative to the soma. FIG. 2d is a quantification of ATP levels in control and PINK1(G309D) fibroblasts and iDNs (*P<0.05, n=4). FIG. 2e is a comparison of ATP production in fibroblasts and iDNs from a control subject. ATP levels were normalized with the levels of the mitochondrial protein Mfn2 or the cytoplasmic protein Tubulin. Protein levels were determined by Western blot (WB) analysis. FIG. 2f is a WB analysis of control (WT) and PINK1(G309D) mutant fibroblasts and iDNs with the indicated antibodies. Neuronal β-III Tubulin and β-I+II Tubulin serve as controls. FIG. 2g is an RT-PCR analysis showing comparable expression between control and PINK1(G309D) iDNs of the indicated RCC mRNAs.

FIG. 4a-4c is an $m^7$-GTP sepharose chromatography of TIC showing association of exogenous (FIG. 4a) and endogenous (FIG. 4b) PINK1 with the TIC and compromised binding of PINK1(G309D) with the TIC (FIG. 4c). RNase A treatment of extract dramatically reduced the association of PINK1 with the TIC (FIG. 4a). eIF4E serves as a positive control for TIC. FIG. 4d shows PINK1 directly bound to RCC mRNAs as detected by CLIP assay. IgG serves as Endogenous control. Note that PINK1 bound to RCC mRNAs but not Mfn2 mRNA. FIG. 4e and FIG. 4f show overexpression of PINK1(WT) promoted (FIG. 4e), whereas PINK1(G309D) overexpression (FIG. 4e) or knockdown of endogenous PINK1 (FIG. 4f) reduced the mitochondria-association of complex-V5a and complex-I 30 kD mRNAs in HEK293T cells. Input indicates the amount of mRNA in the extract used for the purification of intact mitochondria. β-actin serves as control. FIG. 4g shows mitochondria-association of RCC mRNAs in control and PINK1(G309D) fibroblasts and iDNs. FIGS. 4h and i show that knockdown of Pum-1 in HEK293T cells led to increased recruitment of RCC mRNAs to mitochondria (FIG. 4h), and increased RCC (complex-I 30 kD) protein expression (FIG. 4i). Actin serves as control (FIG. 4i). FIGS. 4j and k show CLIP assays showing competition between PINK1 and Pum-1 in direct binding to RCC (complex-I 30 kD) mRNA. Overexpression of PINK1 in HEK293T cells led to reduced RCC mRNA binding by endogenous Pum-1, whereas PINK1(G309D) overexpression promoted Pum-1 binding to RCC mRNA (FIG. 4j). Overexpressed PINK1 itself showed strong binding to RCC mRNA, whereas PINK1(G309D) showed little binding. Knockdown of PINK1 had similar effect as PINK1 (G309D) overexpression (FIG. 4k).

FIG. 7a shows a Western blot analysis of purified intact mitochondria assessing the presence of a mitochondrial marker (complex II 70 kD) and the endoplasmic reticulum (ER) specific marker recognizing KDEL (Lys-Asp-Glu-Leu)-containing proteins. Shown are the input and the purified mitochondrial fractions. Note that the intact mitochondrial fraction did not contain ER proteins. FIG. 7b shows a Western blot analysis performed on aliquots of purified intact mitochondrial fractions. HEK293T cells were transfected with PINK1(WT) or PINK1(G309D) expression plasmids. GFP serves as a control. Western blot analyses for Complex II 70 kD and ribosomal protein Rps6 are shown.

FIGS. 9a and b show that Pum-1 RNAi restored Complex-I 30 kD protein level (FIG. 9a), and ATP synthesis (FIG. 9b) in PINK1(G309D) iDNs. Control RNAi did not show such effect. Actin serves as control. Data were collected from three independent experiments (P<0.05). FIG. 9c shows reduced mitochondria-association of RCC mRNAs in head tissues of PINK1$^{B9}$ null mutant flies. RT-PCR was performed with mRNAs extracted from purified mitochondria (mito), the cytoplasm (cyto), and nucleus (nucl) fractions. Rps49 mRNA serves as control for the RT-PCR, and Actin for Western blot analysis. Complex-IV (sub.1), which is mitochondrial-encoded, serves as control for purified mitochondria. FIG. 9d shows RT-PCR and WB analyses showing reduced localization and translation of mitochondria-associated RCC mRNAs in PINK1$^{B9}$ null mutant thoracic muscle. FIG. 9e are RT-PCR and WB analyses, showing rescue of the reduced localization and translation of mitochondria-associated mRNAs in the thoracic muscles of dPINK1 RNAi flies after RNAi-mediated knockdown of Pum, SF2, or DAP-160, whereas Tim8 RNAi has the opposite effects.

FIG. 13a-13c shows that MHC-Gal4-driven Pum RNAi restored wing posture (FIG. 13a), jumping activity (FIG. 13b), and ATP synthesis (FIG. 13c) in PINK1$^{B9}$ null mutant flies raised and aged for 15 days (FIG. 13a), or 3 days (FIG. 13b, 13c) at 29° C. Tim8 RNAi had opposite effects. FIG. 13d shows that TH-Gal4-driven Pum RNAi rescued the loss of DNs in the PPL1 cluster of 15-day old PINK1$^{B9}$ null mutant flies raised and aged at 29° C. All data were collected from three independent experiments for each genotype ($P<0.05$). FIG. 13e shows that MHC-Gal4-driven Pum RNAi in the PINK1 RNAi background suppressed the abnormal mitochondria morphology in thoracic muscle tissue (scale bar: 30 μm). Tim8 RNAi exacerbated PINK1 RNAi induced mitochondrial phenotype. FIG. 13f shows that TH-Gal4-driven Pum RNAi suppressed the formation of mitochondrial aggregates in DNs within the PPL1 cluster of PINK1$^{B9}$ null mutant background, whereas Tim8 RNAi enhanced such phenotypes. Mitochondria were labelled with mito-GFP. DNs were immunostained with anti-tyrosine hydroxylase (TH).

DETAILED DESCRIPTION

Figures 1A, 1B:
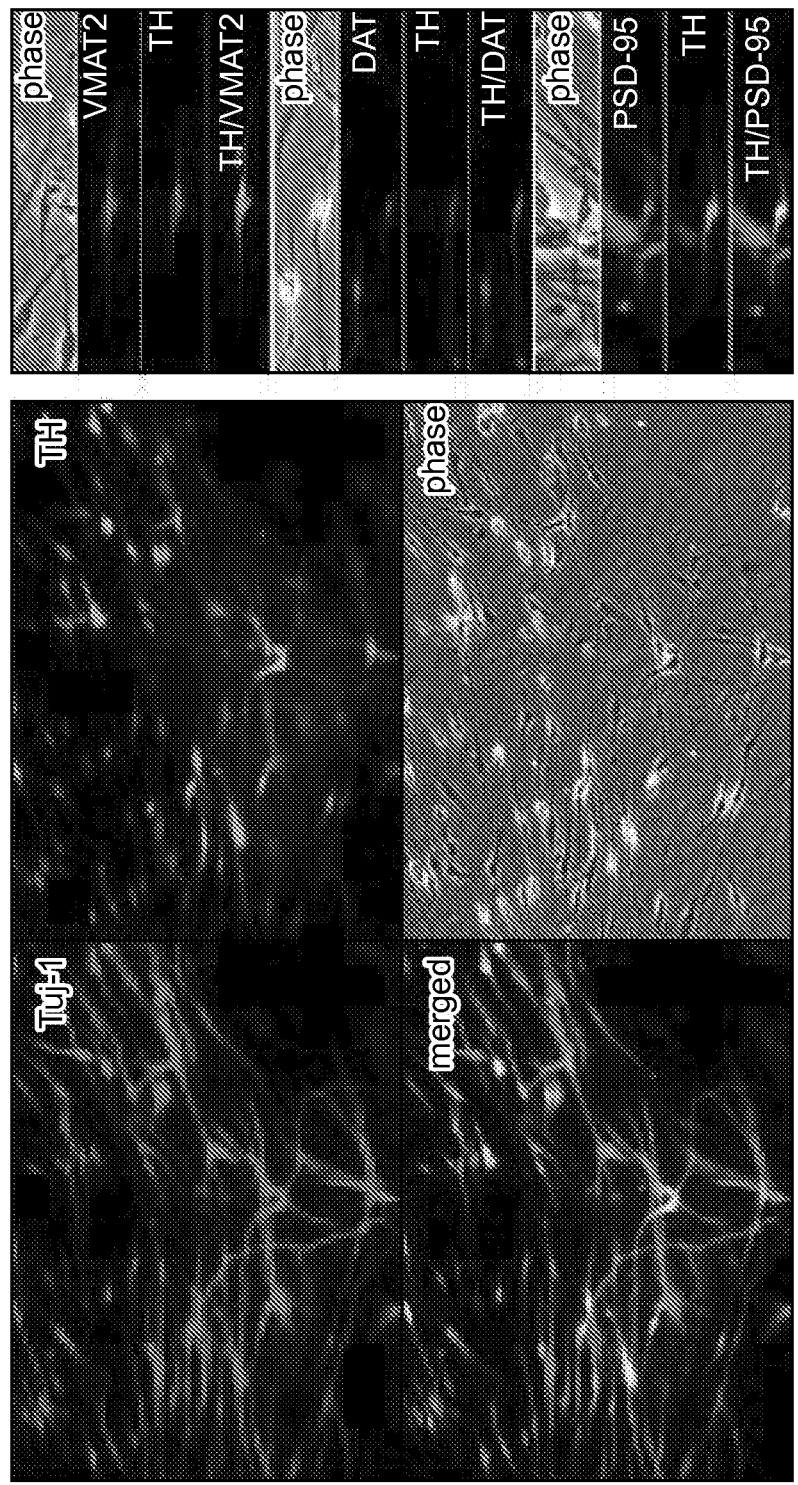

Methods and compositions are provided for the treatment of a mitochondrial disease in an individual with the mitochondrial disease. Aspects of the methods include administering an inhibitor of a Pumilio-like protein and/or an inhibitor of a serine/arginine-rich family of pre-mRNA splicing factor (SR) protein to a subject. Also provided are methods, compositions, systems and kits for transdifferentiating target cells to neurons, which find use in producing neurons for the development of new therapies, for experimental evaluation, as a source of lineage- and cell-specific products, and the like, for example, for use in treating human disorders of the CNS. These and other objects, advantages, and features of the invention will become apparent to those persons skilled in the art upon reading the details of the compositions and methods as more fully described below.

The methods and compositions described herein are not limited to a particular method or composition described and, as such, may vary. It is also to be understood that the terminology used herein is for the purpose of describing particular embodiments only, and is not intended to be limiting, since the scope of the methods and compositions will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed, subject to any specifically excluded limit in the stated range. Where the stated range includes one or both of the limits, ranges excluding either or both of those included limits are also included.

Unless defined otherwise, all technical and scientific terms used herein have the same meaning as commonly understood by one of ordinary skill in the art. Although any methods and materials similar or equivalent to those described herein can be used in the practice or testing of the present methods and compositions, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods and compositions. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present methods and compositions are not entitled to antedate such publication by virtue of prior invention. Further, the dates of publication provided may be different from the actual publication dates which may need to be independently confirmed.

DEFINITIONS

As used herein, the term "Pumilio-like protein" refers to a member of the Pumilio family of RNA binding proteins that includes, but is not limited to, Pumilio homolog 1 (PUM1) (e.g., also "PUMH," "PUMH1," and "PUML1," the sequence for which can be found at GenBank Accession Nos. NM_001020658.1 and NP_001018494.1) and Pumilio homolog 2 (PUM2) (e.g., GenBank Accession Nos. NM_015317.1 and NP_056132.1). Pumilio-like proteins contain a sequence-specific RNA binding domain composed of eight repeats and N- and C-terminal flanking regions, and can serve as a translational regulator of specific mRNAs by binding to their 3' untranslated regions. Pumilio-like proteins specifically bind to sequences in the 3'UTR of target mRNAs, inhibiting translation and destabilizing the mRNA by de-adenylation.

As used herein, the term "SR protein" refers to a member of the serine/arginine (SR)-rich family of pre-mRNA splicing factors that includes, but is not limited to Splicing Factor 2 ("SF2", also known as "SRSF1," "splicing factor, arginine/serine-rich 1," "serine/arginine rich splicing factor 1," "SR splicing factor 1," "ASF-1," and "alternative-splicing factor 1", e.g., GenBank Accession No. NM_001109552); serine/arginine-rich splicing factor 5 (SF5, or SRSF5, e.g. GenBank Accession No. NM_001039465.1 and NP_001034554.1); and serine/arginine-rich splicing factor 9 ("SF9," or "SRSF9", e.g. GenBank Accession No. NM_003769.2 and NP_003760.1). SR proteins comprise two functional modules: an arginine-serine rich region (RS domain), where the bulk of ASF/SF2 regulation takes place, and two RNA recognition motifs (RRMs), through which ASF/SF2 interacts with RNA and other splicing factors. For example, SF2 is an essential sequence specific splicing factor involved in pre-mRNA splicing and is involved in regulating and selecting splice sites in eukaryotic mRNAs. SF2 contains two functional modules: a serine-arginine rich region (SR domain) and two RNA recognition motifs (RRMs).

As used herein, the terms "LIM homeobox transcription factor" and "Lmx" refer to any member of a family of proteins that function as transcriptional regulators and carry the LIM domain, a cysteine-rich zinc-binding domain. LIM homeobox transcription factors include, but are not limited to, LIM homeobox transcription factor 1, alpha (Lmx1a), encoded by the Lmx1a gene (e.g., GenBank Accession Nos. NM_001174146.1 and NP_001167540.1 (human) and NM_0033652.2 (mouse)); and LIM homeobox transcription factor 1, beta (Lmx1 b), encoded by the Lmx1b gene (e.g., GenBank Accession Nos. NM_001174146.1 and NP_001167617.1 (human) and NM_010725.2 (mouse)).

As used herein, the terms "nuclear receptor subfamily 4" and "NR4" refers to a member of a family of nerve growth factor-induced clone B group orphan receptors that function as DNA-binding transcription factors. NR4 family members include, but are not limited to NGFI-B (NR4A1) (GenBank Accession Nos. NM_001202233.1 and NP_00189162.1), Nurr1 (NR4A2) (GenBank Accession Nos. NM_006186.3 and NP_006177.1); and NOR1 (NR4A3) (GenBank Accession Nos. NM_006981.3 and NP_008912.2).

As used herein, the terms "Early B Cell Factor," "COE," and "Collier/Olf-1/EBF," refer to a family of zinc-binding transcription factors that can form homo- and heterodimers that bind to DNA at specific sites that include the sequence 5'-ATTCCCNNGGGAATT-3'. Members of the EBF family of transcription factors include EBF1 (e.g., GenBank Accession Nos. NM_024007.3 and NP_076870.1 (human) and NM_007897.2 (mouse)), EBF2 (e.g., GenBank Accession Nos. NM_0022659.3 and NP_073150.2 (human) and NM_010095 (mouse)), and EBF3 (e.g., GenBank Accession Nos. NM_001005463.2 and NP_001005463.1 (human) and NM_010096 (mouse)).

As used herein, "c-Fos" refers to a protein encoded by the FOS gene (e.g., GenBank Accession Nos. NM_005252.3 (human) and NM_010234.2 (mouse)), and belonging to the immediate early gene family of transcription factors. c-Fos may comprise a leucine-zipper DNA binding domain, and a transactivation domain at the C-terminus.

As used herein, the terms "induced neuronal cell," "iN cell," "induced neuron," and "iN" encompass cells of the neuronal lineage that arise from a non-neuronal cell by the methods of transdifferentiation described herein. Induced neuronal cells may express markers specific for cells of the neuronal lineage, e.g., Tau, Tuj1, MAP2, NeuN, and the like, and may have characteristics of functional neurons, that is, they may be able to be depolarized, i.e. propagate an action potential, and they may be able to make and maintain synapses with other neurons. In particular embodiments, the induced neuronal cell is an induced dopaminergic neuron. Induced dopaminergic neurons may express one or more dopaminergic neuron markers such as, but not limited to, Pitx3, En2, TH, VMAT2, DAT cRET, Msx1, Ngn2, Sox2, Foxa2, MASH1 (Ascl1) and the like, and may have characteristics of functional dopaminergic neurons, that is, they may be able to be depolarized, i.e. propagate an action potential, and they may be able to make and maintain synapses with other neurons.

As used herein, the terms "differentiation," and "differentiating" refer to a process whereby a target cell (e.g., a somatic cell or a pluripotent cell) is transformed into an induced cell (e.g., a cell different than the target cell). As used herein, the terms "transdifferentiation," and "transdifferentiating" refer to a process whereby a target cell (e.g., a somatic cell) is transformed into an induced cell (e.g., a somatic cell different than the target cell), without undergoing an intermediate pluripotent state or progenitor cell type.

As used herein, the term "target cell" refers to a cell that is contacted with one or more neuron differentiation (ND) factors or a neuron differentiation (ND) system to promote differentiation to an induced somatic cell (e.g., an induced neuron). A target cell can be a somatic cell or a pluripotent cell. In some embodiments, the target cell is a somatic cell, i.e. a "target somatic cell." In particular embodiments, the target cell is a non-neuronal somatic cell, i.e. a "target non-neuronal somatic cell." In other embodiments, the target cell is a pluripotent cell, i.e. a "target pluripotent cell."

As used herein, the terms "neuron differentiation factors" and "ND factors" refer to one or more, i.e. a cocktail, of biologically active factors that act on a target cell (e.g., a somatic cell or pluripotent cell) to promote the differentiation, e.g., conversion of the target cell into an induced neuron. In certain embodiments described herein, the neuron differentiation factors are neuron transdifferentiation factors.

As used herein, the terms "neuron transdifferentiation factors" and "NT factors" refer to one or more, i.e. a cocktail, of biologically active factors that act on a target somatic cell (e.g., mature somatic cell) to promote the transdifferentiation, i.e. direct conversion, of the target cell into an induced neuron. In certain embodiments described herein, the neuron transdifferentiation factors are dopaminergic transdifferentiation factors that act on a non-dopaminergic neuron to more promote transdifferentiation into an induced dopaminergic neuron.

As used herein, the term "neuron differentiation system" and "ND system" refer to reagents and culture conditions that promote the differentiation of target cells (e.g., somatic and non-somatic cells) into induced neurons. An ND system comprises one or more neuron differentiation factors (e.g., a neuron differentiation cocktail). An ND system may also optionally comprise other agents that promote the survival of the induced neurons. In some embodiments described herein, the neuron differentiation system is a dopaminergic neuron differentiation system.

As used herein, the term "neuron transdifferentiation system" and "NT system" refer to reagents and culture conditions that promote the transdifferentiation of mature somatic cells into induced neurons. An NT system comprises one or more neuron transdifferentiation factors (e.g., a neuron transdifferentiation cocktail). An NT system may also optionally comprise other agents that promote the survival of the induced neurons. An NT system does not require induced pluripotent stem cell reprogramming factors as they are known in the art, e.g., Oct 3/4, Sox2, KLF4, Myc, Nanog, or Lin28; or culture conditions developed in the art for culturing pluripotent stem cells, e.g., culture in hanging droplets. In some embodiments described herein, the neuron transdifferentiation system is a dopaminergic neuron transdifferentiation system.

As used herein, the term "mitochondrial disease" refers to any disease or disorder caused by dysfunctional mitochondria including, but not limited to, diseases that are related to dysfunction in mitochondrial biogenesis and homeostasis. Examples of mitochondrial diseases include, but are not limited to, mitochondrial myopathies, e.g., chronic progressive external ophthalmoplegia (CPEO), Kearns Sayre syndrome (KSS), or Myoclonus epilepsy ragged-red fibers (MERRF); Leigh's syndrome (subacute sclerosing encephalopathy); Myoneurogenic gastrointestinal encephalopathy (MNGIE); Diabetes mellitus and deafness (DAD); mitochondrial encephalomyopathy, lactic acidosis and stroke-like episodes (MELAS); or a mitochondrial neuropathy, e.g., Parkinson's Disease (PD), Neuropathy ataxia retinitis pigmentosa (NARP), or Leber's hereditary optic neuropathy (LHON).

The terms "treatment", "treating" and the like are used herein to generally mean obtaining a desired pharmacologic and/or physiological effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired, particularly humans.

Compositions and Methods for Treatment of Mitochondrial Diseases

Provided herein are compositions and methods for the treatment of mitochondrial diseases. By a "mitochondrial disease", it is meant a disease or disorder caused by dysfunctional mitochondria. By mitochondria it is meant the organelles that generate energy for the cell by converting the energy of food molecules into the ATP that powers most cell functions. Mitochondrial diseases are often caused by mutations in mitochondrial or nuclear DNA that encode proteins that affect mitochondrial biogenesis and function. The subclass of these diseases that have neuromuscular disease symptoms are often referred to as mitochondrial myopathies.

As disclosed herein, it is shown that PINK1 and Parkin, two proteins that are linked with Parkinson's Disease, can regulate the localization and translation of mitochondria-bound mRNAs important for mitochondrial biogenesis. See Example 2. Furthermore, it has been shown that defects in localization and translation of mitochondria-bound mRNAs associated with PINK1 mutations, including respiratory chain complex (RCC) mRNAs, can be rescued by inhibition of Pumilio-like proteins (e.g., Pumilio-1 (PUM1)) and/or of SR proteins (e.g. Splicing Factor 2 (SF2)). Therefore, without being bound by any particular theory of operation, it is believed that inhibitors of Pumilio-like proteins and inhibitors of SR proteins can be used in the treatment of mitochondrial diseases including, for example, Parkinson's Disease, e.g. by enhancing mitochondrial respiration and ATP production. In further describing aspects of the invention, the following description focuses on the mitochondrial neuropathy Parkinson's Disease. However, the subject methods and the reagents, devices and kits thereof also find use in the treatment of other mitochondrial diseases as well, as described herein and as known in the art.

Inhibitors of Pumilio-Like Proteins and of SR Proteins

Provided herein are inhibitors of Pumilio-like proteins and inhibitors of SR proteins. As used herein, an "inhibitor" refers to an agent that antagonizes, inhibits, suppresses or negatively regulates the activity of a protein, in this instance, a Pumilio-like protein or an SR protein. As discussed above, Pumilio-like proteins are proteins in the Pumilio family of RNA binding proteins, and SR proteins are member of the serine/arginine (SR)-rich family of pre-mRNA splicing factors. In some embodiments, the Pumilio-like protein inhibitor is an inhibitor of PUM1. In some embodiments, the Pumilio-like protein inhibitor is an inhibitor of PUM2. In some embodiments, the SR protein inhibitor is an inhibitor of SF2. In some embodiments, the SR protein inhibitor is an inhibitor of SF5. In some embodiments, the SR protein inhibitor is an inhibitor of SF9.

Inhibitors of Pumilio-like proteins and inhibitors of SR proteins (referred to interchangeably herein as "the subject inhibitor" or "the subject inhibitors") may inhibit the activity of their target protein (i.e. the Pumilio-like protein or SR protein, respectively) by a variety of different mechanisms. For example, in some embodiments, the subject inhibitor reduces expression of the target gene, e.g. reducing the production of Pumilio-like RNA or protein, or SR RNA or protein, respectively. In other embodiments, the inhibitor reduces the function of the target gene, e.g. by binding to target protein and interfering with the ability of the target protein to bind or act. In other embodiments, the inhibitor modulates the function of a protein upstream of the target protein, e.g. inhibiting a protein that activates the target protein, or activating a protein that inhibits the target protein.

For example, an inhibitor of a Pumilio-like protein may interfere with the expression, i.e. production of RNA or protein, from the Pumilio-like gene, e.g. the PUM1 or PUM2 gene. As another example, the inhibitor may interfere with the ability of the Pumilio-like protein to bind and/or de-adenylate RNA. As a third example, an inhibitor of the Pumilio-like protein may interfere with the ability of proteins upstream of the Pumilio-like protein, e.g. NLK1, to phosphorylate the Pumilio-like protein. Inhibitors of Pumilio-like proteins may inhibit the level or biological activity of Pumilio-like proteins by 20% or more, for example, 30% or more, 40% or more, or 50% or more, sometimes 60% or more, 70% or more, or 80% or more, e.g. 90%, 95%, or 100%, relative to an untreated control not contracted with the Pumilio-like protein inhibitor. An inhibitor of a Pumilio-like protein may be validated as such and its effective amount determined by any convenient method in the art for detecting protein levels and protein activity of the inhibited Pumilio-like protein. For example, levels and/or the phosphorylation state of a Pumilio-like protein in the presence versus absence of inhibitor may be detected, for example by Western blotting with PUM1- or PUM2-specific antibodies or PUM1phospho- or PUM2phospho-specific antibodies. As another example, the ability of the Pumilio-like protein to bind to target RNA in the presence versus absence of inhibitor may be assessed, for example by RNA-binding protein immunoprecipitation-chip (RIP-chip) (see, e.g. Morris et al. Mol Cell Biol 28(12): 4093-4103 (2008)). As a third example, the ability of the Pumilio-like protein to destabilize and/or repress the translation of target RNAs in the presence versus absence of inhibitor may be assessed, for example, by detecting the mRNA or protein levels of targets such as, e.g., Cks2, CyclinB1, CyclinE2, PCNA, SLBPF, or RCC proteins by RT-qPCT in proliferating cells such as HeLa cells after the addition of actinomycin D (see, e.g. Morris et al., supra). As a fourth example, the association of target RNAs such as RCC mRNA with mitochondria may be assessed, for example by methods described in the working examples below. Representative inhibitors include, but are not limited to: nucleic acid inhibitors (e.g., PUM1 or PUM2-specific antisense oligonucleotides and RNAi agents, described herein); PUM1 or PUM2-specific antibodies; small molecule compounds; and the like.

Similarly, an inhibitor of an SR protein may interfere with the expression, i.e. production of RNA or protein, from an SR gene. As another example, an inhibitor of an SR protein may interfere with the ability of the SR protein to bind RNA or splice bound RNA. As a third example, an inhibitor of the SR protein may interfere with the ability of kinases upstream of the SR protein, e.g. SRPK1 (Hagopian et al., J. Mol. Biol. 382(4): 894-909 (2008)) or topoisomerase I (Pilch et al., Cancer Res. 61(18): 6876-84(2001)), to phosphorylate and activate the SR protein, or may promote the activity of phosphatases, upstream of the SR protein, e.g. protein phosphatase PP1, to dephosphorylate and deactivate the SR protein. Inhibitors of SR proteins inhibit the expression level or biological activity of the SR protein, e.g. to splice a known target sequence, by 20% or more, for example, 30% or more, 40% or more, or 50% or more, sometimes 60% or more, 70% or more, or 80% or more, e.g. 90%, 95%, or 100% relative to an untreated control not contracted with the SR protein inhibitor. An inhibitor of a SR protein may be validated as such and its effective amount determined by any convenient method in the art for detecting protein levels and protein activity of the inhibited SR protein. For example, levels and/or the phosphorylation state of the SR protein in may be assessed, for example by Western blotting (see, e.g., Ma et al. J. MOl. Biol. 203(3):386-404 (2010)). The ability of the SR protein to splice a target sequence in the presence versus absence of inhibitor may be assessed, for example by in vitro splicing assays (see, e.g., the assays of Bakkour et al. to detect splicing of HIV pre-mRNA by SF2 in the presence of IDC16 inhibitor in Bakkour et al. PLOS Pathogens 3(10)12:1530-39 (2007)) or by RT-PCR of the product. Representative inhibitors include, but are not limited to: nucleic acid inhibitors, e.g., SR protein-specific antisense oligonucleotides and RNAi agents; SR protein-specific antibodies; small molecule compounds, e.g., the glycosylated indolocarbazole derivative NB-506 (Pilch et al., supra), the indole derivatives compounds IDC16 (of Bakkour et al., supra), and IDC13 and IDC78 (Keriel et al. PLoS One. 2009; 4(2):e4533), etc.; and the like.

For example, in certain embodiments, the inhibitor of the Pumilio-like protein is a nucleic acid inhibitor (e.g., antisense inhibitor, shRNA agent, siRNA agent, etc.) acts on the Pumilio-like gene or mRNA to inhibit the amount of the target Pumilio-like protein produced, thereby reducing the amount of Pumilio-like protein activity in the targeted cells, where the target cell may be present in vitro or in vivo. Likewise, in certain embodiments, the inhibitor of the SR protein is a nucleic acid inhibitor (e.g., antisense inhibitor, shRNA agent, siRNA agent, etc.) acts on the SR gene or mRNA to inhibit the amount of the target SR protein produced, thereby reducing the amount of SR protein activity in the targeted cells, where the target cell may be present in vitro or in vivo. By "reducing the amount of" is meant that the level or quantity of the target Pumilio-like protein or SR protein in the target cell is reduced by at least about 2-fold, usually by at least about 5-fold, e.g., 10-fold, 15-fold, 20-fold, 50-fold, 100-fold or more, as compared to a control, i.e., an identical target cell not treated according to the subject methods. Changes in amounts of target protein may be readily detected by a number of methods known in the art, e.g., Western blotting, ELISA, etc.

For example, in certain embodiments, the subject inhibitor is an antisense inhibitor, e.g. a PUM1- or PUM2-specific antisense inhibitor, or, e.g., a SF2- or SF5- or SF9-specific antisense inhibitor. An antisense inhibitor may be antisense oligonucleotides (ODN), particularly synthetic ODN having chemical modifications from native nucleic acids, or nucleic acid constructs that express such antisense molecules as RNA. The antisense sequence is complementary to the targeted mRNA, and inhibits its translation into protein. One or a combination of antisense molecules may be administered, where a combination may comprise multiple different sequences.

Antisense molecules may be produced by expression of all or a part of the subject inhibitor RNA in an appropriate vector, where the transcriptional initiation is oriented such that an antisense strand is produced as an RNA molecule. Alternatively, the antisense molecule may be a synthetic oligonucleotide. Antisense oligonucleotides will generally be at least about 7, usually at least about 12, more usually at least about 20 nucleotides in length, and not more than about 25, usually not more than about 23-22 nucleotides in length, where the length is governed by efficiency of inhibition, specificity, including absence of cross-reactivity, and the like. In certain embodiments the inhibitor of PUM1 is an antisense oligonucleotide that is 7, 8, 9, 10, 11, 12, 13, 14, 15, 16, 17, 18, 19, 20, 21, 22, 23, 24, 25, 26, 27, 28, 29, 30, 31, 32, 33, 34, or 35 nucleotides in length. In certain embodiments the inhibitor of SF2 is an antisense oligonucleotide that is 7, 8, 9, 10, 11, 12, 13, 14, 15, 16, 17, 18, 19, 20, 21, 22, 23, 24, 25, 26, 27, 28, 29, 30, 31, 32, 33, 34, or 35 nucleotides in length.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications that alter the chemistry of the backbone, sugars or heterocyclic bases have been described in the literature.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The alpha.-anomer of deoxyribose may be used, where the base is inverted with respect to the natural.beta.-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Anti-sense molecules of interest also include antagomir RNAs, e.g., as described by Krutzfeldt et al., supra., herein specifically incorporated by reference. Small interfering double-stranded RNAs (siRNAs) engineered with certain 'drug-like' properties such as chemical modifications for stability and cholesterol conjugation for delivery have been shown to achieve therapeutic silencing of an endogenous gene in vivo. To develop a pharmacological approach for silencing mRNAs in vivo, chemically modified, cholesterol-conjugated single-stranded RNA analogues complementary to mRNAs were developed, termed 'antagomirs'. Antagomir RNAs may be synthesized using standard solid phase oligonucleotide synthesis protocols. The RNAs are conjugated to cholesterol, and may further have a phosphorothioate backbone at one or more positions.

In certain embodiments, the subject inhibitor is an RNAi agent. By RNAi agent is meant an agent that modulates expression of a gene by an RNA interference mechanism. The RNAi agents employed in one embodiment are small ribonucleic acid molecules (also referred to herein as interfering ribonucleic acids), i.e., oligoribonucleotides, that are present in duplex structures, e.g., two distinct oligoribonucleotides hybridized to each other or a single ribooligonucleotide that assumes a small hairpin formation to produce a duplex structure. By oligoribonucleotide is meant a ribonucleic acid that does not exceed about 100 nt in length, and typically does not exceed about 75 nt length, where the length in certain embodiments is less than about 70 nt. In certain embodiments, the oligoribonucleotide is less than 100, 95, 90, 85, 80, 75, 70, 65, 60, 55, 50, 45 or 40 nt in length. In certain embodiments, the oligoribonucleotide is less than 100 nt in length. In other embodiments, the oligoribonucleotide is less than 95 nt in length. In another embodiment, the oligoribonucleotide is less than 90 nt in length. In another embodiment, the oligoribonucleotide is less than 85 nt in length. In some embodiments, the oligoribonucleotide is less than 80 nt in length. In other embodiments, the oligoribonucleotide is less than 75 nt in length. In other embodiments, the oligoribonucleotide is less than 70 nt in length. In other embodiments, the oligoribonucleotide is less than 65 nt in length. In yet other embodiments, the oligoribonucleotide is less than 60 nt in length. In other embodiments, the oligoribonucleotide is less than 55 nt in length. In certain embodiments, the oligoribonucleotide is less than 50 nt in length. In other embodiments, the oligoribonucleotide is less than 45 nt in length. In yet other embodiments, the oligoribonucleotide is less than 40 nt in length. In specific embodiments, the oligoribonucleotide is 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41 or 40 nt in length.

Where the RNA agent is a duplex structure of two distinct ribonucleic acids hybridized to each other, e.g., an siRNA, the length of the duplex structure typically ranges from about 15 to 30 bp, usually from about 15 to 29 bp, where lengths between about 20 and 29 bps, e.g., 21 bp, 22 bp, are of particular interest in certain embodiments. In certain embodiments, the RNA agent is 30, 29, 28, 27, 26, 25, 24, 23, 22, 21, 20, 19, 18, 17, 16, 15, 14, 13, 12, 11 or 10 bp in length. In such embodiments, the inhibitor of the Pumilio-like protein or SR protein may be said to be a target-specific siRNA, e.g. a PUM1- or PUM2-specific siRNA, or, e.g., a SF2- or SF5- or SF9-specific siRNA.

Where the RNA agent is a duplex structure of a single ribonucleic acid that is present in a hairpin formation, i.e., a shRNA, the length of the hybridized portion of the hairpin is typically the same as that provided above for the siRNA type of agent or longer by 4-8 nucleotides. The weight of the RNAi agents of this embodiment typically ranges from about 5,000 daltons to about 35,000 daltons, and in many embodiments is at least about 10,000 daltons and less than about 27,500 daltons, often less than about 25,000 daltons. In such embodiments, the inhibitor of the Pumilio-like protein or SR protein may be said to be a target-specific shRNA, e.g. a PUM1- or PUM2-specific shRNA, or, e.g., a SF2- or SF5- or SF9-specific shRNA.

dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis. The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety).

In certain embodiments, instead of the RNAi agent being an interfering ribonucleic acid, (e.g., an siRNA or shRNA) as described above, the RNAi agent may encode an interfering ribonucleic acid, e.g., an shRNA, as described above. In other words, the RNAi agent may be a transcriptional template of the interfering ribonucleic acid. In these embodiments, the transcriptional template is typically a DNA that encodes the interfering ribonucleic acid. The DNA may be present in a vector, where a variety of different vectors are known in the art, e.g., a plasmid vector, a viral vector, etc.

In another embodiment, the subject inhibitor is an antibody that is specific for the Pumilio-like protein or SR protein, e.g. a PUM1- or PUM2-specific antibody, or, e.g., a SF2- or SF5- or SF9-specific antibody. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The term includes monoclonal antibodies, multispecific antibodies (antibodies that include more than one domain specificity), human antibody, humanized antibody, and antibody fragments with the desired biological activity.

Polyclonal antibodies can be raised by a standard protocol by injecting a production animal with an antigenic composition, formulated as described above. See, e.g., Harlow and Lane, Antibodies: A Laboratory Manual, Cold Spring Harbor Laboratory, 1988. In one such technique, a Class II target antigen comprising an antigenic portion of the polypeptide is initially injected into any of a wide variety of mammals (e.g., mice, rats, rabbits, sheep or goats). When utilizing an entire protein, or a larger section of the protein, antibodies may be raised by immunizing the production animal with the protein and a suitable adjuvant (e.g., Freund's, Freund's complete, oil-in-water emulsions, etc.) Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line.

In addition, the antibodies or antigen binding fragments may be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones, which co-express a heavy and light chain (resembling the Fab fragment or antigen binding fragment of an antibody molecule). The vectors that carry these genes are co-transfected into a host (e.g., bacteria, insect cells, mammalian cells, or other suitable protein production host cell). When antibody gene synthesis is induced in the transfected host, the heavy and light chain proteins self-assemble to produce active antibodies that can be detected by screening with the antigen or immunogen.

Antibodies with a reduced propensity to induce a violent or detrimental immune response in humans (such as anaphylactic shock), and which also exhibit a reduced propensity for priming an immune response which would prevent repeated dosage with the antibody therapeutic are preferred for use in the invention. Thus, humanized, single chain, chimeric, or human antibodies, which produce less of an immune response when administered to humans, are preferred for use in the present invention. Also included in the invention are multi-domain antibodies.

A chimeric antibody is a molecule in which different portions are derived from different animal species, for example those having a variable region derived from a murine mAb and a human immunoglobulin constant region. Techniques for the development of chimeric antibodies are described in the literature. See, e.g., Morrison et al. (1984) *Proc. Natl. Acad. Sci.* 81:6851-6855; Neuberger et al. (1984) *Nature* 312:604-608; Takeda et al. (1985) *Nature* 314:452-454. Single chain antibodies are formed by linking the heavy and light chain fragments of the Fv region via an amino acid bridge, resulting in a single chain polypeptide. See, e.g., Huston et al., *Science* 242:423-426; *Proc. Natl. Acad. Sci.* 85:5879-5883; and Ward et al. *Nature* 341:544-546.

In addition to entire immunoglobulins (or their recombinant counterparts), immunoglobulin fragments comprising the epitope binding site (e.g., Fab', F(ab')$_2$, or other fragments) are useful as antibody moieties in the methods described herein. Such antibody fragments may be generated from whole immunoglobulins by ficin, pepsin, papain, or other protease cleavage. "Fragment," or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif).

Antibody fragments that recognize specific epitopes may be generated by techniques well known in the field. For instance, F(ab')$_2$ fragments can be produced by pepsin digestion of the antibody molecule, and Fab fragments are generated by reducing the disulfide bridges of the F(ab')$_2$ fragments. Single chain antibodies (Fv) can be produced from phage libraries containing human variable regions. See U.S. Pat. No. 6,174,708. Intrathecal administration of single-chain immunotoxin, LMB-7 [B3(Fv)-PE38], has been shown to cure of carcinomatous meningitis in a rat model. *Proc Natl. Acad. Sci USA* 92, 2765-9, all of which are incorporated by reference fully herein.

In certain embodiments, the subject antibody inhibitor is a F(ab')$_2$ fragment. In other embodiments, the subject antibody inhibitor is a Fab' fragment.

In some embodiments, the subject inhibitor is a small molecule (i.e. "a small molecule inhibitor"). By a "small molecule" it is meant a naturally occurring or synthetic small molecule compounds, including numerous chemical classes, though typically they are organic molecules, e.g. small organic compounds having a molecular weight of more than 50 and less than about 2,500 daltons. Small molecule inhibitors of PUM1 or SF2 may comprise functional groups necessary for structural interactions, particularly hydrogen bonding, and typically include at least an amine, carbonyl, hydroxyl or carboxyl group, frequently at least two of the functional chemical groups. These small molecule inhibitors often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition. Compounds may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In certain embodiments, the subject small molecule inhibitor is an organic molecule comprising functional groups necessary for structural interactions, particularly hydrogen bonding, and typically include at least an amine, carbonyl, hydroxyl or carboxyl group, frequently at least two of the functional chemical groups. The inhibitor of Pumilio-like protein or SR protein may comprise cyclical carbon or heterocyclic structures and/or aromatic or polyaromatic structures substituted with one or more of the above functional groups. Inhibitors of Pumilio-like protein or SR protein are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition.

An agent may be tested to confirm its biological activity as inhibitors of Pumilio-like protein or SR protein activity by adding the agent to one or a plurality of cell samples (e.g., neurons), usually in conjunction with cells lacking the agent. The change in parameters in response to the agent is measured, and the result evaluated by comparison to reference cultures, e.g., in the presence and absence of the agent, obtained with other agents, etc. Non-limiting examples of parameters that may be measured include the phosphorylation state of the Pumilio-like protein or SR protein; the stability of RNA sequences, e.g. RNA targets of Pumilio-like proteins; the extent of pre-mRNA or alternative splicing of RNA sequences, e.g. RNA targets of SR proteins, the distribution and morphology of mitochondria in the processes of the neuron cell samples, or the ATP levels of the neuron cell samples.

Antibody inhibitors, in particular, can be tested by any suitable standard means, e.g., ELISA assays, etc. As a first test, the antibodies may be tested for binding against the immunogen. After selective binding is established, the candidate antibody may be tested for appropriate activity in an in vivo model. In a preferred embodiment, antibody compounds may be screened using a variety of methods in vitro and in vivo. These methods include, but are not limited to, methods that measure binding affinity to a target, biodistribution of the compound within an animal or cell, or compound mediated cytotoxicity. These and other screening methods known in the art provide information on the ability of a compound to bind to, modulate, or otherwise interact with the specified target and are a measure of the compound's efficacy.

The Pumilio-like protein inhibitor or SR protein inhibitor described herein may be administered alone or in combination with any pharmaceutically acceptable carrier or salt known in the art and as described below.

Pharmaceutical Compositions

In some aspects, the inhibitors disclosed herein are provided in a pharmaceutical composition comprising a therapeutically effective amount of any of the inhibitors (e.g., a Pumilio-like protein (e.g., PUM1) inhibitor or SR protein (e.g., SF2) inhibitor) provided herein, together with a suitable amount of carrier so as to provide the form for proper administration to a patient.

The term "pharmaceutically acceptable" means approved by a regulatory agency of the Federal or a state government or listed in the U.S. Pharmacopeia or other generally recognized foreign pharmacopeia for use in animals, and more particularly in humans. The term "carrier" refers to a diluent, adjuvant, excipient, or vehicle with which the PUM1 or SF2 inhibitor is administered. Such pharmaceutical carriers can be, for example, sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. The inhibitors can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin, hereby incorporated by reference herein in its entirety. Such compositions will contain a therapeutically effective amount of the Pumilio-like protein (e.g., PUM1) or SR protein (e.g., SF2) inhibitor, preferably in purified form, together with a suitable amount of carrier so as to provide the form for proper administration to the patient. The formulation should suit the mode of administration.

The pharmaceutical composition can be formulated for intravenous, oral, via implant, transmucosal, transdermal, intramuscular, intrathecal, or subcutaneous administration. In some embodiments, the pharmaceutical composition is formulated for intravenous administration. In other embodiments, the pharmaceutical composition is formulated for subcutaneous administration. The following delivery systems, which employ a number of routinely used pharmaceutical carriers, are only representative of the many embodiments envisioned for administering the instant compositions.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGAs). Implantable systems include rods and discs, and can contain excipients such as PLGA and polycaprylactone. Osteopontin or nucleic acids of the invention can also be administered attached to particles using a gene gun.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Components of the pharmaceutical composition can be supplied either separately or mixed together in unit dosage form, for example, as a dry lyophilized powder or water free concentrate. Where the composition is to be administered by infusion, it can be dispensed with an infusion bottle containing sterile pharmaceutical grade water or saline. Where the composition is administered by injection, an ample of sterile water for injection or saline can be provided so that the ingredients may be mixed prior to administration.

In some embodiments, the pharmaceutical composition is supplied as a dry sterilized lyophilized powder that is capable of being reconstituted to the appropriate concentration for administration to a subject. In some embodiments, the pharmaceutical composition is supplied as a water free concentrate. In some embodiments, the pharmaceutical composition is supplied as a dry sterile lyophilized powder at a unit dosage of at least 0.5 mg, at least 1 mg, at least 2 mg, at least 3 mg, at least 5 mg, at least 10 mg, at least 15 mg, at least 25 mg, at least 30 mg, at least 35 mg, at least 45 mg, at least 50 mg, at least 60 mg, or at least 75 mg.

Solutions, suspensions and powders for reconstitutable delivery systems include vehicles such as suspending agents (e.g., gums, xanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

In some embodiments, the pharmaceutical composition is formulated as a salt form. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Methods of Treatment

In some aspects, provided herein are methods for the treatment or amelioration of a mitochondrial disease, e.g. a mitochondrial myopathy, e.g. chronic progressive external ophthalmoplegia (CPEO), Kearns Sayre syndrome (KSS), or Myoclonus epilepsy ragged-red fibers (MERRF); Leigh's syndrome (subacute sclerosing encephalopathy); Myoneurogenic gastrointestinal encephalopathy (MNGIE); Diabetes mellitus and deafness (DAD); mitochondrial encephalomyopathy, lactic acidosis and stroke-like episodes (MELAS); or a mitochondrial neuropathy, e.g., Parkinson's Disease (PD), Neuropathy ataxia retinitis pigmentosa (NARP), or Leber's hereditary optic neuropathy (LHON), and the like, in a subject having or at risk for developing the mitochondrial disease, the method comprising administering to the subject a therapeutically effective amount the subject inhibitor(s), i.e. a Pumilio-like protein (e.g., PUM1) inhibitor and/or SR protein (e.g., SF2) inhibitor, or pharmaceutical composition thereof as described herein. In other words, cells of the subject, e.g. neuron or muscle cells, are contacted in vivo with one or more of the subject inhibitors. For example, in the treatment of a subject having Parkinson's Disease, one or more neurons, e.g. dopaminergic neurons, e.g. a dopaminergic neuron residing in of the substantia nigra of the midbrain and/or putamen, is contacted with one or more of the subject inhibitor(s). Cells in vivo may be contacted with one or more of the subject inhibitors suitable for pharmaceutical use by any convenient method for the administration of polypeptides, and nucleic acids, or small molecules to a subject, e.g. as described herein or known in the art. Often, the subject is a mammal. Mammalian species that may be treated with the present methods include canines; felines; equines; bovines; ovines; etc. and primates, particularly humans. In some embodiments, the method is for the treatment of a human. Animal models, particularly small mammals, e.g., murine, lagomorpha, etc. may be used for experimental investigations By a "therapeutically effective amount" of the subject inhibitor it is meant an amount that is required to reduce the severity, the duration and/or the symptoms of the mitochondrial disease, e.g. as described herein or as known in the art. For example, the therapeutically effective amount may slow the rate of progression of the disease and the increase of severity of clinical symptoms, may halt the progression of the disease and the clinical symptoms, or may cause a regression of the disease and the clinical symptoms. In some instances, the method further comprises the step of measuring one or more of the clinical symptoms of the mitochondrial disease, e.g. motor symptoms, neuronal symptoms, etc., e.g. as described herein or known in the art before and/or after treatment with the subject inhibitor(s) and determining that the one or more symptoms have been reduced.

The calculation of the effective amount or effective dose of the inhibitor or pharmaceutical composition to be administered is within the skill of one of ordinary skill in the art, and will be routine to those persons skilled in the art by using assays known in the art, e.g. as described herein. The effective amount of an inhibitor or pharmaceutical composition to be given to a particular patient will depend on a variety of factors, several of which will differ from patient to patient. A competent clinician will be able to determine an effective amount of a therapeutic agent to administer to a patient to halt or reverse the progression the disease condition as required. For example, the effective amount may be dependent upon the route of administration and the seriousness of the mitochondrial disease, and should be decided according to the judgment of the practitioner and each human patient's circumstances.

Determining a therapeutically effective amount of the inhibitor can be done based on animal data using routine computational methods. For example, effective amounts may be extrapolated from dose-response curves derived from preclinical protocols either in vitro (e.g., dopaminergic neuron cultures, such as the ones described below, treated with rotenone or MPP+ for 24 h, or with Epoxymicin for 48 h) or using any of the in vivo mitochondrial disease animal models known in the art (e.g., 6-hydroxydopamine (6-OHDA) rat model, MPTP mouse or primate model or rotenone model). See, for example, Duty et al., *Br J Pharmacol.* 164(4): 1357-1391 (2011), incorporated herein by reference. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

The subject inhibitor(s) can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized. The inhibitor be administered daily, semi-weekly, weekly, semi-monthly, monthly, etc., at a dose of from about 0.01 mg, from about 0.1 mg, from about 1 mg, from about 5 mg, from about 10 mg, from about 100 mg or more per kilogram of body weight when administered systemically. Smaller doses may be utilized in localized administration, e.g., in direct administration to ocular nerves, etc.

Pharmaceutical preparations are compositions that include one or more subject inhibitor(s) present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semi-solid, liquid or gaseous forms, such as tablets, capsules, powders, granules, ointments, solutions, suppositories, injections, inhalants, gels, microspheres, and aerosols. As such, administration of the subject inhibitor(s) can be achieved in various ways, including oral, buccal, rectal, parenteral, intraperitoneal, intradermal, transdermal, intracheal, etc., administration. The pharmaceutical composition comprising the inhibitor may be systemic after administration or may be localized by the use of regional administration, intramural administration, or use of an implant that acts to retain the active dose at the site of implantation. The pharmaceutical composition comprising the subject inhibitor(s) may be formulated for immediate activity or they may be formulated for sustained release.

In certain embodiments, the pharmaceutical composition comprising the subject inhibitor(s) is formulated to cross the blood brain barrier (BBB). One strategy for drug delivery through the blood brain barrier (BBB) entails disruption of the BBB, either by osmotic means such as mannitol or leukotrienes, or biochemically by the use of vasoactive substances such as bradykinin. A BBB disrupting agent can be co-administered with the therapeutic compositions when the compositions are administered by intravascular injection. Other strategies to go through the BBB may entail the use of endogenous transport systems, including caveoil-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the invention to facilitate transport across the endothelial wall of the blood vessel. Alternatively, drug delivery of the ND pharmaceutical composition behind the BBB may be by local delivery, for example by intrathecal delivery, e.g., through an Ommaya reservoir (see, e.g., U.S. Pat. Nos. 5,222,982 and 5,385,582, incorporated herein by reference); by bolus injection, e.g., by a syringe, e.g., intravitreally or intracranially; by continuous infusion, e.g., by cannulation, e.g., with convection (see, e.g., US Application No. 20070254842, incorporated here by reference); or by implanting a device upon which the inhibitor pharmaceutical composition has been reversably affixed (see e.g., US Application Nos. 20080081064 and 20090196903, incorporated herein by reference).

A subject inhibitor for pharmaceutical use, i.e. a Pumilio-like protein (e.g., PUM1) or SR protein (e.g., SF2) inhibitor pharmaceutical composition, can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The pharmaceutical composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

For inclusion in a medicament, the subject inhibitor(s) may be obtained from a suitable commercial source (e.g., anti-PUM1 antibody (Catalog Number ab92545; AbCam; Cambridge, Mass.); anti-SF2 antibody (Catalog Number ab38017; AbCam; Cambridge, Mass.)). As a general proposition, the total pharmaceutically effective amount of the compound administered parenterally per dose will be in a range that can be measured by a dose response curve.

The subject inhibitor(s) or pharmaceutical composition thereof to be used for therapeutic administration is typically sterile. Sterility is readily accomplished by filtration through sterile filtration membranes (e.g., 0.2 μm membranes). Therapeutic compositions generally are placed into a container having a sterile access port, for example, an intravenous solution bag or vial having a stopper pierceable by a hypodermic injection needle. The inhibitor or pharmaceutical composition thereof ordinarily will be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The pharmaceutical composition comprising the lyophilized inhibitor(s) is prepared by reconstituting the lyophilized compound, for example, by using bacteriostatic Water-for-Injection.

In some embodiments, the effective amount of the pharmaceutical composition provided herein is between about 0.025 mg/kg and about 1000 mg/kg body weight of a human subject. In certain embodiments, the pharmaceutical composition is administered to a human subject at an amount of about 1000 mg/kg body weight or less, about 950 mg/kg body weight or less, about 900 mg/kg body weight or less, about 850 mg/kg body weight or less, about 800 mg/kg body weight or less, about 750 mg/kg body weight or less, about 700 mg/kg body weight or less, about 650 mg/kg body weight or less, about 600 mg/kg body weight or less, about 550 mg/kg body weight or less, about 500 mg/kg body weight or less, about 450 mg/kg body weight or less, about 400 mg/kg body weight or less, about 350 mg/kg body weight or less, about 300 mg/kg body weight or less, about 250 mg/kg body weight or less, about 200 mg/kg body weight or less, about 150 mg/kg body weight or less, about 100 mg/kg body weight or less, about 95 mg/kg body weight or less, about 90 mg/kg body weight or less, about 85 mg/kg body weight or less, about 80 mg/kg body weight or less, about 75 mg/kg body weight or less, about 70 mg/kg body weight or less, or about 65 mg/kg body weight or less.

In some embodiments, the effective amount of the pharmaceutical composition provided herein is between about 0.025 mg/kg and about 60 mg/kg body weight of a human subject. In some embodiments, the effective amount of an antibody of the pharmaceutical composition provided herein is about 0.025 mg/kg or less, about 0.05 mg/kg or less, about 0.10 mg/kg or less, about 0.20 mg/kg or less, about 0.40 mg/kg or less, about 0.80 mg/kg or less, about 1.0 mg/kg or less, about 1.5 mg/kg or less, about 3 mg/kg or less, about 5 mg/kg or less, about 10 mg/kg or less, about 15 mg/kg or less, about 20 mg/kg or less, about 25 mg/kg or less, about 30 mg/kg or less, about 35 mg/kg or less, about 40 mg/kg or less, about 45 mg/kg or less, about 50 mg/kg or about 60 mg/kg or less.

In certain embodiments, the subject inhibitor(s) or pharmaceutical compositions thereof can be administered in combination with an additional therapeutic agent for the treatment or amelioration of the mitochondrial disease. For example, for a subject having Parkinson's Disease, such therapeutic agents would include, but are not limited to, levodopa (alone or in combination with a dopa decarboxylase inhibitor or COMT inhibitor), dopamine agonists (e.g., bromocriptine, pergolide, pramipexole, ropinirole, piribedil, cabergoline, apomorphine, and lisuride), MAO-B inhibitors (e.g., selegiline and rasagiline), amantadine, and anticholinergics. Other therapeutics with which the subject inhibitors may be administered include polypeptides, peptides, antibodies, nucleic acids, or small molecules that act as a Parkin agonist, a PINK1 agonist, an 4E-BP1 agonist, a Drp1 agonist, an Atg1 agonist, a Miro antagonist, a TauS2A agonist, a Rbf1 agonist, a Dp antagonist, an E2f1 antagonist, a Polo-like kinase 2 antagonist or a Notch agonist. By an agonist, it is meant an agent that induces, promotes, enhances the expression or activity of a gene or gene product, for example, a cDNA that encodes one of the aforementioned gene products, a polypeptide or peptide mimetic that encodes one of the aforementioned gene products, a polypeptide or peptide that encodes a protein that activates one of the aforementioned gene products, an activating antibody that is specific for one of the aforementioned gene products, and the like. By an antagonist, it is meant an agent that reduces, suppresses, or inhibits the expression or activity of a gene or gene product, for example, an RNA (e.g. siRNA, antisense RNA, etc., as described elsewhere herein or known in the art) that is specific for one of the aforementioned gene products, a blocking antibody that is specific for one of the aforementioned gene products, or a small molecule that inhibits the activity of one of the aforementioned gene products). In some embodiments, the subject inhibitor(s) are provided at the same time as the additional therapeutic. In some embodiments, the subject inhibitor(s) are provided before the additional therapeutic. In some embodiments, the subject inhibitor(s) are provide after the additional therapeutic.

Utility

The subject compositions and methods find use in the treatment of mitochondrial diseases. By a mitochondrial disease, it is meant any disease associated with mitochondrial function, for example, a mitochondrial myopathy, e.g., chronic progressive external ophthalmoplegia (CPEO), Kearns Sayre syndrome (KSS), or Myoclonus epilepsy ragged-red fibers (MERRF); Leigh's syndrome (subacute sclerosing encephalopathy); Myoneurogenic gastrointestinal encephalopathy (MNGIE); Diabetes mellitus and deafness (DAD); mitochondrial encephalomyopathy, lactic acidosis and stroke-like episodes (MELAS); or a mitochondrial neuropathy, e.g., Parkinson's Disease (PD), Neuropathy ataxia retinitis pigmentosa (NARP), or Leber's hereditary optic neuropathy (LHON). Chronic progressive external ophthalmoplegia. Chronic progressive external ophthalmoplegia (abbreviated CPEO) is a mitochondrial myopathy syndrome that is characterized by isolated involvement of the muscles controlling eyelid movement (levator palpebrae, orbicularis oculi), and those controlling eye movement (extra-ocular muscles). This results in ptosis and ophthalmoplegia respectively. CPEO is most commonly caused by the mitochondrial DNA point mutation A3243G.

Kearns-Sayre Syndrome.

Kearns-Sayre syndrome (KSS) also known as oculocraniosomatic disease or Oculocraniosomatic neuromuscular disease with ragged red fibers, is a slowly progressive multi-system mitochondrial disease with a typical onset before 20 years of age. KSS is a more severe syndromic variant of CPEO. KSS involves a paralysis of the same eye muscles as in CPEO. In addition, bilateral pigmentary retinopathy and cardiac conduction abnormalities are observed. Other areas of involvement can include cerebellar ataxia, proximal muscle weakness, deafness, diabetes mellitus, growth hormone deficiency, hypoparathyroidism, or other endocrinopathies. As with CPEO, muscle involvement may begin unilateral but always develops into a bilateral deficit, and the course is progressive. KSS is usually caused by a single large deletion of genetic material within the mitochondrial DNA. These deletions, over 150 of which have been observed, are typically spontaneous. Less frequently, the mutation is transmitted by the mother.

Myoclonus Epilepsy Ragged-Red Fibers.

Myoclonus epilepsy ragged-red fibers (MERRF) syndrome is a progressive multi-system syndrome usually beginning in childhood, but onset may occur in adulthood. The rate of progression varies widely. Onset and extent of symptoms can differ among affected siblings. Symptoms include progressive myoclonic epilepsy, "Ragged Red Fibers", in which clumps of diseased mitochondria accumulate in the subsarcolemmal region of the muscle fiber and appear as ragged red fibers" when muscle is stained with modified Gömöri trichrome stain, short stature, hearing loss, lactic acidosis, exercise intolerance, and poor night vision. Other symptoms may include epileptic seizures, and ataxia.

Over 80% of MERRF cases are caused by a maternally-inherited mutation at position 8344 in the mitochondrial genome. This point mutation disrupts the mitochondrial gene encoding the transfer RNA tRNA-Lysine (MT-TK gene in humans). Other mutations associated with MERRF include mutations on the genes MT-TL1 (encoding the tRNA leucine 1), MT-TH (encoding tRNA histidine), MT-TS1 (encoding serine 1), MT-TS2 (encoding serine 2), and MT-TF (encoding tRNA phenylalanine).

Leigh Syndrome.

Leigh syndrome, also known as juvenile subacute necrotizing encephalomyelopathy, Leigh syndrome, infantile subacute necrotizing encephalomyelopathy, and subacute necrotizing encephalomyelopathy (SNEM), is a rare neurometabolic disorder that affects the central nervous system. The symptoms of Leigh's disease typically begin within a year of a child's birth and lead to death within a span of several years, though symptoms can appear anytime between the ages of three months and two years or very rarely in adolescence or adulthood. Infants with the syndrome have symptoms that include diarrhea, vomiting, and dysphagia (trouble swallowing or sucking), leading to a failure to thrive. Children with early Leigh disease also may appear irritable and cry much more than usual. Seizures are often seen. Excess lactate may be seen in the urine, cerebrospinal fluid, and blood of a person with Leigh syndrome in a condition called lactic acidosis. As the disease progresses, the muscular system is debilitated throughout the body, as the brain cannot control the contraction of muscles. Hypotonia (low muscle tone and strength), dystonia (involuntary, sustained muscle contraction), and ataxia (lack of control over movement) are often seen in people with Leigh's disease. The eyes are particularly affected; the muscles that control the eyes become weak, paralyzed, or uncontrollable in conditions called ophthalmoparesis (weakness or paralysis) and nystagmus (involuntary eye movements). The heart and lungs can also fail as a result of Leigh's disease. Hypertrophic cardiomyopathy, thickening of part of the heart muscle, is also sometimes found and can cause death. However, respiratory failure is the most common ultimate cause of death in people with Leigh syndrome. Other neurological symptoms include peripheral neuropathy, loss of sensation in extremities caused by damage to the peripheral nervous system.

At least 26 genetic mutations have been identified that cause Leigh syndrome. These include mutations that result in a pyruvate dehydrogenase (PDHC) deficiency, and mutations in respiratory chain enzymes, Complexes I, II, IV, and V. Both familial (i.e. inherited) and sporadic forms of the disease exist.

Myoneurogenic Gastrointestinal Encephalopathy.

Myoneurogenic gastrointestinal encephalopathy (MNGIE) is a multisystem disorder that usually appears between the second and fifth decades of life. Abnormalities of the digestive system are among the most common and severe features of MNGIE disease. Gastrointestinal symptoms may include gastrointestinal dysmotility possibly resulting in pseudo-obstruction in which the muscular contractions (peristalsis) of the gastrointestinal tract become inefficient causing malabsorption. Borborygmi (stomach rumbling), early satiety, diarrhea, constipation, gastroparesis, nausea, vomiting, weight loss, and diverticulitis can occur.

MNGIE is also characterized by abnormalities of the nervous system, although these tend to be milder than the gastrointestinal problems. Affected individuals experience tingling, numbness, and weakness in their limbs (peripheral neuropathy), particularly in the hands and feet. Additional neurological signs and symptoms can include droopy eyelids (ptosis), weakness of the muscles that control eye movement (ophthalmoplegia), and hearing loss. Leukoencephalopathy, which is the deterioration of the white matter of the brain, is a hallmark. These changes in the brain can be seen with magnetic resonance imaging (MRI).

Diabetes Mellitus and Deafness.

Diabetes mellitus and deafness (DAD), and more particularly, maternally inherited diabetes and deafness (MIDD), is a form of diabetes that is often accompanied by hearing loss, especially of high tones. The diabetes in MIDD is characterized by hyperglycemia resulting from a shortage of the hormone insulin. In MIDD, the diabetes and hearing loss usually develop in mid-adulthood, although the age that they occur varies from childhood to late adulthood. Typically, hearing loss occurs before diabetes.

In some instances, MIDD may be associated with the eye disorder called macular retinal dystrophy, which is characterized by colored patches in the light-sensitive tissue that lines the back of the eye (the retina). This disorder does not usually cause vision problems in people with MIDD. Individuals with MIDD also may experience muscle cramps or weakness, particularly during exercise; heart problems; kidney disease; and constipation. Individuals with MIDD are often shorter than their peers.

MIDD is most commonly caused by mutations in the mitochondrial genes MT-TL1, MT-TK, or MT-TE genes (encoding tRNA leucine 1, tRNA lysine, and tRNA glutamic acid, respectively).

Mitochondrial Encephalomyopathy, Lactic Acidosis, and Stroke-Like Episodes.

Mitochondrial encephalomyopathy, lactic acidosis, and stroke-like episodes (MELAS) is a multisystem condition that affects the brain and nervous system (encephalo-) and muscles (myopathy). The signs and symptoms of this disorder most often appear in childhood following a period of normal development, although they can begin at any age. Early symptoms may include muscle weakness and pain, recurrent headaches, loss of appetite, vomiting, and seizures. Stroke-like episodes, often accompanied by seizures, are the hallmark symptom of MELAS and cause partial paralysis, loss of vision, and focal neurological defects. The gradual cumulative effects of these episodes often result in variable combinations of loss of motor skills (speech, movement, and eating), impaired sensation (vision loss and loss of body sensations), and mental impairment (dementia). MELAS patients may also suffer additional symptoms including: muscle weakness, peripheral nerve dysfunction, diabetes, hearing loss, cardiac and kidney problems, and digestive abnormalities. Lactic acid usually accumulates at high levels in the blood, cerebrospinal fluid, or both.

MELAS is maternally inherited due to a mutation in mitochondrial DNA. There are at least 17 different mutations that can cause MELAS, the most prevalent being the A3243G mutation, which is responsible for about 80% of the cases.

Parkinson's Disease.

Parkinson's disease (PD) also known as idiopathic or primary parkinsonism, hypokinetic rigid syndrome/HRS, or paralysis agitans, is a degenerative disorder of the central nervous system. The motor symptoms of Parkinson's disease result from the death of dopamine-generating neurons in the substantia nigra, a region of the midbrain, and putamen; the cause of this cell death is unknown. Early in the course of the disease, the most obvious symptoms are movement-related; these include shaking, rigidity, resting tremors, bradykinesia, postural stability, slowness of movement and difficulty with walking and gait. Later, thinking and behavioral problems may arise, with dementia, e.g. cognitive impairment, hallucinations, delusion, behavioral abnormalities, depression, disturbance of sleep and wakefulness, commonly occurring in the advanced stages of the disease, whereas depression is the most common psychiatric symptom. Other symptoms include sensory (loss of smell), sleep (disturbance of sleep and wakefulness) and emotional problems, constipation, hypotension, urinary frequency, impotence and sweating. Parkinson's disease is more common in older people, with most cases occurring after the age of 50.

Parkinson's Disease may be of the familial form or the sporadic form. By a familial form, it is meant that the disease is inherited, i.e. by the passage of a heritable gene mutation from parent to child through the gametes. A number of different heritable mutations have been associated with PD, including for example, mutations in PTEN-induced putative kinase 1 (PINK-1); Parkin (also known as RBR E3 ubiquitin protein ligase, or PARK2); leucine-rich repeat kinase 2 (LRRK2); alpha-Synuclein (SNCA, PARK4); ubiquitin carboxy-terminal hydrolase L1 (UCHL1); parkinson protein 7 (PARK7, DJ-1); ATPase type 13A2 (ATP13A2); phospholipase A2, group VI (PLA2G6); DnaJ (Hsp40) homolog, subfamily C, member 6 (DNAJC6, PARK19); eukaryotic translation initiation factor 4 gamma, 1 (EIF4G1, PARK18); F-box protein 7 (FBXO7); GRB10 interacting GYF protein 2 (GIGYF2); HtrA serine peptidase 2 (HTRA2); synaptojanin 1 (SYNJ1); or vacuolar protein sorting 35 homolog (VPS35). By a sporadic form, it is meant that the disease occurs sporadically, i.e. due to sporadic mutation of a gene, e.g. one of the aforementioned genes.

Neuropathy, Ataxia, and Retinitis Pigmentosa.

Neuropathy ataxia retinitis pigmentosa (NARP) is a condition that causes a variety of signs and symptoms chiefly affecting the nervous system. Beginning in childhood or early adulthood, most people with NARP experience numbness, tingling, or pain in the arms and legs (sensory neuropathy); muscle weakness; and problems with balance and coordination (ataxia). Many affected individuals also have vision loss caused by changes in the light-sensitive tissue that lines the back of the eye (the retina). In some cases, the vision loss results from a condition called retinitis pigmentosa. This eye disease causes the light-sensing cells of the retina gradually to deteriorate. Learning disabilities and developmental delays are often seen in children with NARP, and older individuals with this condition may experience a loss of cognitive functions (dementia). Other features of NARP include seizures, hearing loss, and cardiac conduction defects. These signs and symptoms vary among affected individuals. NARP has been associated with point mutations in the mitochondrial gene MT-ATP6, which encodes one subunit of ATP synthase (also known complex V).

Leber's Hereditary Optic Neuropathy.

Leber's hereditary optic neuropathy (LHON) is an eye disorder characterized by progressive loss of central vision due to degeneration of the optic nerves and retina. Blurring and clouding of vision are usually the first symptoms of LHON. These vision problems may begin in one eye or simultaneously in both eyes; if vision loss starts in one eye, the other eye is usually affected within several weeks or months. Over time, vision in both eyes worsens with a severe loss of visual acuity and color vision. This condition mainly affects central vision, which is needed for detailed tasks such as reading, driving, and recognizing faces. Vision loss results from the death of the optic nerve. Although central vision gradually improves in a small percentage of cases, in most cases the vision loss is profound and permanent.

Vision loss is typically the only symptom of LHON; however, some families with additional signs and symptoms have been reported. In these individuals, the condition is described as "LHON plus." In addition to vision loss, the features of LHON plus can include movement disorders, tremors, and cardiac conduction defects. Some affected individuals develop features similar to multiple sclerosis, which is a chronic disorder characterized by muscle weakness, poor coordination, numbness, and a variety of other health problems.

Mutations in the mitochondrial genes MT-ND1, MT-ND4, MT-ND4L, and MT-ND6 can cause LHON. These genes encode NADH dehydrogenases, which together form Complex I of the respiratory chain.

In some embodiments, the method comprises determining if the subject has the mitochondrial disease, and then providing one or more of the subject inhibitors to treat the disease. Any convenient method for determining if the subject has the mitochondrial disease may be used, including, for example, assessing for the aforementioned symptoms or performing genetic testing to detect a mutation associated with the disease, e.g. as described above or as known in the art. In some embodiments, the method comprises detecting one or more of the symptoms of the disease, administering the subject inhibitor(s), and assaying for the symptom(s) after administration, where the administration of the subject inhibitor inhibits, suppress, or moderate the symptoms of the mitochondrial disease.

Compositions and Methods for Differentiation of Target Cells to Neurons

Also provided herein are compositions, methods and systems for differentiating a target cell (e.g., a somatic cell) to a mature neuron (the "induced neuron"). In certain embodiments, the compositions, methods, and systems are for transdifferentiating a target cell (e.g. a somatic cell) to a mature neuron (the "induced neuron"). Such compositions, methods, and systems advantageously allow for the production of a neuron directly from a target somatic cell, without having to go through an intermediate step of reprogramming the target cell to a pluripotent cell. Further, in some embodiments, the mature neurons produced by the methods described herein do not undergo proliferation and, as such, are advantageously free of undesirable mutations associated with cell proliferation. Neurons produced by the methods provided herein can be used, for example, in screens for candidate agents for the treatment of Parkinson's Disease. In specific embodiments, the induced neuron produced is a dopaminergic neuron.

Neuron Differentiation (ND) Factors

Provided herein are neuron differentiation factors for the differentiation of a target cell (e.g. a somatic cell) to mature neurons. By "neuron differentiation factors" or "ND factors" it is meant one or more biologically active factors that act on a target cell to alter transcription so as to convert the target cell into a neuron, i.e. an induced neuron. In specific embodiments, the neuron differentiation factors are neuron transdifferentiation factors ("NT factors"). Such NT factors when contacted with a target somatic cell (e.g. a non-neuronal somatic cell) can allow for production of a neuron directly from a target somatic cell without having to go through an intermediate step of reprogramming the target cell to a pluripotent cell. ND factors are provided to target cells in the context of an ND system. Examples of ND factors include, but are not limited to, a LIM homeobox transcription factor (Lmx) agent, a nuclear receptor (NR) agent, a c-Fos agent, and an Early B Cell Factor (EBF) agent.

LIM Homeobox Transcription Factor (Lmx) Agents.

In some embodiments, the ND factor is a LIM homeobox transcription factor (Lmx) agent. In certain embodiments, the LIM homeobox transcription factor (Lmx) agent is a LIM hopebox transcription factor polypeptide. LIM homeobox transcription factor (Lmx) polypeptides are member of a family of transcriptional regulators that carry the LIM domain, a cysteine-rich zinc-binding domain. The terms "LIM homeobox transcription factor gene product," "LIM homeobox transcription factor gene peptide," and "LIM homeobox transcription factor protein," are used interchangeably herein to refer to native sequence LIM homeobox transcription factor polypeptides, polypeptide variants, polypeptide fragments, and chimeric LIM homeobox transcription factor polypeptides that can modulate transcription. Native sequence LIM homeobox transcription factor polypeptides include, but are not limited to, Lmx1a (e.g., GenBank Accession Nos. NM_001174069.1 and NP_001167540.1) and Lmx1b (e.g., GenBank Accession Nos. NM_001174146.1 and NP_001167617.1). In certain embodiments, the Lmx polypeptide is at least 50%, 55%, 60%, 65%, 70%, 75%, 80%, 85%, 90%, 91%, 92%, 93%, 94%, 95%, 96%, 97%, 98%, 99% or 100% identical to the sequence provided in one or more of the GenBank Accession Nos. above. In yet other embodiments, the Lmx agent is the nucleic acids encoding any of the Lmx polypeptides described herein or their transcription active domains or the vector comprising these nucleic acids. In specific embodiments, the Lmx agent is a Lmx1 b agent.

Nuclear Receptor Subfamily 4 (NR4) Agents.

As used herein, the terms "nuclear receptor subfamily 4" and "NR4" refers to a member of a family of nerve growth factor-induced clone B group orphan receptors that function as DNA-binding transcription factors. NR4 family members include, but are not limited to NGFI-B (NR4A1) (GenBank Accession Nos. NM_001202233.1 and NP_00189162.1), Nurr1 (NR4A2) (GenBank Accession Nos. NM_006186.3 and NP_006177.1); and NOR1 (NR4A3) (GenBank Accession Nos. NM_006981.3 and NP_008912.2).

In some embodiments, the ND factor is a nuclear receptor subfamily 4 (NR4) agent. In certain embodiments, the NR4 agent is an NR4 polypeptide. NR4 polypeptides are members of a family of nerve growth factor-induced clone B group orphan receptors that function as DNA-binding transcription factors. NR4 family members include, but are not limited to NGFI-B (NR4A1) (GenBank Accession Nos. NM_001202233.1 and NP_00189162.1), Nurr1 (NR4A2) (GenBank Accession Nos. NM_006186.3 and NP_006177.1); and NOR1 (NR4A3) (GenBank Accession Nos. NM_006981.3 and NP_008912.2). The terms "NR4 gene product," "NR4 gene peptide," and "NR4 protein," are used interchangeably herein to refer to native sequence NR4 polypeptides, polypeptide variants, polypeptide fragments, and chimeric NR4 polypeptides that can modulate transcription. In certain embodiments, the NR4 polypeptide is at least 50%, 55%, 60%, 65%, 70%, 75%, 80%, 85%, 90%, 91%, 92%, 93%, 94%, 95%, 96%, 97%, 98%, 99% or 100% identical to the sequence provided in one or more of the GenBank Accession Nos. above. In yet other embodiments, the NR4 agent is the nucleic acids encoding any of the NR4 polypeptides described herein or their transcription active domains or the vector comprising these nucleic acids. In specific embodiments, the NR4 agent is a Nurr1 agent.

c-Fos Agents.

In some embodiments, the ND factor is a c-Fos agent. In certain embodiments, the c-Fos agent is a c-Fos polypeptide. c-Fos polypeptides are members of the immediate early gene family of transcription factors, characterized by a leucine-zipper DNA binding domain and a transactivation domain at the C-terminus. The terms "c-Fos gene product," "c-Fos gene peptide," and "c-Fos protein," are used interchangeably herein to refer to native sequence c-Fos polypeptides, polypeptide variants, polypeptide fragments, and chimeric c-Fos polypeptides that can modulate transcription. In certain embodiments, the c-Fos polypeptide is at least 50%, 55%, 60%, 65%, 70%, 75%, 80%, 85%, 90%, 91%, 92%, 93%, 94%, 95%, 96%, 97%, 98%, 99% or 100% identical to the native c-Fos polypeptide sequence (GenBank Accession Nos. NM_005252.3 and NP_005243.1). In yet other embodiments, the c-Fos agent is the nucleic acids encoding any of the c-Fos polypeptides described herein or their transcription active domains or the vector comprising these nucleic acids.

Early B Cell Factor (EBF) Agents.

In some embodiments, the ND factor is an Early B Cell Factor (EBF) agent. In certain embodiments, the EBF agent is an EBF polypeptide. EBF polypeptides and are members of zinc-binding transcription factors that can form homo- and heterodimers that bind to DNA at specific sites that include the sequence 5'-ATTCCCNNGGGAATT-3'. The terms "EBF gene product," "EBF gene peptide," and "EBF protein," are used interchangeably herein to refer to native sequence EBF polypeptides, polypeptide variants, polypeptide fragments, and chimeric EBF polypeptides that can modulate transcription. Native sequence EBF polypeptides include, but are not limited to, EBF1 (e.g., GenBank Accession Nos. NM_024007.3 and NP_076870.1), EBF2 (e.g., GenBank Accession Nos. NM_0022659.3 and NP_073150.2), and EBF3 (e.g., GenBank Accession Nos. NM_001005463.2 and NP_001005463.1). In certain embodiments, the EBF polypeptide is at least 50%, 55%, 60%, 65%, 70%, 75%, 80%, 85%, 90%, 91%, 92%, 93%, 94%, 95%, 96%, 97%, 98%, 99% or 100% identical to the sequence provided in one or more of the GenBank Accession Nos. above. In yet other embodiments, the EBF agent is the nucleic acids encoding any of the EBF polypeptides described herein or their transcription active domains or the vector comprising these nucleic acids. In specific embodiments, the EBF agent is an EBF1 agent.

In some embodiments, the one or more ND factors are provided as nuclear acting polypeptides. In other words, the target cells are contacted with ND polypeptides that act in the nucleus.

To promote transport of ND polypeptides across the cell membrane, ND polypeptide sequences may be fused to a polypeptide permeant domain. A number of permeant domains are known in the art and may be used in the nuclear acting ND polypeptides provided herein, including peptides, peptidomimetics, and non-peptide carriers. For example, a permeant peptide may be derived from the third alpha helix of *Drosophila melanogaster* transcription factor Antennapaedia, referred to as penetratin. As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, e.g., Futaki et al. *Curr Protein Pept Sci.* 4(2): 87-96 (2003); and Wender et al. *Proc. Natl. Acad. Sci. U.S.A* 97(24): 13003-8 (2000); published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002).

The ND polypeptides may be prepared by in vitro synthesis, using conventional methods known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like. Other methods of preparing polypeptides in a cell-free system include, for example, those methods taught in U.S. Application Ser. No. 61/271,000, which is incorporated herein by reference.

The ND polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein. ND polypeptides may be produced recombinantly not only directly, but also as a fusion polypeptide with a heterologous polypeptide, e.g., a polypeptide having a specific cleavage site at the N-terminus of the mature protein or polypeptide. Expression vectors usually contain a selection gene, also termed a selectable marker. This gene encodes a protein necessary for the survival or growth of transformed host cells grown in a selective culture medium.

Following purification by commonly known methods in the art, ND polypeptides are provided to the target cells by standard protein transduction methods. In some cases, the protein transduction method includes contacting cells with a composition containing a carrier agent and at least one purified ND polypeptide. Examples of suitable carrier agents and methods for their use include, but are not limited to, commercially available reagents such as CHARIOT™ (Active Motif, Inc., Carlsbad, Calif.), described in U.S. Pat. No. 6,841,535; BIOPORT™ (Gene Therapy Systems, Inc., San Diego, Calif.); GenomeONE (Cosmo Bio Co., Ltd., Tokyo, Japan); and PROTEOJUICE™ (Novagen, Madison, Wis.); or nanoparticle protein transduction reagents as described in, e.g., U.S. patent application Ser. No. 10/138,593.

In other embodiments, the one or more ND factors are nucleic acids encoding ND polypeptides, i.e. ND nucleic acids. Vectors used for providing ND nucleic acids to the target cells will typically comprise suitable promoters for driving the expression, that is, transcriptional activation, of the nucleic acids. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by at least about 10-fold, by at least about 100-fold, more usually by at least about 1000-fold. In addition, vectors used for providing the nucleic acids may include genes that must later be removed, e.g., using a recombinase system such as Cre/Lox, or the cells that express them destroyed, e.g., by including genes that allow selective toxicity such as herpesvirus TK, bcl-xs, etc ND nucleic acids may be provided directly to the target cells. In other words, the cells are contacted with vectors comprising ND nucleic acids such that the vectors are taken up by the cells. Methods for contacting cells with nucleic acid vectors, such as electroporation, calcium chloride transfection, and lipofection, are well known in the art. Vectors that deliver nucleic acids in this manner are usually maintained episomally, e.g., as plasmids or minicircle DNAs.

Alternatively, the nucleic acid may be provided to the target cells via a virus. In other words, the cells are contacted with viral particles comprising the ND nucleic acids. Retroviruses, for example, lentiviruses, are particularly suitable to such methods. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein to be incorporated into the capsid, this envelope protein determining the specificity of the viral particle for the cells. Envelope proteins are of at least three types, ecotropic, amphotropic and xenotropic. Retroviruses packaged with ecotropic envelope protein, e.g., MMLV, are capable of infecting most murine and rat cell types, and are generated by using ecotropic packaging cell lines such as BOSC23 (Pear et al. (1993) P.N.A.S. 90:8392-8396). Retroviruses bearing amphotropic envelope protein, e.g., 4070A (Danos et al, supra.), are capable of infecting most mammalian cell types, including human, dog and mouse, and are generated by using amphotropic packaging cell lines such as PA12 (Miller et al. (1985) Mol. Cell. Biol. 5:431-437); PA317 (Miller et al. (1986) Mol. Cell. Biol. 6:2895-2902); GRIP (Danos et al. (1988) PNAS 85:6460-6464). Retroviruses packaged with xenotropic envelope protein, e.g., AKR env, are capable of infecting most mammalian cell types, except murine cells. The appropriate packaging cell line may be used to ensure that the target cells are targeted by the packaged viral particles. Methods of introducing the retroviral vectors comprising ND nucleic acids into packaging cell lines and of collecting the viral particles that are generated by the packaging lines are well known in the art.

In another aspect, provided herein is a neuron differentiation (ND) cocktail comprising two or more of the ND factors provided herein. In certain embodiments, the neuron transdifferentiation cocktail comprises 2, 3, or 4 of the ND factors described herein.

In certain embodiments, the ND cocktail comprises two ND factors. In certain embodiments, the ND cocktail comprises an Lmx agent and an NR agent. In other embodiments, the ND cocktail comprises an Lmx agent and a c-Fos agent. In other embodiments, the ND cocktail comprises an Lmx agent and an EBF agent. In some embodiments, the ND cocktail comprises an NR agent and a c-Fos agent. In other embodiments, the ND cocktail comprises an NR agent and an EBF agent. In yet other embodiments, the ND cocktail comprises a c-Fos agent and an EBF agent.

In certain embodiments, the ND cocktail comprises three ND factors. In certain embodiments, the ND cocktail comprises an Lmx agent, an NR agent and a c-Fos agent. In other embodiments, the ND cocktail comprises an Lmx agent, an NR agent and an EBF agent. In other embodiments, the ND cocktail comprises an Lmx agent, a c-Fos agent and an EBF agent. In yet other embodiments, the ND cocktail comprises an NR agent, a c-Fos agent and an EBF agent.

In certain embodiments, the ND cocktail comprises four ND factors. In certain embodiments, the ND cocktail comprises an Lmx agent, an NR agent, a c-Fos agent and an EBF agent. In specific embodiments, the ND cocktail comprises an Lmx1b agent, a Nurr1 agent, a c-Fos agent, and an EBF1 agent. Such an ND cocktail can advantageously promote the differentiation of a target cell (e.g., a somatic cell or a pluripotent cell) to a neuron (e.g., a dopaminergic neuron).

In certain embodiments, the ND cocktail is a neuron transdifferentiation (NT) cocktail that can advantageously promote the transdifferentiation of a target somatic cell (e.g., a non-neuronal somatic cell) to a neuron (e.g., a dopaminergic neuron). In certain embodiments, the NT cocktail comprises four ND factors. In certain embodiments, the NT cocktail comprises an Lmx agent, an NR agent, a c-Fos agent and an EBF agent. In specific embodiments, the NT cocktail comprises an Lmx1 b agent, a Nurr1 agent, a c-Fos agent, and an EBF1 agent.

When more than one ND factor is provided, the ND factors may be provided individually or as a single composition, that is, as a premixed composition, of factors (e.g., the ND cocktails described herein). The ND factors may be added to the target cells simultaneously or sequentially at different times. ND factors may be provided to somatic cells (e.g., a non-neuronal somatic cell, such as a fibroblast) individually or as a single composition, that is, as a premixed composition, of NDs (i.e. a cocktail). The factors may be provided at the same molar ratio or at different molar ratios. The factors may be provided once or multiple times in the course of culturing the cells of the subject invention. For example, the agent(s) may be provided to the target cells one or more times and the cells allowed to incubate with the agents for some amount of time following each contacting event, e.g., 16-24 hours, after which time the media is replaced with fresh media and the cells are cultured further.

Neuron Differentiation (ND) System

Provided herein are neuron differentiation (ND) systems for the differentiation of target cells (e.g., somatic cells or pluripotent cells) to neurons. In some embodiments, the ND system comprises one or more ND factors (e.g., a ND cocktail). In certain embodiments, the ND system comprises one or more ND factors (e.g., a ND cocktail), together with other agents that promote the survival of the induced neuron.

In certain embodiments, the ND system is a neuron transdifferentiation (NT) system that allows for the transdifferentiation of target somatic cells to neurons. Such an NT system does not require induced pluripotent stem cell reprogramming factors as they are known in the art, e.g., Oct 3/4, Sox2, KLF4, Myc, Nanog, or Lin28; or culture conditions developed in the art for culturing pluripotent stem cells, e.g., culture in hanging droplets. In a specific embodiment, the NT system is a dopaminergic neuron transdifferentiation system comprising one or more NT factors to promote the transdifferentiation of somatic cells to dopaminergic neurons.

In addition to the one or more ND factors (e.g., an ND cocktail or NT cocktail as described herein), in some embodiments, the ND system may also include other reagents. For example, the ND system may include one or more agents known in the art to promote cell reprogramming. Examples of agents known in the art to promote cell reprogramming include GSK-3 inhibitors (e.g., CHIR99021 and the like (see, e.g., Li, W. et al. (2009) Stem Cells, Epub Oct. 16, 2009)); histone deacetylase (HDAC) inhibitors (e.g., those described in US20090191159, the disclosure of which is incorporated herein by reference); histone methyltransferase inhibitors (e.g., G9a histone methyltransferase inhibitors, e.g., BIX-01294, and the like (see, e.g., Shi, Y et al. (2008) Cell Stem Cells 3(5):568-574)); agonists of the dihydropyridine receptor (e.g., BayK8644, and the like (see, e.g., Shi, Y et al. (2008) Cell Stem Cell 3(5):568-574)); and inhibitors of TGFβ signaling (e.g., RepSox and the like (see, e.g., Ichida, J K. et al. (2009) Cell Stem Cell 5(5):491-503)).

Examples of agents known in the art to promote cell reprogramming also include agents that reduce the amount of methylated DNA in a cell, for example by suppressing DNA methylation activity in the cell or promoting DNA demethylation activity in a cell. Examples of agents that suppress DNA methylation activity include, e.g., agents that inhibit DNA methyltransferases (DNMTs), e.g., 5-aza-cytidine, 5-aza-2'-deoxycytidine, MG98, S-adenosyl-homocysteine (SAH) or an analogue thereof (e.g., periodate-oxidized adenosine or 3-deazaadenosine), DNA-based inhibitors such as those described in Bigey, P. et al (1999) J. Biol. Chem. 274:459-44606, antisense nucleotides such as those described in Ramchandani, S et al, (1997) Proc. Natl. Acad. Sci. USA 94: 684-689 and in Fournel, M et al, (1999) J. Biol. Chem. 274:24250-24256, or any other DNMT inhibitor known in the art. Examples of agents that promote DNA demethylation activity include, e.g., cytidine deaminases, e.g., AID/APOBEC agents (Bhutani, N et al. (2009) Nature. December 21. [Epub ahead of print]; Rai, K. et al. (2008) Cell 135:1201-1212), agents that promote G:T mismatch-specific repair activity, e.g., Methyl binding domain proteins (e.g., Mbp4) and thymine-DNA glycosylase (TDG) protein (Rai, K. et al. (2008) Cell 135:1201-1212), agents that promote growth arrest and DNA-damage-inducible 45 (GADD45) activity protein (Rai, K. et al. (2008) Cell 135:1201-1212), and the like.

Other reagents of interest for optional inclusion in the ND system are agents that inhibit proliferation, e.g., AraC.

Other reagents of interest for optional inclusion in the ND system are agents known in the art to promote the differentiation of neuronal precursors into particular neuronal subtypes. For example, to promote differentiation into excitatory (glutamatergic) neurons, cells may also be contacted with Tlx polypeptides or nucleic acids encoding these polypeptides (e.g., Cheng, L. et al. (2004) Nat. Neurosci. 7(5): 510-517). To promote differentiation into inhibitory (GABAergic) neurons, cells may also be contacted with Lbx1 polypeptides or nucleic acids encoding these polypeptides (e.g., Cheng, L. et al. (2005) Nature Neuroscience 8(11):1510-1515). To promote differentiation into dopaminergic (DA) neurons, cells may also be co-cultured with a PA6 mouse stromal cell line under serum-free conditions, see, e.g., Kawasaki et al., (2000) Neuron, 28(1):3140. To promote differentiation into cholinergic neurons, cells may also be contacted with Lhx8 polypeptides or nucleic acids encoding these polypeptides (Manabe, T. et al. (2007) Cell Death and Differentiation 14: 1080-1085). To promote differentiation of spinal cord motor neurons, cells may also be contacted with Mnx1 (Hb9) (Wichterle, H et al. (2002) Cell 110(3):385-397). To promote differentiation into corticospinal projection neurons, e.g., motor neurons, cells may also be contacted with Fezf2 or Ctip2 polypeptides or nucleic acids encoding those polypeptides (e.g., Molyneaux et al. (2005) Neuron 47(6):817-31; Chen et al. (2008) Proc Natl Acad Sci USA 105(32):11382-7). To promote differentiation of corticocortical projection neurons, e.g., callosal neurons, cells may be contacted with Satb2 polypeptides or nucleic acids encoding those polypeptides (e.g., Alcamo et al. (2008) Neuron 57(3):364-77; Britanova et al. (2008) Neuron 57(3):378-92). To promote differentiation of corticothalamic neurons, cells may be contacted with Sox5 polypeptides or nucleic acids encoding those polypeptides (e.g., Lai et al. (2008) Neuron 57(2):232-47). Other methods have also been described, see, e.g., Pomp et al., (2005), Stem Cells 23(7): 923-30; U.S. Pat. No. 6,395,546, e.g., Lee et al., (2000), Nature Biotechnol., 18:675-679.

Reagents in the ND system may be provided in any culture media known in the art to promote cell survival, e.g., DMEM, Iscoves, Neurobasal media, etc. In some cases, the media will be DMEM. In some cases, with media will be N3. Media may be supplemented with agents that inhibit the growth of bacterial or yeast, e.g., penicillin/streptomycin, a fungicide, etc., with agents that promote health, e.g., glutamate, and other agents typically provided to culture media as are known in the art of tissue culture.

Non-ND factor reagents of the ND system, e.g., agents that promote demethylation, agents that promote the survival and/or differentiation of neurons or subtypes of neurons, agents that inhibit proliferation, and the like, may be provided to the cells prior to providing the ND factors. Alternatively, they may be provided concurrently with providing the ND factors. Alternatively, they may be provided subsequently to providing the ND factors.

ND systems provided herein may be used for the differentiation of a target cell to a neuron (induced neuron) or for the differentiation of a particular neuron subtype to another neuron subtype In specific embodiments, the ND systems provided herein may be used for the transdifferentiation of a target somatic cell to a neuron (induced neuron) or for the transdifferentiation of a particular neuron subtype to another neuron subtype (i.e. a neuron transdifferentiation system). In certain embodiments, the target cell is somatic cell. In particular embodiments, the target cell is a non-neuronal somatic cell. In specific embodiments, the target cell is a fibroblast. In other embodiments, the target cell is a non-somatic cell. In specific embodiments, the target cell is a pluripotent cell. In yet other embodiments, the target cell is a neuronal cell of a particular subtype.

The target cells may be from any mammal, including humans, primates, domestic and farm animals, and zoo, laboratory or pet animals, such as dogs, cats, cattle, horses, sheep, pigs, goats, rabbits, rats, mice etc. They may be established cell lines or they may be primary cells, where "primary cells", "primary cell lines", and "primary cultures" are used interchangeably herein to refer to cells and cells cultures that have been derived from a subject and allowed to grow in vitro for a limited number of passages. In certain embodiments, the target cell is a human cell.

The target cell may be isolated from fresh or frozen cells, which may be from a neonate, a juvenile or an adult, and from tissues including skin, muscle, bone marrow, peripheral blood, umbilical cord blood, spleen, liver, pancreas, lung, intestine, stomach, adipose, and other differentiated tissues. The tissue may be obtained by biopsy or aphoresis from a live donor, or obtained from a dead or dying donor within about 48 hours of death, or freshly frozen tissue, tissue frozen within about 12 hours of death and maintained at below about −20° C., usually at about liquid nitrogen temperature (−190° C.) indefinitely. For isolation of cells from tissue, an appropriate solution may be used for dispersion or suspension. Such solution will generally be a balanced salt solution, e.g., normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

In some embodiments, a NT system is provided for the transdifferentiation of a target cell (e.g., a non-neuronal somatic cell) to a neuron (induced neuron). Non-neuronal somatic target cells include any somatic cell that would not give rise to a neuron in the absence of experimental manipulation. Examples of non-neuronal target somatic cells include differentiating or differentiated cells from ectodermal (e.g., keratinocytes), mesodermal (e.g., fibroblast), endodermal (e.g., pancreatic cells), or neural crest lineages (e.g., melanocytes). The somatic cells may be, for example, fibroblasts pancreatic beta cells, oligodendrocytes, astrocytes, hepatocytes, hepatic stem cells, cardiomyocytes, skeletal muscle cells, smooth muscle cells, hematopoietic cells, osteoclasts, osteoblasts, pericytes, vascular endothelial cells, schwann cells, and the like. They may be terminally differentiated cells, or they may be capable of giving rise to cells of a specific, non-neuronal lineage, e.g., cardiac stem cells, hepatic stem cells, and the like. In specific embodiments, the target cell is a terminally differentiated non-neuronal somatic cell. The somatic cells are readily identifiable as non-neuronal by the absence of neuronal-specific markers that are well-known in the art, as described above. In a specific embodiment, the target cell is a fibroblast.

In certain embodiments, a NT system is provided for the transdifferentiation of a neuron of a particular subtype (the target cell) to a neuron of another subtype (induced neuron). In certain embodiments, the target cell is a glutamatergic neuron. In other embodiments, the target cell is an inhibitory (GABAergic) neuron. In yet other embodiments, the target cell is a dopaminergic (DA) neuron.

In Vitro Methods of Conversion, and Uses for Cells Converted In Vitro

In some embodiments, a target cell (e.g., a non-neuronal somatic cell) is contacted in vitro with the ND system comprising one or more ND factors. Any target cell can be used, including, but not limited to, the target cells described herein.

Cells contacted in vitro with the ND system of reagents, i.e. the one or more ND factors (ND cocktail) and optionally the one or more other agents that promote reprogramming and promote the growth and/or differentiation of neurons, and the like, may be incubated in the presence of the reagent(s) for about 30 minutes to about 24 hours, e.g., 1 hours, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the target cells one or more times, e.g., one time, twice, three times, or more than three times, and the cells allowed to incubate with the agent(s) for some amount of time following each contacting event e.g., 16-24 hours, after which time the media is replaced with fresh media and the cells are cultured further.

After contacting the target cell with the ND system, the target cell may be cultured so as to promote the survival and differentiation of neurons. Methods and reagents for culturing cells to promote the growth of neurons or particular subtypes of neurons and for isolating neurons or particular subtypes of neurons are well known in the art, any of which may be used in the present invention to grow and isolate the induced neuronal cells. For example, the target cells (either pre- or post-contacting with the ND factors/ND cocktail) may be plated on Matrigel or other substrate as known in the art. The target cells may be cultured in media such as N3, supplemented with factors. Alternatively, the target cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or stromal cells associated with neuronal survival and differentiation.

The effective amount of a ND system that may used to contact a target cell is an amount that induces at least 0.01% of the cells of the culture to increase expression of one or more genes known in the art to become more highly expressed upon the acquisition of a neuronal fate, e.g., Tau, Tuj1, MAP2, NeuN, and the like. An effective amount is the amount that induces an increase in expression of these genes that is about 1.5-fold or more, e.g., 1.5 fold, 2 fold, 3 fold, 4 fold, about 6 fold, about 10 fold greater than the level of expression observed in the absence of the ND system. The level of gene expression can be readily determined by any convenient method, e.g., by measuring RNA levels, e.g., by RT-PCR, quantitative RT-PCR, Northern blot, etc., or by measuring protein levels, e.g., Western blot, ELISA, fluorescence activated cell sorting, etc.

It is noted here that the target cells do not need to be cultured under methods known in the art to promote pluripotency in order to be converted into induced neurons. By pluripotency, it is meant that the cells have the ability to differentiate into all types of cells in an organism. In other words, the methods of the present invention do not require that the target cells (e.g., somatic cells) of the present invention be provided with reprogramming factors known in the art to reprogram target cells to become pluripotent stem cells, i.e. iPS cells, e.g., Oct3/4, SOX2, KLF4, MYC, Nanog, or Lin28, and be cultured under conditions known in the art to promote pluripotent stem cell induction, e.g., as hanging droplets, in order for the target cells to be transdifferentiated into induced neurons.

Following the methods provided herein, the target cell (e.g., a non-neuronal somatic cell or pluripotent cell) will be converted into an induced neuron at an efficiency of differentiation/efficiency of conversion that is at least about 0.01% of the total number of target somatic cells cultured initially, e.g., 0.01%, 0.05%, 0.1%, 0.5%, 1%, 2%, 3%, 4%, 5%, 6%, 7%, 8%, 9%, 10%, 12%, 14%, 16%, 20% or more. At times, depending on the age of the donor, the origin of the tissue, or the culture conditions, higher efficiencies may be achieved. This efficiency of differentiation is an enhanced efficiency over that which may be observed in the absence of ND factor(s). In other words, target cells and cell cultures have an enhanced ability to give rise to the desired type of cell when contacted with one or more ND factor(s) relative to cells that were not contacted with the ND factors. By enhanced, it is meant that the target cell cultures have the ability to give rise to the desired cell type that is 150% or greater than the ability of a somatic cell culture that was not contacted with the ND factor(s), e.g., 150%, 200%, 300%, 400%, 600%, 800%, 1000%, or 2000% of the ability of the uncontacted population. In other words, the culture of target cells produces about 1.5 fold, about 2-fold, about 3-fold, about 4-fold, about 6-fold, about 10-fold, about 20-fold, about 30-fold, about 50-fold, about 100-fold, about 200-fold the number of induced neurons that are produced by a population of target cells that are not contacted with the ND factor(s). The efficiency of differentiation may be determined by assaying the number of neurons that develop in the cell culture, e.g., by assaying the number of cells that express genes that are expressed by neurons, e.g., Pitx3, En2, TH, VMAT2, DAT, cRET, Msx1, Ngn2, Foxa2, MASH1, PSD-95, Tau, Tuj1, MAP2, and/or NeuN, and/or the number of cells that being to extend processes and make synaptic connections. In some embodiments, the method produces an enriched culture of induced neurons, comprising at least about 80% induced neurons, more usually at least 90% induced neurons and may be 95% induced neurons.

Induced neurons produced by the above in vitro methods may be used in cell replacement therapy to treat diseases. Specifically, induced neurons may be transferred to subjects suffering from a wide range of diseases or disorders with a neuronal component, i.e. with neuronal symptoms, for example to reconstitute or supplement differentiating or differentiated neurons in a recipient.

The therapy may be directed at treating the cause of the disease; or alternatively, the therapy may be to treat the effects of the disease or condition. For example, the therapy may be directed at replacing neurons whose death caused the disease, e.g., motor neurons in Amyotrophic lateral sclerosis (ALS), or the therapy may be directed at replacing neurons that died as a result of the disease, e.g., photoreceptors in age related macular degeneration (AMD).

The induced neuron may be transferred to, or close to, an injured site in a subject; or the cells can be introduced to the subject in a manner allowing the cells to migrate, or home, to the injured site. The transferred cells may advantageously replace the damaged or injured cells and allow improvement in the overall condition of the subject. In some instances, the transferred cells may stimulate tissue regeneration or repair.

In some embodiments, the induced neurons produced by the methods described herein are further enriched i.e. the induced neuron or a sub-population of induced neuron may be purified or isolated from the rest of the cell culture, for example, prior to transferring to a subject in need thereof. In certain embodiments, the method further comprises the step of enriching the induced neurons to produce an enriched culture of induced neurons. In other words, one or more steps may be executed to further enrich for the induced neurons or a subpopulation of induced neurons, i.e. to provide an enriched population of induced neurons or sub-population of induced neurons. In some cases, one or more antibodies specific for a marker of cells of the neuronal lineage or a marker of a sub-population of cells of the neuronal lineage are incubated with the cell population and those bound cells are isolated. In other cases, the induced neurons or a sub-population of the induced neurons express a marker that is a reporter gene, e.g., EGFP, dsRED, lacz, and the like, that is under the control of a neuron-specific promoter or neuron-subtype specific promoter, e.g., Tau, GABA, NMDA, and the like, which is then used to purify or isolate the induced neurons or a subpopulation thereof.

By a marker it is meant that, in cultures comprising target cells that have been transdifferentiated to become an induced neuron, the marker is expressed only by the cells of the culture that will develop, are developing, and/or have developed into neurons. It will be understood by those of skill in the art that the stated expression levels reflect detectable amounts of the marker protein on or in the cell. A cell that is negative for staining (the level of binding of a marker-specific reagent is not detectably different from an isotype matched control) may still express minor amounts of the marker. And while it is commonplace in the art to refer to cells as "positive" or "negative" for a particular marker, actual expression levels are a quantitative trait. The number of molecules on the cell surface can vary by several logs, yet still be characterized as "positive".

Cells of interest, i.e. cells expressing the marker of choice, may be enriched for, that is, separated from the rest of the cell population, by a number of methods that are well known in the art. For example, flow cytometry, e.g., fluorescence activated cell sorting (FACS), may be used to separate the cell population based on the intrinsic fluorescence of the marker, or the binding of the marker to a specific fluorescent reagent, e.g., a fluorophor-conjugated antibody, as well as other parameters such as cell size and light scatter. In other words, selection of the cells may be effected by flow cytometry. Although the absolute level of staining may differ with a particular fluorochrome and reagent preparation, the data can be normalized to a control. To normalize the distribution to a control, each cell is recorded as a data point having a particular intensity of staining. These data points may be displayed according to a log scale, where the unit of measure is arbitrary staining intensity. In one example, the brightest stained cells in a sample can be as much as 4 logs more intense than unstained cells. When displayed in this manner, it is clear that the cells falling in the highest log of staining intensity are bright, while those in the lowest intensity are negative. The "low" positively stained cells have a level of staining above the brightness of an isotype matched control, but are not as intense as the most brightly staining cells normally found in the population. An alternative control may utilize a substrate having a defined density of marker on its surface, for example a fabricated bead or cell line, which provides the positive control for intensity.

Other methods of separation, i.e. methods by which selection of cells may be effected, based upon markers include, for example, magnetic activated cell sorting (MACS), immunopanning, and laser capture microdissection.

Examples of induced neuron makers that can be used in the methods described herein include, but are not limited to, TH, DAT, VMAT2, PSD-95 and Tuj-1.

Another example of a protein of interest that may be used as a marker in the present invention is PSA-NCAM. PSA-NCAM is an NCAM polypeptide (GenBank Accession Nos. NM_000615.5 (isoform 1), NM_181351.3 (isoform 2) and NM_001076682.2 (isoform 3)) that is post-translationally modified by the addition of poly-sialic acid. A number of antibodies that are specific for PSA-NCAM are known in the art, including, e.g., anti-PSA-NCAM Clone 2-2B antibody (Millipore).

Another example of a marker that may be used is a fluorescent protein, e.g., GFP, RFP, dsRED, etc., operably linked to a neuron-specific promoter, e.g., Tau, PSA-NCAM, etc. In such embodiments, the marker and promoter are provided to the cell as an expression cassette on a vector, e.g., encoded on a DNA plasmid, encoded in a virus, and the like, The expression cassette may optionally contain other elements, e.g., enhancer sequences, other proteins for expression in the cell, and the like. In some embodiments, the expression cassette is provided to the cell prior to contacting the cell with ND factors, i.e. while the cell is still a somatic cell. In some embodiments, the expression cassette is provided to the cell at the same time as the target cell is contacted with the ND factor. In some embodiments, the expression cassette is provided to the cell after the cell is contacted with the ND factors.

Enrichment of the induced neuron population or a subpopulation of induced neurons may be performed about 3 days or more after contacting the target cells with the ND factors of the ND system, e.g., 3 days, 4 days, 5 days, 6 days, 7 days, 10 days, 14 days, or 21 days after contacting the target cells with the ND factors. Populations that are enriched by selecting for the expression of one or more markers will usually have at least about 80% cells of the selected phenotype, more usually at least 90% cells and may be 95% of the cells, or more, of the selected phenotype.

In some cases, genes may be introduced into the target cells or the cells derived therefrom, i.e. induced neuron, prior to transferring to a subject for a variety of purposes, e.g., to replace genes having a loss of function mutation, provide marker genes, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to introduce nucleic acids into the target cells, e.g., electroporation, calcium precipitated DNA, fusion, transfection, lipofection, infection and the like, as discussed above. The particular manner in which the DNA is introduced is not critical to the practice of the methods provided herein.

To prove that one has genetically modified the target cells or the cells derived therefrom, i.e induced neuron, various techniques may be employed. The genome of the cells may be restricted and used with or without amplification. The polymerase chain reaction; gel electrophoresis; restriction analysis; Southern, Northern, and Western blots; sequencing; or the like, may all be employed. The cells may be grown under various conditions to ensure that the cells are capable of maturation to all of the neuronal lineages while maintaining the ability to express the introduced DNA. Various tests in vitro and in vivo may be employed to ensure that the neuronal phenotype of the derived cells has been maintained.

Subjects in need of neuron replacement therapy, e.g., a subject suffering from a neurological condition associated with the loss of neurons or with aberrantly functioning neurons, could especially benefit from therapies that utilize cells derived by the methods provided herein. Examples of such diseases, disorders and conditions include neurodegenerative diseases (e.g., Parkinson's Disease, Alzheimer's Disease, Huntington's Disease, Amyotrophic Lateral Sclerosis (ALS), Spielmeyer-Vogt-Sjögren-Batten disease (Batten Disease), Frontotemporal Dementia with Parkinsonism, Progressive Supranuclear Palsy, Pick Disease, prion diseases (e.g., Creutzfeldt-Jakob disease), Amyloidosis, glaucoma, diabetic retinopathy, age related macular degeneration (AMD), and the like); neuropsychiatric disorders (e.g., anxiety disorders (e.g., obsessive compulsive disorder), mood disorders (e.g., depression), childhood disorders (e.g., attention deficit disorder, autistic disorders), cognitive disorders (e.g., delirium, dementia), schizophrenia, substance related disorders (e.g., addiction), eating disorders, and the like); channelopathies (e.g., epilepsy, migraine, and the like); lysosomal storage disorders (e.g., Tay-Sachs disease, Gaucher disease, Fabry disease, Pompe disease, Niemann-Pick disease, Mucopolysaccharidosis (MPS) & related diseases, and the like); autoimmune diseases of the CNS (e.g., Multiple Sclerosis, encephalomyelitis, paraneoplastic syndromes (e.g., cerebellar degeneration), autoimmune inner ear disease, opsoclonus myoclonus syndrome, and the like); cerebral infarction, stroke, and spinal cord injury.

In some approaches, the reprogrammed target cells, i.e. induced neuron may be transplanted directly to an injured site to treat a neurological condition, see, e.g., Morizane et al., (2008), Cell Tissue Res., 331(1):323-326; Coutts and Keirstead (2008), Exp. Neurol., 209(2):368-377; Goswami and Rao (2007), Drugs, 10(10):713-719. For example, for the treatment of Parkinson's disease, induced dopaminergic neurons may be transplanted directly into the striate body of a subject with Parkinson's disease. As another example, for treatment of ALS, corticospinal motor neurons may be transplanted directly into the motor cortex of the subject with ALS. In other approaches, the cells derived by the methods of the invention are engineered to respond to cues that can target their migration into lesions for brain and spinal cord repair; see, e.g., Chen et al. (2007) Stem Cell Rev. 3(4):280-288. In one aspect, provided herein is a method of treatment of Parkinson's Disease in a subject comprising transplanting an induced dopaminergic neuron into the striate body of the subject.

The induced neurons may be administered in any physiologically acceptable medium. They may be provided prior to differentiation, i.e. they may be provided in an undifferentiated state and allowed to differentiate in vivo, or they may be allowed to differentiate for a period of time ex vivo and provided following differentiation. They may be provided alone or with a suitable substrate or matrix, e.g., to support their growth and/or organization in the tissue to which they are being transplanted. Usually, at least $1\times10^5$ cells will be administered, preferably $1\times10^6$ or more. The cells may be introduced to the subject via any of the following routes: parenteral, intravenous, intracranial, intraspinal, intraocular, or into spinal fluid. The cells may be introduced by injection, catheter, or the like. Examples of methods for local delivery, that is, delivery to the site of injury, include, e.g., through an Ommaya reservoir, e.g., for intrathecal delivery (see, e.g., U.S. Pat. Nos. 5,222,982 and 5,385,582, incorporated herein by reference); by bolus injection, e.g., by a syringe, e.g., intravitreally or intracranially; by continuous infusion, e.g., by cannulation, e.g., with convection (see, e.g., US Application No. 20070254842, incorporated here by reference); or by implanting a device upon which the cells have been reversably affixed (see, e.g., US Application Nos. 20080081064 and 20090196903, incorporated herein by reference).

The number of administrations of treatment to a subject may vary. Introducing the induced neurons into the subject may be a one-time event; but in certain situations, such treatment may elicit improvement for a limited period of time and require an on-going series of repeated treatments. In other situations, multiple administrations of the iNs may be required before an effect is observed. The exact protocols depend upon the disease or condition, the stage of the disease and parameters of the individual subject being treated.

Additionally or alternatively, induced neurons produced by the above in vitro methods may be used as a basic research or drug discovery tool, for example to evaluate the phenotype of a genetic disease, e.g., to better understand the etiology of the disease, to identify target proteins for therapeutic treatment, to identify candidate agents with disease-modifying activity, i.e. an activity in modulating the survival or function of neurons in a subject suffering from a neurological disease or disorder, e.g., to identify an agent that will be efficacious in treating the subject. For example, a candidate agent may be added to a cell culture comprising induced neurons derived from the subject's somatic cells, and the effect of the candidate agent assessed by monitoring output parameters such as induced neuron survival, the ability of the induced neuron to become depolarized, the extent to which the induced neurons form synapses, and the like, by methods described herein and in the art.

In another aspect, provided herein is a method of screening for candidate agents for the treatment of Parkinson's Disease comprising contacting a induced neuron with a candidate agent, wherein the neuron is derived from a target cell (e.g., non-neuronal somatic cell) of a subject with Parkinson's Disease; and assessing one or more parameters of the neuron.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g., mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values. In specific embodiments, the parameter is the amount of mitochondrial bound RNA in the induced neuron. In some embodiments, the parameter is the amount of mitochondrial-bound RNA in the neuron cell; the distribution and morphology of mitochondria in the processes of the neuron; or the ATP levels of the neurons.

Candidate agents of interest may include antibodies, polypeptides and small molecules. Candidate agents of interest for screening may include known and unknown compounds that encompass numerous chemical classes, primarily organic molecules, which may include organometallic molecules, inorganic molecules, genetic sequences, etc. An important aspect of the methods provided herein is to evaluate candidate drugs, including toxicity testing, and the like.

Candidate agents may include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents are screened for biological activity by adding the agent to one or a plurality of cell samples, usually in conjunction with cells lacking the agent. The change in parameters in response to the agent is measured, and the result evaluated by comparison to reference cultures, e.g., in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

In Vivo Methods of Conversion, and Uses for Cells Converted In Vivo

In some embodiments, a target cell (e.g., a non-neuronal somatic cell) is contacted in vivo with the ND system comprising ND factor(s), (e.g., any of the ND cocktails as provided herein) in a subject in need of neuron replacement therapy. Cells in vivo may be contacted with a ND system suitable for pharmaceutical use, i.e. a ND pharmaceutical composition, by any of a number of well-known methods in the art for the administration of polypeptides, nucleic acids, and small molecules to a subject and as discussed above, with respect to PUM1 and SF2 inhibitors. The ND factors can be incorporated into a variety of formulations. More particularly, the ND factors can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the ND pharmaceutical composition can be achieved in various ways, including oral, buccal, rectal, parenteral, intraperitoneal, intradermal, transdermal, intracheal, etc., administration. The ND pharmaceutical composition may be systemic after administration or may be localized by the use of regional administration, intramural administration, or use of an implant that acts to retain the active dose at the site of implantation. The ND pharmaceutical composition may be formulated for immediate activity or they may be formulated for sustained release.

For some central nervous system conditions, it may be necessary to formulate the ND pharmaceutical composition, that is, the ND system comprising one or more ND factors (e.g., ND cocktail), to cross the blood brain barrier (BBB). One strategy for drug delivery through the blood brain barrier (BBB) entails disruption of the BBB, either by osmotic means such as mannitol or leukotrienes, or biochemically by the use of vasoactive substances such as bradykinin. A BBB disrupting agent can be co-administered with the therapeutic compositions when the compositions are administered by intravascular injection. Other strategies to go through the BBB may entail the use of endogenous transport systems, including caveoil-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the invention to facilitate transport across the endothelial wall of the blood vessel. Alternatively, drug delivery of the ND pharmaceutical composition behind the BBB may be by local delivery, for example by intrathecal delivery, e.g., through an Ommaya reservoir (see, e.g., U.S. Pat. Nos. 5,222,982 and 5,385,582, incorporated herein by reference); by bolus injection, e.g., by a syringe, e.g., intravitreally or intracranially; by continuous infusion, e.g., by cannulation, e.g., with convection (see, e.g., US Application No. 20070254842, incorporated here by reference); or by implanting a device upon which the ND pharmaceutical composition has been reversably affixed (see e.g., US Application Nos. 20080081064 and 20090196903, incorporated herein by reference).

The calculation of the effective amount or effective dose of the ND pharmaceutical composition to be administered is within the skill of one of ordinary skill in the art, and will be routine to those persons skilled in the art. Needless to say, the final amount to be administered will be dependent upon the route of administration and upon the nature of the disorder or condition that is to be treated.

For inclusion in a medicament, the ND factors may be obtained from a suitable commercial source. As a general proposition, the total pharmaceutically effective amount of the compound administered parenterally per dose will be in a range that can be measured by a dose response curve.

The ND pharmaceutical composition to be used for therapeutic administration must be sterile. Sterility is readily accomplished by filtration through sterile filtration membranes (e.g., 0.2 μm membranes). Therapeutic compositions generally are placed into a container having a sterile access port, for example, an intravenous solution bag or vial having a stopper pierceable by a hypodermic injection needle. The ND pharmaceutical composition ordinarily will be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The pharmaceutical composition comprising the lyophilized ND factor(s) is prepared by reconstituting the lyophilized compound, for example, by using bacteriostatic Water-for-Injection.

An ND system for pharmaceutical use, i.e. a ND pharmaceutical composition, can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the ND pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The ND pharmaceutical composition can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The effective amount of a therapeutic composition to be given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

Mammalian species that may be treated with the present methods include canines and felines; equines; bovines; ovines; etc. and primates, particularly humans. Animal models, particularly small mammals, e.g., murine, lagomorpha, etc. may be used for experimental investigations.

More particularly, the therapeutic compositions find use in the treatment of subjects, such as human patients, in need of neuron replacement therapy. Examples of such subjects would be subjects suffering from conditions associated with the loss of neurons or with aberrantly functioning neurons. Patients having diseases and disorders characterized by such conditions will benefit greatly by a treatment protocol of the pending claimed invention. Examples of such diseases, disorders and conditions include e.g., neurodegenerative diseases, neuropsychiatric disorders, channelopathies, lysosomal storage disorders, autoimmune diseases of the CNS, cerebral infarction, stroke, and spinal cord injury, as described previously.

An effective amount of an ND pharmaceutical composition is the amount that will result in an increase the number of neurons at the site of injury, and/or will result in measurable reduction in the rate of disease progression in vivo. For example, an effective amount of an ND pharmaceutical composition will inhibit the progression of symptoms e.g., loss of muscle control, loss of cognition, hearing loss, vision loss, etc. by at least about 5%, at least about 10%, at least about 20%, preferably from about 20% to about 50%, and even more preferably, by greater than 50% (e.g., from about 50% to about 100%) as compared to the appropriate control, the control typically being a subject not treated with the ND pharmaceutical composition. An agent is effective in vivo if administration of the agent at about 1 µg/kg to about 100 mg/kg body weight results in inhibition of symptoms within about 1 month to 3 months from the first administration of the pharmaceutical composition. In a specific aspect, body function may be improved relative to the amount of function observed at the start of therapy.

The methods provided herein also find use in combined therapies, e.g., in with therapies that are already known in the art to provide relief from symptoms associated with the aforementioned diseases, disorders and conditions. The combined use of an ND pharmaceutical composition of the present invention and these other agents may have the advantages that the required dosages for the individual drugs is lower, and the effect of the different drugs complementary.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Materials and Methods

The following methods and materials were used in the Examples described below.

Cell Culture.

Human adult skin fibroblasts obtained from control and PD patients (Table 1) were cultured in MEF medium. Fibroblasts were seeded with 50% confluence onto Matrigel-coated (BD Biosciences) cell culture wells and infected with 1.5 µl of each concentrated lentiviral particle containing the coding sequence of each human factor to be tested. The lentiviral particles were mixed with MEF media containing 8 µg/ml polybrene. 24 hours post-infection the medium was replaced with MEF medium containing 2 µg/ml doxycycline to activate the transcription of transduced genes. The medium was gradually changed from MEF medium containing 2 µg/ml doxycycline to N3 medium (DMEM/F-12 medium containing 25 µg/ml insulin, 50 µg/ml transferrin, 30 nM sodium selenite, 20 nM progesterone, 100 nM putrescine, 2 µg/ml doxycycline) (Vierbuchen et al., Direct conversion of fibroblasts to functional neurons by defined factors. Nature 463, 1035-1041 (2010)).

TABLE 1

Description of adult human skin fibroblasts derived from two Parkinson's disease (PD) patients and one control individual.

| Internal ID | Passage # | Mutation | Allele | Gender | Ethnicity |
|---|---|---|---|---|---|
| IMDM-B | 1 | Control | | male | hispanic |
| FDM-A | 1 | PINK1(G309D) | homozygous | male | hispanic |
| EDM | 1 | PINK1(G309D) | homozygous | female | hispanic |

Lentiviral Production, Infection, and Cell Culture.

Replication-incompetent VSVg-coated lentiviral particles were packaged in HEK293T cells. Briefly, for each 15 cm cell culture dish, 22 µg of lentiviral vector containing the inserted human gene, 11 µg and 11 µg VSVg DNA were mixed and co-transfected. 24 hours post-transfection the medium was changed and replaced with fresh growth medium containing 10% FBS. 72 hours later the supernatant was collected and centrifuged at 50,000 g for 2.20 hours at 20° C. The pellet was re-suspended in 150 µl 1×PBS overnight at 4° C., and subsequently frozen as aliquots.

For the infection of in vitro cell cultures, lentiviral particles were mixed with regular growth medium containing 8 µg/ml polybrene and added to the cells. 24 hours post-infection the medium was replaced with fresh cell culture medium.

RT-PCR, CLIP Assay, RNA Binding Assay, and Purification of Mitochondria-Associated RNAs.

For RT-PCR analysis, total RNAs were extracted from in vitro cell cultures, fly heads, fly thoraces, or fly intestinal tissues using an RNeasy® Mini kit (Qiagen), and one-step RT-PCR was performed using an RT-PCR kit (Qiagen). Table 2 lists the DNA oligomers used for RT-PCR.

TABLE 2

DNA oligomers used to perform RT-PCR experiments for selected human and *Drosophila melanogaster* specific genes.

| Oligo name | Sequence (5'-3') | SEQ ID |
|---|---|---|
| I. Human mRNAs | | |
| 5'-Complex V5α | GAGCGTATTCTTGGAGC | SEQ ID NO: 1 |
| 3'-Complex V5α | GCATCAACTACACGACCC | SEQ ID NO: 2 |
| 5'-Complex IV (sub.1) | GATATGGCGTTTCCCCGC | SEQ ID NO: 3 |
| 3'-Complex IV (sub.1) | GATCAGACGAAGAGGGGCG | SEQ ID NO: 4 |
| 5'-Complex I 30kDa | TTGCTGCCGGTGAGGCGGG | SEQ ID NO: 5 |
| 3'-Complex I 30kDa | CAGCAGACTCAATGGGCG | SEQ ID NO: 6 |
| 5'-Mfn2 | TATCAGCGAAGTGCTGCC | SEQ ID NO: 7 |
| 3'-Mfn2 | CAATCCAGCTGTCCAGCTCC | SEQ ID NO: 8 |
| 5'-Actin | GCGGGAAATCGTGCGTGACATT | SEQ ID NO: 9 |
| 3'-Actin | GATGGAGTTGAAGGTAGTTTCGTG | SEQ ID NO: 10 |
| II. Drosophila mRNAs | | |
| Oscp-RT-N | TAAAGAAGCTGGACACCGTG | SEQ ID NO: 11 |
| Oscp-RT-C | ATCAAGAGCAAATCCTTAAGAG | SEQ ID NO: 12 |
| mCoI-RT-N | CCTGGATTTGGAATAATTTCTC | SEQ ID NO: 13 |
| mCoI-RT-C | TCAGAATATCTATGTTCAGCTG | SEQ ID NO: 14 |
| Marf-RT-N | TGGAAGCCACTCCTGTGTG | SEQ ID NO: 15 |
| Marf-RT-C | CACTACTGTTCCACTACTGC | SEQ ID NO: 16 |
| Pink1-RT2-N | GAACATGTCGCGCTTTGTTC | SEQ ID NO: 17 |
| Pink1-RT2-C | TTGATTCTGCAGCAAACGTTC | SEQ ID NO: 18 |
| Rps49 forward | GCACCAAGCACTTCATCC | SEQ ID NO: 19 |
| Rps49 reverse | CGATCTCGCCGCAGTAAA | SEQ ID NO: 20 |
| CG12079-RT-N | TGTTCCCAAGGCGCCGAC | SEQ ID NO: 21 |
| CG12079-RT-C | AGCCTAAGAAGGCGGATAAG | SEQ ID NO: 22 |

Cross-linking and immunoprecipitation (CLIP) assay was performed to determine direct binding between mRNAs and proteins of interests. We adopted a modified method described elsewhere (Ule et al., CLIP: a method for identifying protein-RNA interaction sites in living cells. *Methods* 37, 376-386 (2005)). Briefly, cells were washed once with ice-cold 1×PBS, and covered with 1 mm of ice-cold 1×PBS while being irradiated once at 400 mJ/cm$^2$ using a Stratalinker (12 cm distance from UV source, Stratagene model 2400). Subsequently, cells were treated with lysis buffer containing 1×PBS/1% Tritin X-100. Protein of interest were immunoprecipitated as described below for 3 hours at 4° C. Following three washing steps, 5 minutes each, with 1×PBS/1% Tritin X-100/0.05% SDS at 4° C., the protein/RNA complexes were mixed with SDS sample buffer, run on 8% SDS-PAGE gels, and transferred onto Hybond P membranes. A 2 mm membrane strip was cut at the expected sizes of the immunoprecipitated protein. A 4 mg/ml proteinase K solution in 1×PBS was preincubated at 37° C. for 20 minutes to digest away any contaminated RNases. Subsequently, 30 µl of the preincubated proteinase K solution was incubated with the membrane at 37° C. for 20 minutes, followed by RNA extraction using RNeasy® Mini kit (Qiagen) and RT-PCR analyses as described above.

For the RNA binding assay, total RNAs from 3.7 cm$^2$ of confluent HEK293T cell culture was extracted and mixed with 5 µl of glutathione sepharose-bound recombinant proteins in 30 µl assay buffer containing 1×PBS/0.25% Triton X-100. After incubation for 4 hours at 4° C., three washing steps, each for 10 minutes at 4° C., were performed with assay buffer, followed by RNA extraction as described above. For the protein/RNA association in mammalian cells, recombinant Flag-tagged protein expressed in HEK293T cells was immunoprecipitated as described. RNase inhibitor was supplemented to the lysis and washing buffers. RNA was extracted directly from the immunocomplex by using RNeasy® Mini kit (Qiagen), and the associated RNAs were analyzed by RT-PCR.

Intact mitochondria from in vitro cell cultures, fly heads, fly thoraces, and fly intestinal tissues were purified at described previously (Kristian et al., Isolation of mitochondria with high respiratory control from primary cultures of neurons and astrocytes using nitrogen cavitation. *J Neurosci Methods* 152, 136-143 (2006)). To block the release of mRNAs associated with mitochondria, we added 0.1 mg/ml cycloheximide to all buffer solutions. Samples were homogenized using a Dounce homogenizer. The fraction between the 22% and 50% percoll gradients containing intact mitochondria were carefully transferred into a new reaction tube, mixed with 1 volume of HBS buffer, and centrifuged at 16,000 g for 20 minutes at 4° C. The pellet was subsequently used for RNA extraction as described above and analyzed by RT-PCR.

Live Imaging and Immunohistochemistry.

Adult fly thoraces from 2-5 day old animals raised at 29° C. were dissected and tissues fixed at room temperature for 1 hour in 1×PBS containing 4% paraformaldehyde and 0.3% Triton X-100. The samples were washed one time with 1×PBS and mounted for live imaging using a Leica confocal microscope.

For immunohistochemical analysis of adult fly brains and human in vitro cultures, the samples were washed once with 1×PBS and fixed with 1×PBS containing 4% paraformaldehyde and 4% sucrose at room temperature for 15 minutes. Samples were further washed with 1×PBS for 10 minutes and incubated for an additional 10 minutes with 1×PBS containing 50 mM NH$_4$Cl at room temperature. Samples were then permeabilized with 1×PBS containing 0.25% Triton X-100 for 10 minutes at 4° C. Fixatives were subsequently blocked with 1×PBS containing 5% serum and incubated for 30 minutes at room temperature, followed by incubation with primary antibodies at 4° C. overnight. The primary antibodies used were mouse anti-Tuj-1 (1:1000, Pel-Freez), chicken anti-GFP (1:1000, Abcam), and TH (1:1000, Immunostar). After three washing steps with 1×PBS/0.25% Triton X-100 each for 10 minutes at room temperature, the samples were incubated with secondary antibodies Alexa Fluor® 568-conjugated and Alexa Fluor® 488-conjugated antibodies (1:500, Molecular Probes) for 1.5 hours at 37° C. The samples were washed three times with 1×PBS/0.25% Triton X-100, followed by one washing step with 1×PBS, and subsequently mounted in Gel/Mount (biomeda).

Immunoprecipitation, $m^7$-GTP Sepharose Affinity Chromatography, and Western Blot Analysis.

For immunoprecipitation and $m^7$-GTP sepharose affinity chromatography, extracts of HEK293T cells were prepared by homogenizing cells in lysis buffer [50 mM Tris-HCl, pH7.4, 150 mM NaCl, 5 mM EDTA, 10% glycerol, 1% Triton X-100, 0.5 mM DTT, 60 mM β-glycerophosphate, 1 mM sodium vanadate, 20 mM NaF, and Complete protease inhibitor cocktail (Roche)]. After centrifugation at 16,000 g for 10 min, the supernatant was subjected to immunoprecipitation using the indicated antibodies, or pull-down using $m^7$-GTP sepharose beads for 4 hours at 4° C. Affinity purified complexes were washed 3 times, 5 min each at 4° C.

For the GST pull-down assay, a 500 ml bacterial culture was centrifuged at 2,800 g for 10 minutes at 4° C. The pellet was homogenized in 10 ml ice-cold 1×PBS supplemented with 1 mg/ml lysozyme (Sigma) and stored at −80° C. for 1 hour. All following steps were prepared at 4° C. The pellet was thawed on ice overnight, supplemented with 1% Triton X-100, 5 mM $MgCl_2$, and 2500 U benzonase nuclease (Novagen). After 30 minutes incubation on a horizontal shaker, the extract was centrifuged for 30 minutes at 16,000 g. Next, the supernatant was incubated with 1 ml glutathione sepharose (GE Healthcare) for 4 hours with gentle shaking. The sepharose was washed three times with 1×PBS/0.25% Triton X-100 and subsequently used for the RNA binding assay.

To prepare extracts for Western blot analysis, 4 fly heads, 4 fly thoraces, 50 fly intestines, or cells collected from 3.7 $cm^2$ culture well were directly homogenized in 40 μl of SDS sample buffer using a hand-held motorized homogenizer. After centrifugation at 16,000 g for 10 min, the extracts were separated on 8%, 10%, or 15% SDS-PAGE gels, transferred onto Hybond P membranes, and analyzed with an Enhanced Chemiluminescence Plus Western Blotting Detection kit (Amersham). The following primary antibodies were used: Complex V5α (MS502, mouse monoclonal, 1:1,000, Mito-Sciences), Complex V ATP synthase subunit OSCP (MS505, 1:1000, mouse monoclonal, Mitoscienes), Complex IV cytochrome oxidase subunit 1 (MS404, 1:1,000, mouse monoclonal, MitoScienes), Complex II subunit 70 kD Fp (MS204, 1:1,000, mouse monoclonal, MitoScienes), Complex I 30 kD NADH dehydrogenase iron-sulfur protein 3 (MS110 and MS112, 1:1,000, mouse monoclonal, Mito-Scienes), β-III Tubulin (1:1,000, rabbit, Sigma), β-I+II Tubulin (1:1,000, rabbit, Sigma), α-Actin (MAB1501, 1:1,000, mouse monoclonal, Chemicon), Flag (M2, WB: 1:3000, Sigma), eIF4E (1:1,000, rabbit, Cell Signaling), Rps6 (54D2, 1:1,000, mouse, Cell Signaling), PINK1 (1:1,000, rabbit, Abcam), KDEL (1:1,000, mouse, Stressgen), GST (1:1,000, goat, Amersham), Myc (4A6, 1:1,000, mouse, Millipore), Pumilio-1 (EPR3795, 1:1000, Abcam).

DNA Cloning and Site-Directed Mutagenesis, siRNA Homo-Duplex Generation, and Transfection.

Lentiviral vector containing the coding sequence for mito-GFP is described before (Yu et al., The PINK1/Parkin pathway regulates mitochondrial dynamics and function in mammalian hippocampal and dopaminergic neurons. *Hum Mol Genet* 20, 3227-3240 (2011)). Full-length human PINK1 construct with a C-terminal Flag-tag was described before (Yang et al., Mitochondrial pathology and muscle and dopaminergic neuron degeneration caused by inactivation of *Drosophila* Pink1 is rescued by Parkin. *Proc Natl Acad Sci USA* 103, 10793-10798 (2006)). Introduction of the point mutation G309D into PINK1 were performed using QuikChange II XL Site-directed mutagenesis kit (Stratagene). N-terminal amino acid 1 to 111 deleted human PINK1 was subcloned as EcoRI/XhoI fragment into pGEX-6p-1 and kindly prepared by Dr. Yuzuru Imai. To generate a control RNAi construct we annealed sense 5'-GGAATTCCCA-GACCGCTgaTGAGCCTttggtaccAGGCTCATCAGCG-GTCTG GggGAATTCC-3' (SEQ ID NO:23) and antisense 5'-GGAATTCCCCCAGACCGCTGATGAGCCTGGTAC-CAAAGGCTCATCAGCGGTCTGGGA ATTCC-3' (SEQ ID NO:24) oligonucleotides, restricted, and subcloned them as EcoRI fragment into pcDNA3.1 (+). For the generation of two human pumilio-1 (pum-1) RNAi constructs specific for two sites within the pum-1 cDNA we annealed sense (nt2814) 5'-GGAATTCCCAGAAAGCTCTTGAGTTTttg-gtaccAAACTCAAGAGCTTTCTGGggG AATTCC-3' (SEQ ID NO:25), antisense (nt2814) 5'-GGAATTC-CCCCAGAAAGCTCTTGAGTTTGGTACCAAAAACT-CAAGAGCTTTCTGGGAA TTCC-3' (SEQ ID NO:26), or sense (2541) 5'-GGAATTCGGAGATTGCTGGACATAT-AttggtaccTATATGTCCAGCAATCTCCggGAATTCC-3' (SEQ ID NO:27), and antisense (2541) 5'-GGAATTCCCG-GAGATTGCTGGACATATAGGTACCAATATATGTCCA-GCAATCTCCGAA TTCC-3' (SEQ ID NO:28) oligos, restricted, and subcloned them as EcoRI fragments into pcDNA3.1(+). To suppress PINK1 we used the RNAi constructs TRCN7099 and TRCN7101 purchased from Open Biosystems. All newly generated constructs were confirmed by DNA sequencing. The pcDNA3-Flag-human PABP plasmid was kindly provided by Dr. Lykke-Andersen (Lykke-Andersen, J. & Wagner, E. Recruitment and activation of mRNA decay enzymes by two ARE-mediated decay activation domains in the proteins TTP and BRF-1. *Genes Dev* 19, 351-361 (2005)).

To generate homo-duplex pum-1 siRNAs, we annealed sense 5'-CCAGAAAGCUCUUGAGUUUuu-3' (SEQ ID NO:29) and antisense 5'-AAACUCAAGAGCUUUCUG-Gcg-3' (SEQ ID NO:30) oligonucleotides. As control homo-duplex siRNA, we annealed sense 5'-CCAGCCUC-CGUUUCACCGGUU-3' (SEQ ID NO:31) and antisense 5'-AACCGGUGAAACGGAGGCUG-3' (SEQ ID NO:32) oligos. RNA oligomers were synthesized and purified by the Protein and Nucleic Acid (PAN) Facility at Stanford University.

All transfections were prepared as follows. For a 3.7 $cm^2$ cell culture well, HEK293T cells were seeded at around 15 to 20 hours before the transfection at 50% confluence. For transfection, we mixed 1.5 μg DNA and 3.7 μl 2.5M $CaCl_2$ by pipetting up and down several times, and then adding 17.75 μl $H_2O$. The mixture was then added slowly to 22.95 μl 2×BES-buffered saline with vortexing. The mixture was incubated for 3 minutes at room temperature and transferred onto cells covered with serum-free medium. After 3 hours the medium was changed to normal growth medium containing 10% fetal bovine serum (FBS). A 3.7 $cm^2$ cell culture well containing iDN cells was transfected with siRNA by mixing 1 μl of 50 μM homo-duplex siRNA and 3.7 μl 2.5M CaCl₂, followed by adding 17.75 μl H₂O. With vortexing, the mixture was drop-wise added to 22.45 μl 2×BES-buffered saline, and incubated for 1 minute prior to transfer onto iDN cells. Three hours post-transfection, the RNA/medium mixture was replaced with fresh N3 medium.

ATP Measurement.

For each measurement, two thoraces containing mostly muscle tissues dissected from 3-day old flies, or in vitro cell cultures trypsinized from 3.7 cm² culture plates were collected and transferred into a new 1.5 ml reaction tube, centrifuged at 1,000 g at 4° C., and washed once with ice cold 1×PBS. ATP level was measured by using the luciferase based bioluminescence assay (ATP Bioluminescence Assay Kit HS II, Roche Applied Science). Briefly, thoraces or cell pellets were homogenized in 100 μl lysis buffer, boiled for 5 minutes, and centrifuged at 16,000 g for 1 minute. 2 μl of the supernatant was mixed with 98 μl of dilution buffer and 10 μl luciferase/luciferin mixture provided with the kit. The luminescence was immediately measured. As standard we used various concentrations of ATP alone to convert the measured luciferase activity to the amount of ATP. For each sample at least three independent measurements were prepared.

Drosophila Genetics.

The PINK1$^{B9}$ mutant line was kindly provided by Dr. Jongkeong Chung (Park et al., Mitochondrial dysfunction in Drosophila PINK1 mutants is complemented by parkin. Nature 441, 1157-1161 (2006)). The UAS-mito-GFP was provided by Dr. William Saxton. UAS-dPINK1 RNAi was generated as described (Yang et al., Mitochondrial pathology and muscle and dopaminergic neuron degeneration caused by inactivation of Drosophila Pink1 is rescued by Parkin. Proc Natl Acad Sci USA 103, 10793-10798 (2006)). UAS-Miro RNAi$^{106683}$ was received from Vienna Drosophila RNAi Center. UAS-dMiro was kindly provided by Dr. Konrad Zinsmaier. TH-Gal4 was gift from Dr. Serge Birman. Drp1-null mutant line drp1² and extra copy Drp1 transgenic line FLAG-FLASH-HA-drp1⁺ were gifts from Drs. Patrick Verstreken and Hugo Bellen (Verstreken, P., et al. Synaptic mitochondria are critical for mobilization of reserve pool vescicles at Drosophila neuromuscular junctions. Neuron 47, 365-378 (2005)). TRiP RNAi lines for pumilio (#26725), Tim8 (#31082), and all other general fly lines were obtained from the Bloomington Drosophila Stock Center.

Wing Posture and Jumping Ability Assays.

To assess the abnormal wing posture phenotype, 20 flies per vial were aged at the indicated temperature and the percentage of flies having upright or drooped wing posture was calculated. The jump/flight ability assay was performed using 5 to 10 flies per vial. Jump/flight events were counted for 2 minutes while gently tapping the vials to initiate fly movement. Data represent the behavioural responses of 10 animals. For each genotype at least three independent experiments were performed for both assays.

Example 1

To identify a set of factors capable of efficiently inducing iDN formation from aged human fibroblasts, thirty candidate genes relevant to DN development or maintenance were screened using a validated sub-pooling approach (Takahashi et al., Induction of pluripotent stem cells from adult human fibroblasts by defined factors. Cell 131, 861-872 (2007); Vierbuchen et al., Direct conversion of fibroblasts to functional neurons by defined factors. Nature 463, 1035-1041 (2010)). One factor pool was identified containing Lmx1 b, Nurr1, c-Fos, and Ebf1 that produced iDNs at ~30% efficiency (FIG. 1a-d). This 4-factor combination induced high endogenous MASH1 expression (FIG. 1g). Expression of neuronal progenitor markers Sox2 and Otx2 could not be detected by RT-PCR during the induction process (FIG. 1e), suggesting that this reprogramming did not involve a stem cell-like intermediate state. The expression of TH, DAT, VMAT2, PSD-95, and Tuj-1 in the converted neurons was confirmed by immunohistochemistry (FIG. 1b).

Gene expression profiling further confirmed the identity of the iDNs. RT-PCR analysis detected the expression of DN markers Pitx3, En2, TH, VMAT2, DAY, cRET, Msx1, Ngn2, Sox2, Foxa2, MASHI (Ascl1) in the iDNs but not fibroblasts (FIG. 1f). As a positive control, DNs dissected from adult mouse midbrain tissues were used. In addition, mRNA profiling by microarray analysis of control fibroblasts, human midbrain DA neurons (Lesnick et al., A genomic pathway approach to a complex disease: axon guidance and Parkinson's disease. PLoS Genet 3, e98 (2007)), and iDNs from normal subjects (FIG. 1g) were performed. These results clearly indicated that forced expression of the 4 TFs changed the mRNA expression profile of human fibroblasts towards that of human midbrain DNs.

This protocol also allowed the conversion patient fibroblasts carrying the pathogenic PINK1(G309D) mutation (Hoepken et al., Mitochondrial dysfunction, peroxidation damage and changes in glutathione metabolism in PARK6. Neurobiol Dis 25, 401-411 (2007)) into iDNs, which were generated at similar efficiency as control iDNs and did not show obvious signs of cell death in culture.

Example 2

Figure 2A:
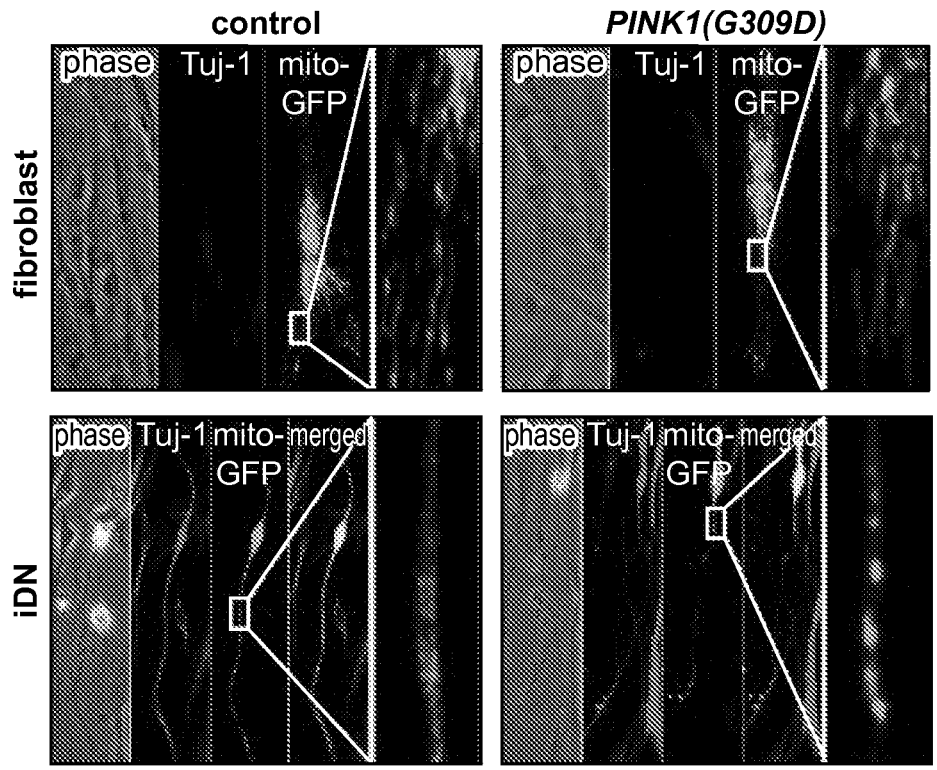
FIG. 2a-2g shows the characterization of iDNs generated from control and PINK1(G309D) PD patient fibroblasts.
Figure 2B:
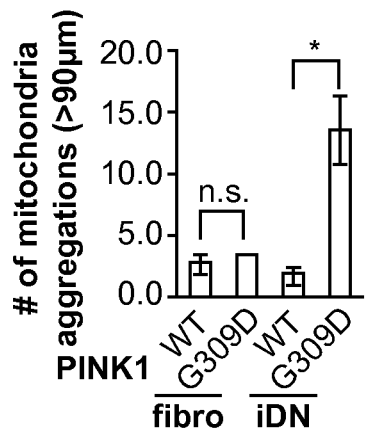
Figure 2C:
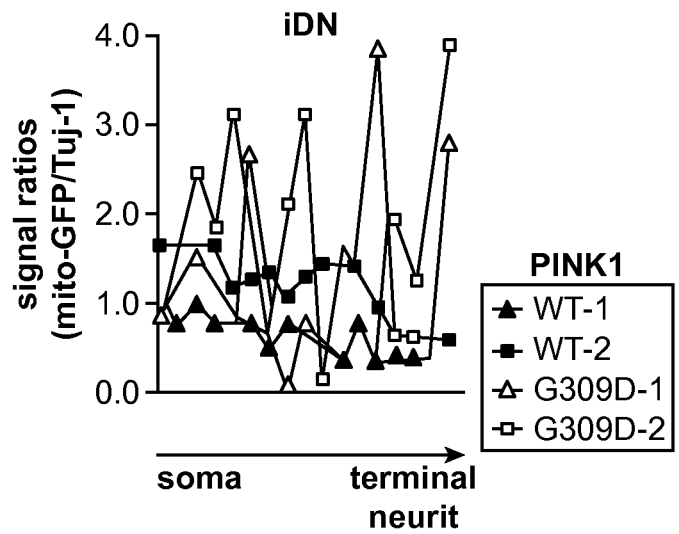
Figure 2D:
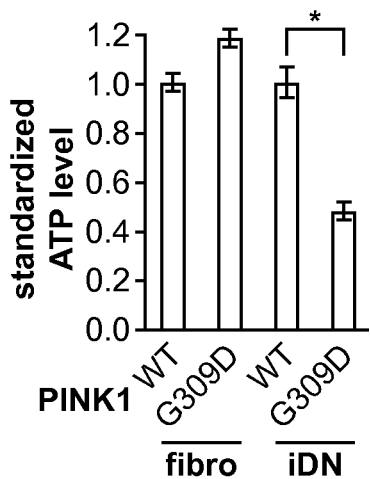
Figure 2E:
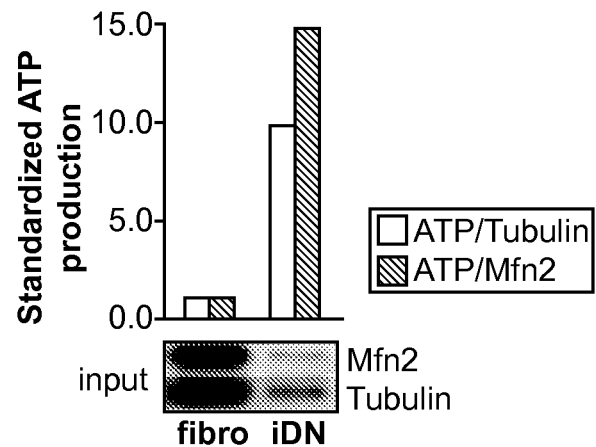

PINK1(G309D) patient iDNs were examined for mitochondrial defects, since studies in flies and mammals have implicated PINK1 in mitochondrial regulation (Clark, I. E. et al., Drosophila pink1 is required for mitochondrial function and interacts genetically with parkin. Nature 441, 1162-1166 (2006); Park et al., Mitochondrial dysfunction in Drosophila PINK1 mutants is complemented by parkin. Nature 441, 1157-1161 (2006); Yang et al., Mitochondrial pathology and muscle and dopaminergic neuron degeneration caused by inactivation of Drosophila Pink1 is rescued by Parkin. Proc Natl Acad Sci USA 103, 10793-10798 (2006); Yu et al., The PINK1/Parkin pathway regulates mitochondrial dynamics and function in mammalian hippocampal and dopaminergic neurons. Hum Mol Genet 20, 3227-3240 (2011)). Compared to control iDNs, patient iDNs exhibited abnormal distribution and morphology of mitochondria in neuronal processes, as monitored with a mito-GFP reporter (FIG. 2a). Patient iDNs showed a significant increase in the number of mitochondrial units larger than 90 μm in diameter (FIG. 2b). Moreover, quantification of the ratio of signal intensity of mito-GFP versus the neuronal marker Tuj-1 along neurite length revealed reduced mitochondrial occupancy of neuronal processes in patient iDNs (FIG. 2c). Supporting that the mitochondrial morphological changes reflected a disruption of mitochondrial function, we detected ~53% reduction of cellular ATP levels in PINK1 (G309D) iDNs compared to control iDNs (FIG. 2d). Notably, ATP measurements of fibroblasts and iDNs from controls showed that iDNs produced more than 10 fold more ATP than fibroblasts, indicating that iDNs have higher demand for mitochondrial oxidative phosphorylation, and hence respiratory chain complex (RCC) activity, than fibroblasts (FIG. 2e).

Figure 2F:
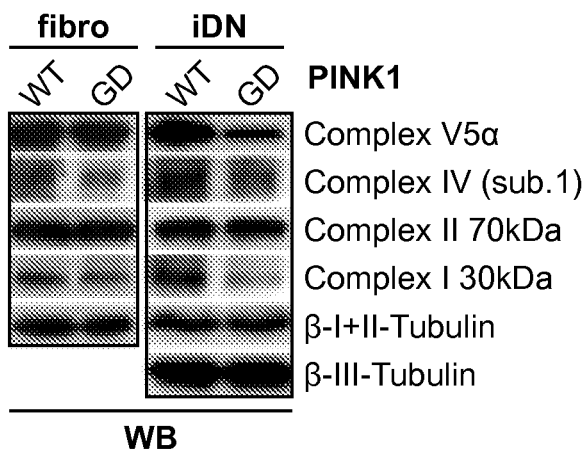
Figure 2G:
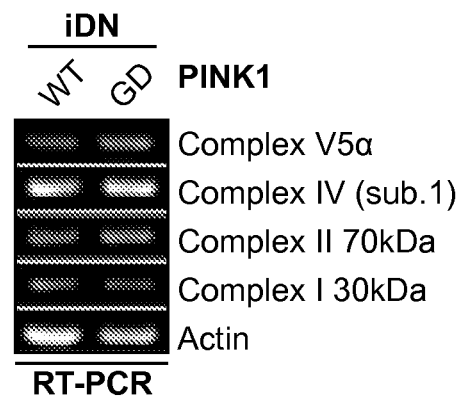
Figures 3A, 3B:
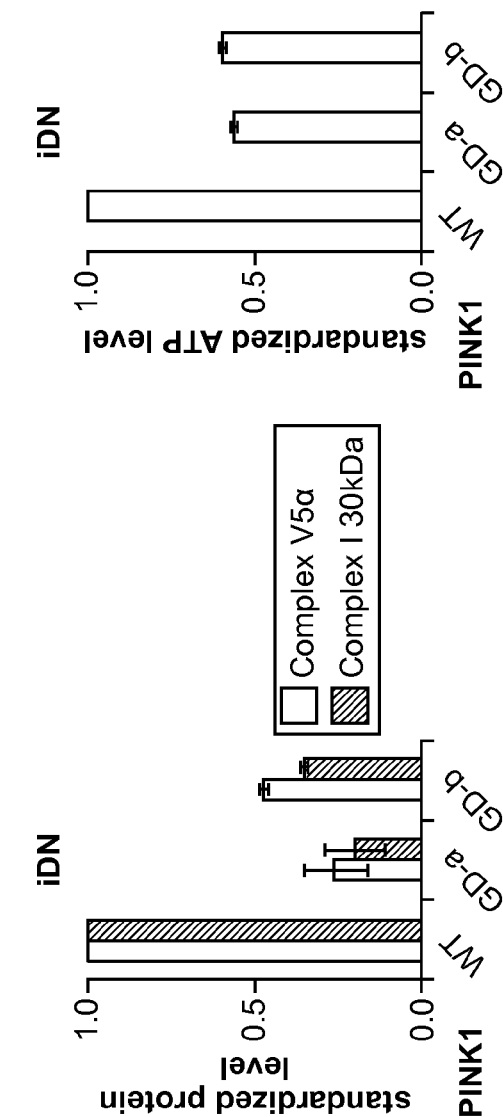
FIG. 3a-3b shows Western blot analysis and quantification of standardized RCC protein level (FIG. 3a), and ATP level (FIG. 3b) of control iDNs or patient iDNs derived from two individuals carrying the PINK1(G309D) mutation. Actin serves as control. Data were collected from three independent experiments (*P<0.05).

Next, molecular correlates of the physiological changes observed in PINK1(G309D) iDNs were searched. Reduced expression of certain respiratory chain complex (RCC) proteins were detected, including subunits of complex I, IV, and V (FIG. 2f). Similar effects were observed in a different patient iDN sample carrying the same familial mutation (FIG. 3). RT-PCR analysis showed that reduced RCC protein expression was not due to reduced mRNA levels in PINK1 (G309D) iDNs (FIG. 2g). Importantly, patient-derived fibroblasts did not show significant changes in RCC protein expression, mitochondrial distribution and morphology, or ATP production compared to control fibroblasts (FIG. 2a,b, d,f), indicating that the pathogenic mutation may exert DN-specific effects on mitochondrial function.

Figure 4C:
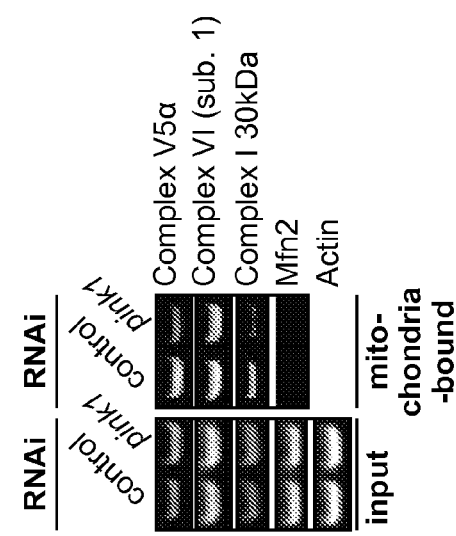
FIG. 4a-4k shows that PINK1 regulates the mitochondrial localization and translation of RCC mRNAs.
Figure 4B:
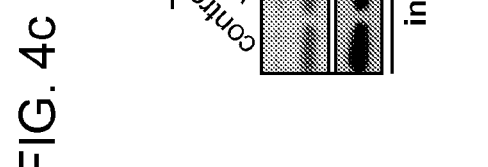
Figure 4A:
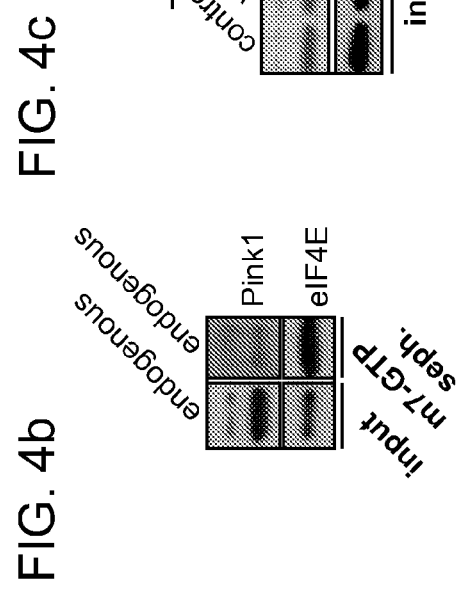
Figure 5:
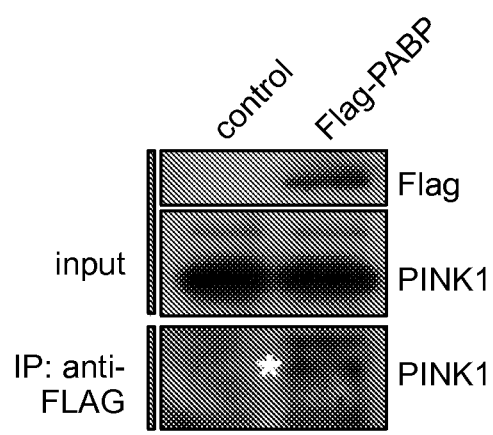
FIG. 5 shows the interaction between ectopically expressed poly-A binding protein (PABP) and endogenous PINK1. Flag-tagged PABP expressed in HEK293T cells was subjected to immunoprecipitation (IP). Endogenous PINK1 (marked with an white asterisk) could be detected in the PABP IP fraction by western blot analysis. Anti-Flag beads alone served as control.

To understand the molecular mechanism by which PINK1 affects the levels of the RCC proteins that are nuclear-encoded, it was assessed whether PINK1 may act via translational regulation. In HEK293T cells, both exogenous and endogenous PINK1 associated with the translation initiation complex (TIC), as detected with $m^7$-GTP-sepharose chromatography (FIG. 4a,b). In contrast, the pathogenic G309D mutation impaired such association (FIG. 4c). Interestingly, the association of PINK1 with $m^7$-GTP-sepharose was dramatically reduced by RNase A treatment (FIG. 4a), suggesting that PINK1 associates with the TIC in an RNA-dependent manner. In comparison, the $m^7$-GTP-sepharose binding by eIF4E, a component of the TIC, was not affected by RNase A treatment (FIG. 4a). Endogenous PINK1 also interacted with PABP (FIG. 5), a protein known to regulate translational initiation (Craig et al., Interaction of polyadenylate-binding protein with the eIF4G homolog PAIP enhances translation. Nature 392, 520-523 (1998)), further strengthening a role of PINK1 in translational regulation.

Figure 4F:
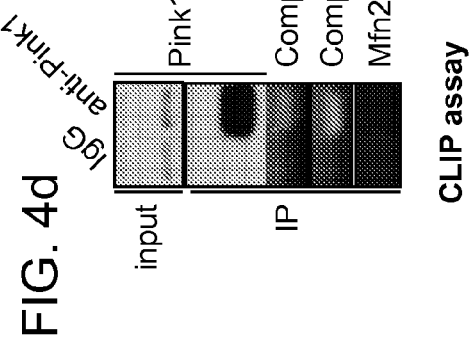
Figure 4E:
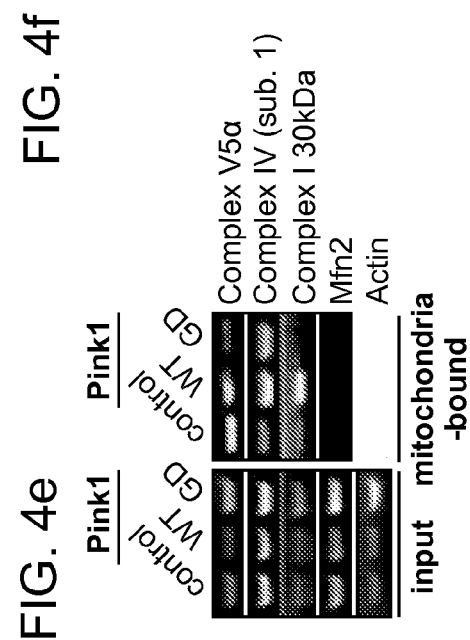
Figure 4D:
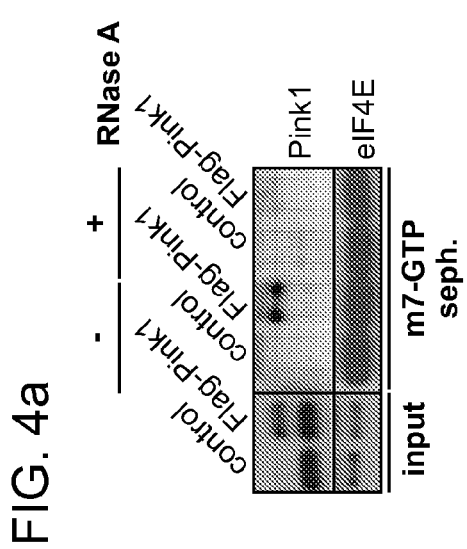
Figure 4I:
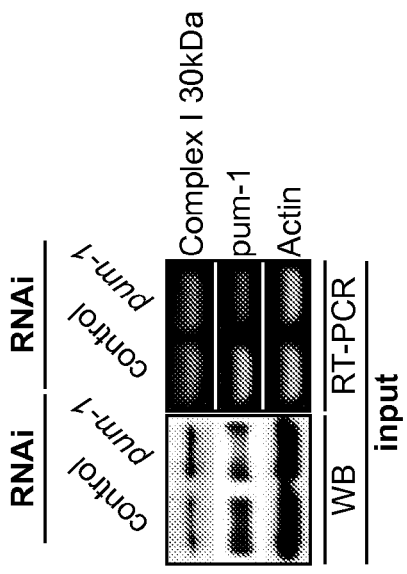
Figure 4H:
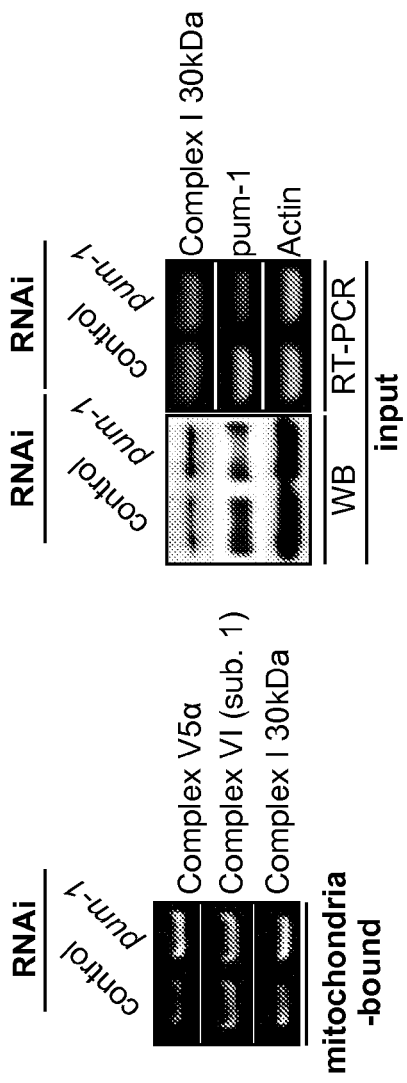
Figure 4K:
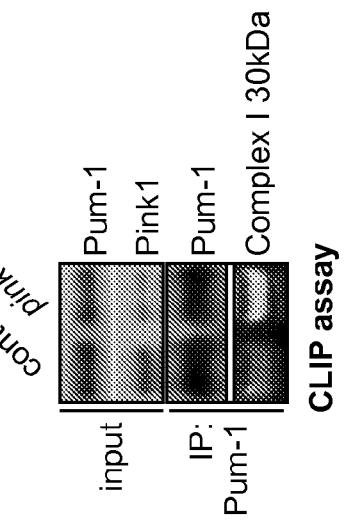
Figure 4G:
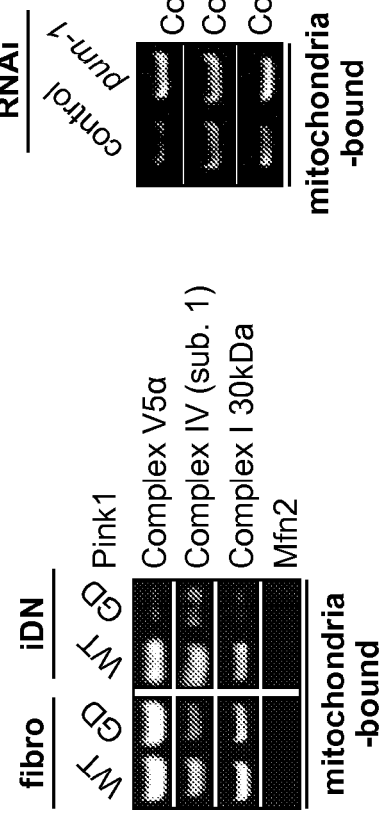
Figure 6:
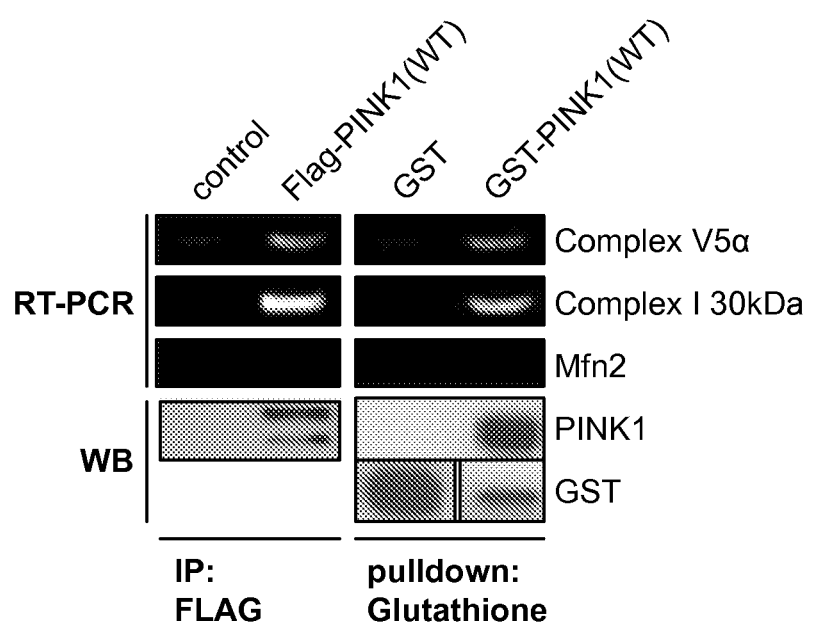
FIG. 6 shows RNA binding activity of recombinant PINK1. Left, Flag-tagged PINK1(WT) was purified from HEK293T cells by immunoprecipitation, followed by an RNA extraction from the immunocomplex and further RNA analysis by RT-PCR. Right, a recombinant GST-PINK1 protein with amino acid 1 to 111 of full-length PINK1 deleted was used to bind to total RNAs extracted from HEK293T cells. Following several washing steps, RNAs bound to GST-PINK1 were extracted and analyzed by RT-PCR. Note that Mfn2 RNA did not bind to recombinant PINK1. Western blot analyses of the proteins used in the RNA binding assay are shown. GFP and GST alone serve as controls.
Figure 7A:
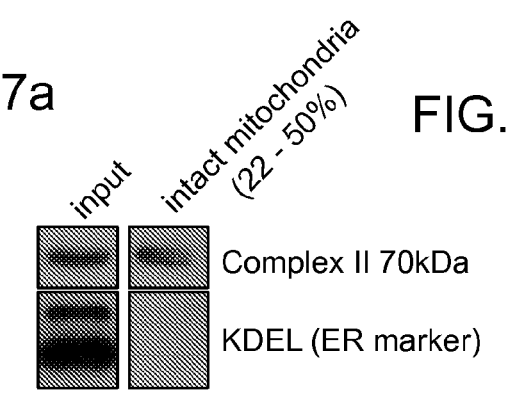
FIG. 7a-7b shows a Western blot analysis of purified mitochondrial fractions.
Figure 7B:
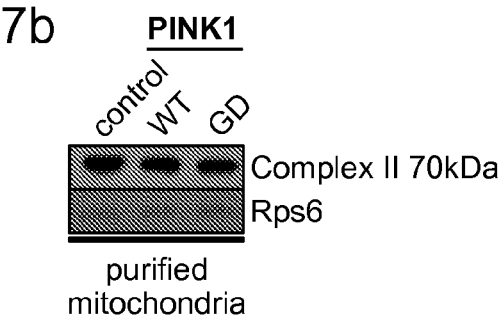

The molecular basis of the RNA-dependence of PINK1 association with the TIC was also investigated. Analysis of PINK1 immunoprecipitate from HEK293T cell extracts detected the presence of RCC mRNAs (FIG. 6), suggesting that PINK1 may associate with mRNAs in vitro. To test whether this mRNA-association of PINK1 was direct, CLIP assays were performed (Ule et al., CLIP: a method for identifying protein-RNA interaction sites in living cells. Methods 37, 376-386 (2005)). This analysis clearly demonstrated that PINK1 directly binds to RCC mRNAs (FIG. 4d). It was next investigated how PINK1, a primarily mitochondrial protein, may regulate the translation of RCC mRNAs that are transcribed in the nucleus. It was determined that these RCC mRNAs and the cytoplasmic ribosomes were present in highly purified mitochondrial fraction from HEK293T cells (FIG. 4e, FIGS. 7a and b), as described before in yeast (Ades et al., The products of mitochondria-bound cytoplasmic polysomes in yeast. J Biol Chem 255, 9918-9924 (1980)) and Jurkat cells (Matsumoto et al., Localization of mRNAs encoding human mitochondrial oxidative phosphorylation proteins. Mitochondrion 12, 391-398 (2012)). This presumably serves to facilitate co-translational RCC import and assembly. Moreover, PINK1(WT) overexpression increased the mitochondria-association of RCC mRNAs (FIG. 4e). In contrast, PINK1(G309D) had opposite effects (FIG. 4e). Knockdown of PINK1 by RNAi had similar effects as PINK1(G309D) overexpression (FIG. 4f), suggesting that G309D represents a loss-of-function mutation that can act as a dominant negative when overexpressed. PINK1(G309D) iDNs also showed significant reduction of mitochondria-bound RCC mRNAs (FIG. 4g).

The control Mfn2 mRNA was not mitochondria-bound and was not bound by PINK1 in the CLIP assay (FIG. 4d-g). Collectively, these results suggest that PINK1 specifically interacts with RCC mRNAs and regulates their mitochondrial recruitment.

Figure 4J:
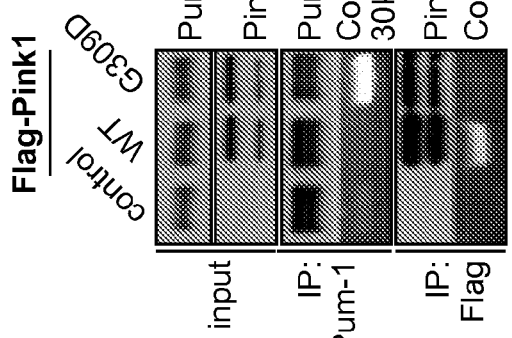
Figure 8:
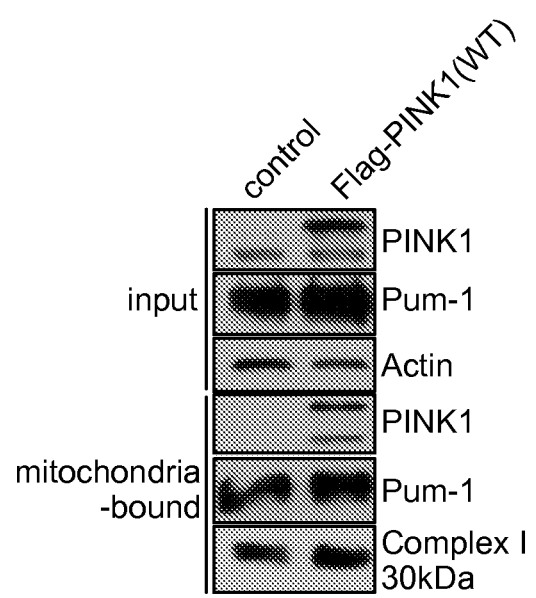
FIG. 8 shows a Western blot analysis showing the co-presence of exogenous PINK1 and endogenous Pum-1 in the mitochondria fraction purified from HEK293T cells. Overexpressed PINK1(WT) and endogenous Pum-1 are both readily detected in purified mitochondria. Actin serves as control for the input fraction, and Complex-I 30 kD for purified mitochondria.
Figure 9A:
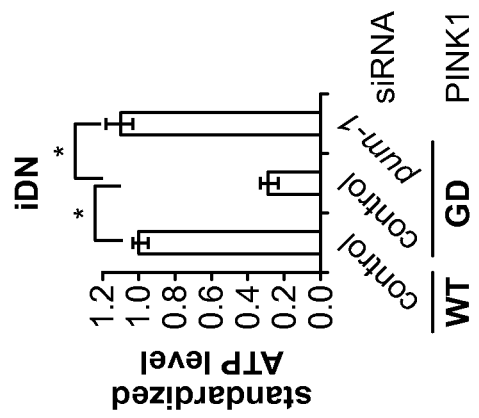
FIG. 9a-9e shows that inhibition of Pum-1 restores the mitochondria localization and translation of RCC mRNAs and rescues mutant phenotypes in PINK1(G309D) iDNs and Drosophila PINK1 models.
Figure 9B:
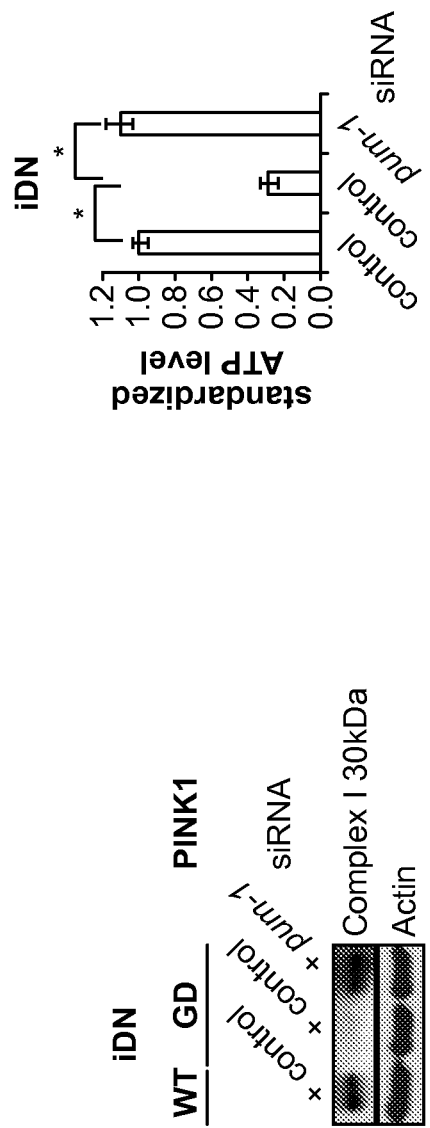
Figure 10A:
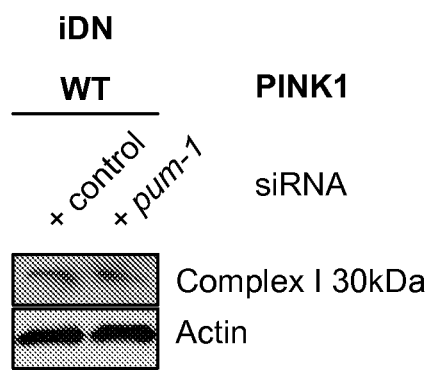
FIG. 10a-10b shows an analysis of control iDNs transfected with control siRNA or Pum-1 siRNA. WB analyses of Complex-I 30 kD protein level (FIG. 10a), and standardized ATP levels (FIG. 10b) are shown. Actin serves as control. Data were collected from three independent experiments (P<0.05).
Figure 10B:
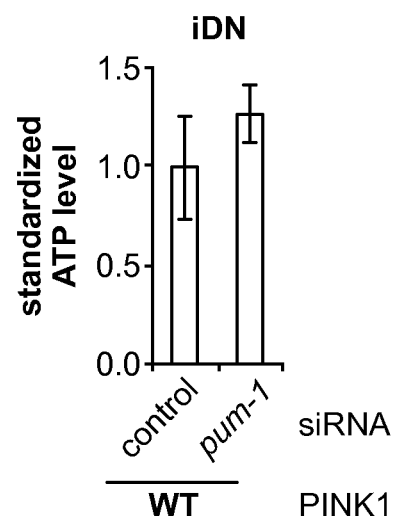

Since the RCC protein levels correlated well with the mitochondria-bound mRNA levels, and their total cellular mRNA levels were not affected by PINK1, the translation of RCC mRNAs might be normally repressed before they were recruited to mitochondria and translationally activated locally by PINK1. It was tested whether Pumilio (Pum), a conserved RNA binding protein and translational repressor (Murata et al., Binding of pumilio to maternal hunchback mRNA is required for posterior patterning in Drosophila embryos. Cell 80, 747-756 (1995); Quenault et al., PUF proteins: repression, activation and mRNA localization. Trends Cell Biol 21, 104-112 (2011)), might be involved. It was determined that RNAi knockdown of Pum-1, a mammalian homolog of Drosophila Pum, resulted in increased mitochondria-association and translation of RCC mRNAs (FIG. 4h,i). Intriguingly, in PINK1(G309D) overexpression or PINK1 RNAi HEK293T cells, the binding between Pum-1 and complex-I 30 kD subunit mRNA was significantly increased as detected by the CLIP assay (FIG. 4j,k), suggesting that PINK1 may normally antagonize Pum-1 in regulating the mitochondria-recruitment and translation of RCC mRNAs. Supporting this notion, like PINK1, endogenous Pum-1 was localized to mitochondria (FIG. 8), and Pum-1 RNAi rescued the mutant phenotypes of PINK1 (G309D) iDNs in terms of RCC protein expression and ATP production (FIG. 9a,b), although Pum-1 RNAi in control iDNs had no obvious effect (FIG. 10).

Figure 9C:
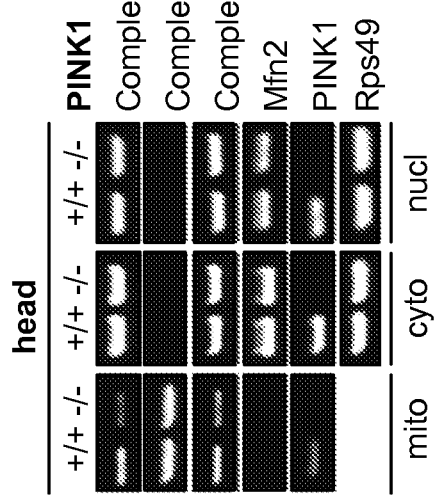
Figures 9D, 9E:
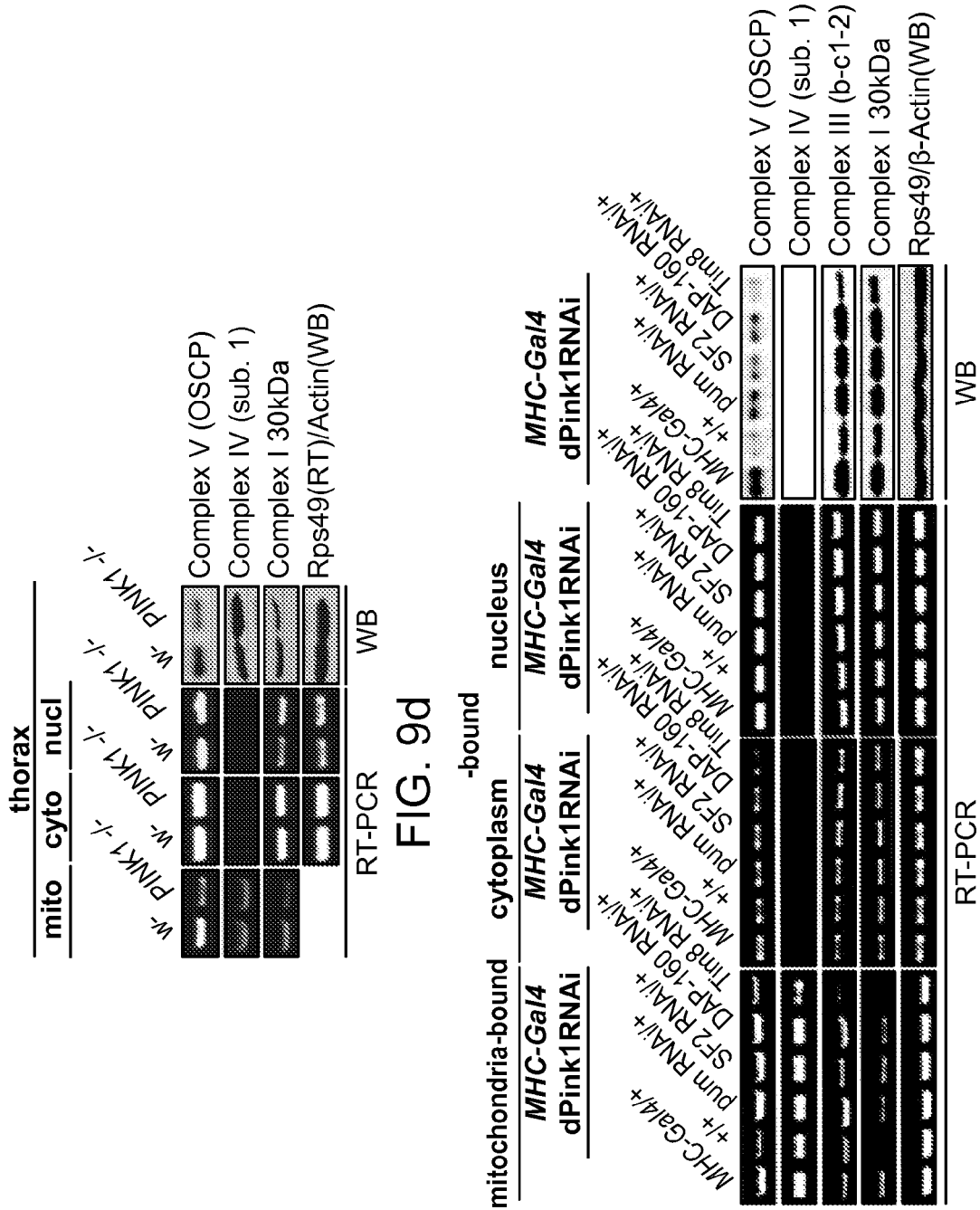
Figure 11:
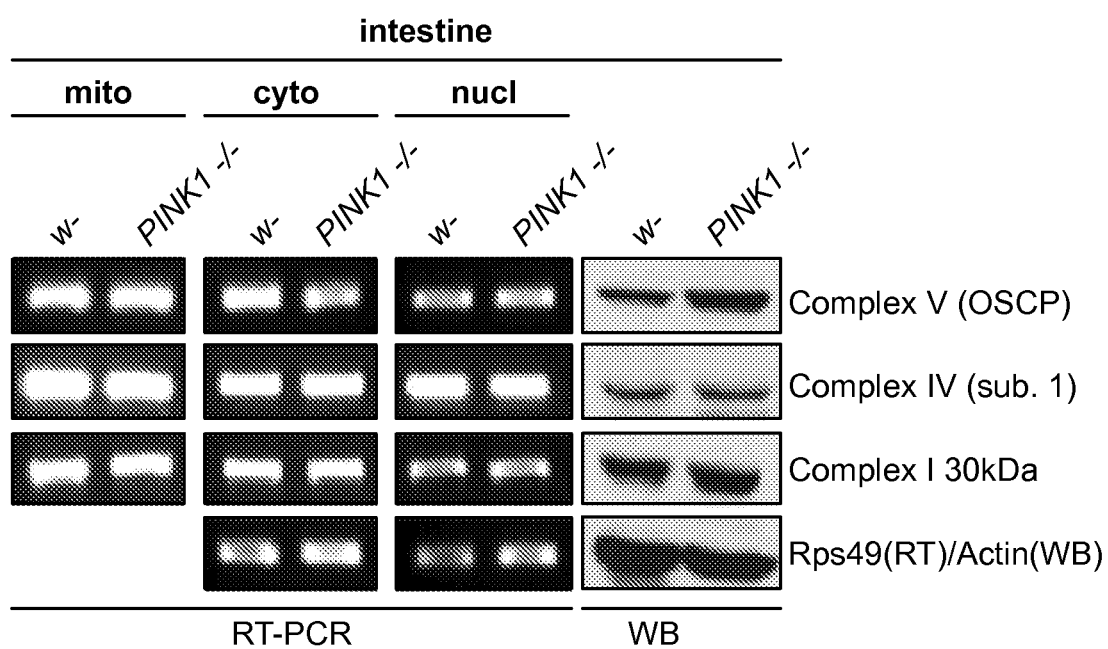
FIG. 11 shows an analysis of the mitochondrial association of RCC mRNA in the intestinal tissue of PINK1$^{B9}$ null mutant flies. mRNAs extracted from purified mitochondria (mito), the cytoplasm (cyto), or the nucleus (nucl) fractions were analysed by RT-PCR. Rps49 mRNA serves as control for RT-PCR, Actin for Western blot analyses of input, and Complex-IV (sub.1) for purified mitochondria.

It was further tested whether regulation of the recruitment and translation of mitochondria-bound RCC mRNAs by PINK1 revealed in human iDNs is a general phenomenon. The Drosophila PINK1 mutant and RNAi animals are well-established PD models (Clark, I. E. et al., Drosophila pink1 is required for mitochondrial function and interacts genetically with parkin. Nature 441, 1162-1166 (2006); Park et al., Mitochondrial dysfunction in Drosophila PINK1 mutants is complemented by parkin. Nature 441, 1157-1161 (2006); Yang et al., Mitochondrial pathology and muscle and dopaminergic neuron degeneration caused by inactivation of Drosophila Pink1 is rescued by Parkin. Proc Natl Acad Sci USA 103, 10793-10798 (2006)). Comparison of mitochondria-bound mRNAs prepared from wild type and PINK1$^{B9}$ mutant fly heads showed reduced levels of RCC mRNAs in PINK1$^{B9}$ mutant (FIG. 9c). The changes mostly occurred post-transcriptionally and specifically at the mitochondria, as we did not find changes in mRNA levels present in the cytoplasm or nuclear fractions (FIG. 9c). Similarly, in mitochondria purified from thoracic muscles that are affected by d PINK1$^{B9}$ mutation, we detected reduced mitochondria-association of RCC mRNAs, whereas no change was observed in the cytoplasmic or nuclear fractions (FIG. 9d). Western blot analysis confirmed reduced expression of RCC proteins in PINK1$^{B9}$ mutant (FIG. 9d). In contrast, the mitochondrial recruitment and translation of RCC mRNAs were not affected in PINK1$^{B9}$ intestine (FIG. 11), where PINK1 mutants did not show obvious phenotypes. These results supported that altered localization and translation of mitochondria-bound mRNAs played a pathogenic role in PINK1$^{B9}$ mutants.

Figure 12:
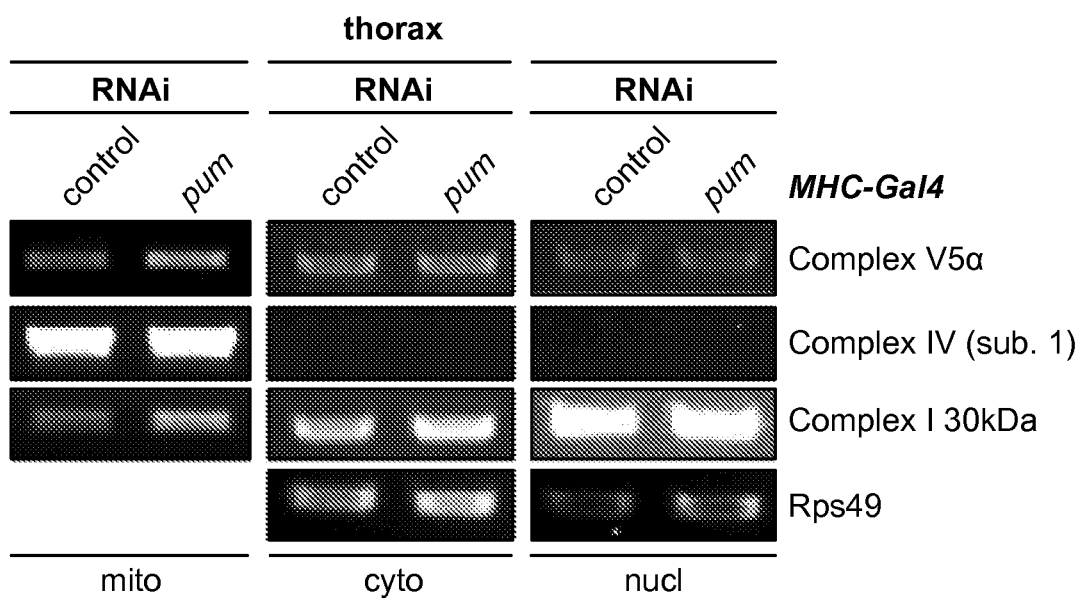
FIG. 12 shows the effects of Pum RNAi in Drosophila. MHC-Gal4-driven Pum RNAi in the wild type background increased the association of RCC mRNAs with mitochondria. Mitochondrial encoded Complex IV (sub. 1) serves as control for purified mitochondria (mito). Rps49 serves as control for the cytoplasmic (cyto), and nuclear (nucl) fractions.

Next, it was tested whether restoration of the localization and translation of mitochondria-bound mRNAs could rescue PINK1 mutant phenotypes in Drosophila. Genetic studies in yeast have identified a number of factors, including Puf3p20, Np13p21, and Panlp22, in regulating the localization and translation of mitochondria-bound mRNAs. The effects of manipulating the functions of *Drosophila* Pumilio (Pum), SF2, and DAP-I60, homologs of yeast Puf3p, Np13p, and Panlp, respectively were tested. It was found that inhibition of *Drosophila* Pum and SF2 by RNAi led to increased RCC mRNA association with mitochondria, supporting a role of Pum and SF2 in regulating the mitochondria-recruitment and translation of RCC mRNAs (FIG. 12). Importantly, inhibition of Pum and SF2 effectively restored the localization and translation of mitochondria-bound RCC mRNAs in Mhc-Gal4>dPINK1-RNAi animals (FIG. 9e).

Figure 13A:
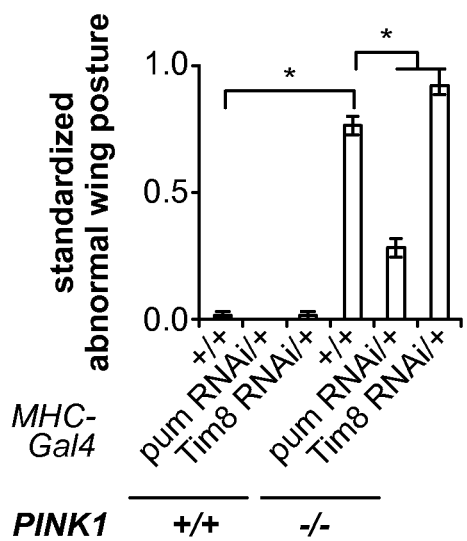
FIG. 13a-13f shows that inhibition of Pum rescues PD-associated phenotypes in *Drosophila* PINK1 models.
Figure 13B:
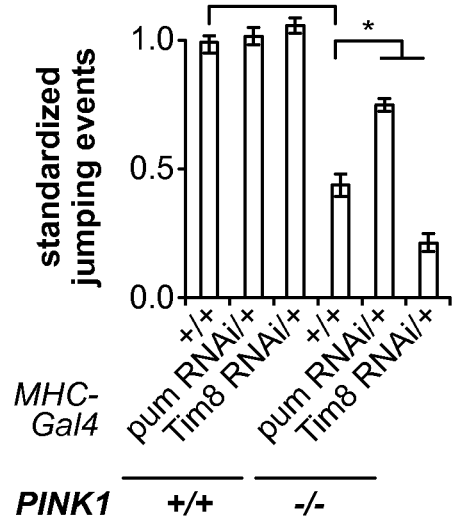
Figure 13C:
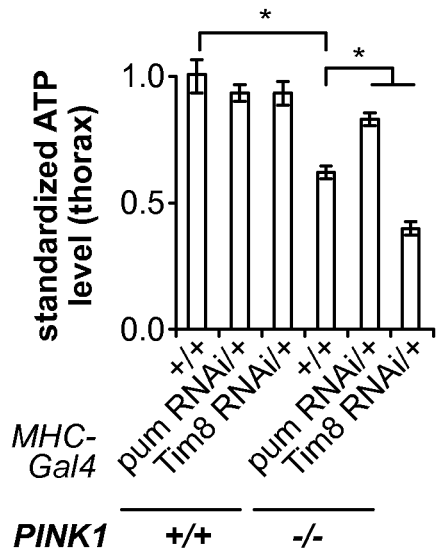
Figure 13D:
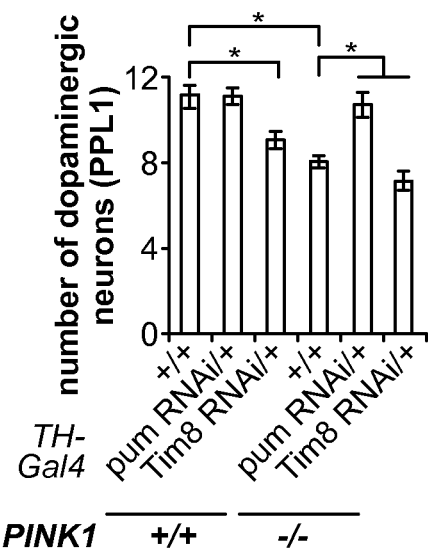
Figure 13E:
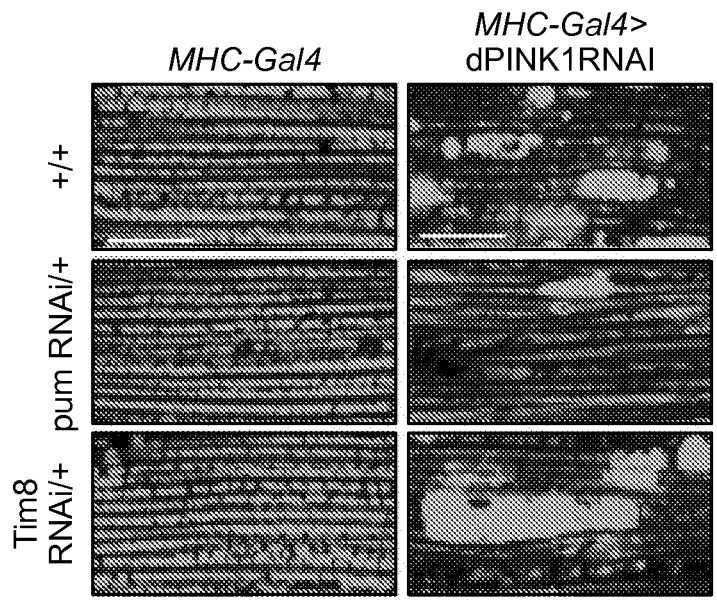
Figure 13F:
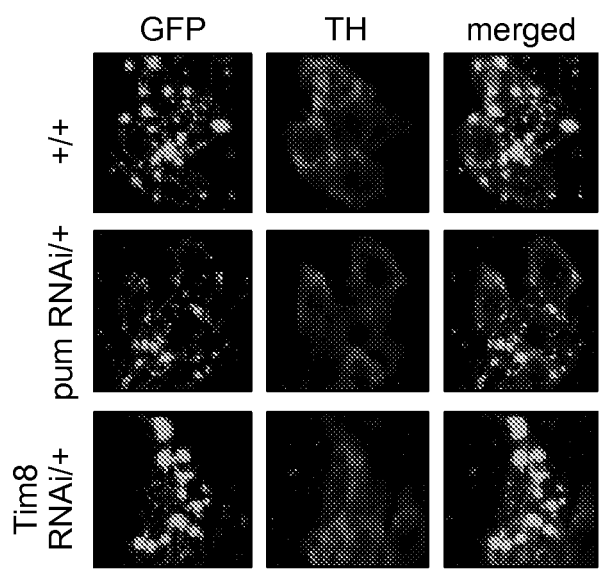
Figures 14A, 14B, 14C:
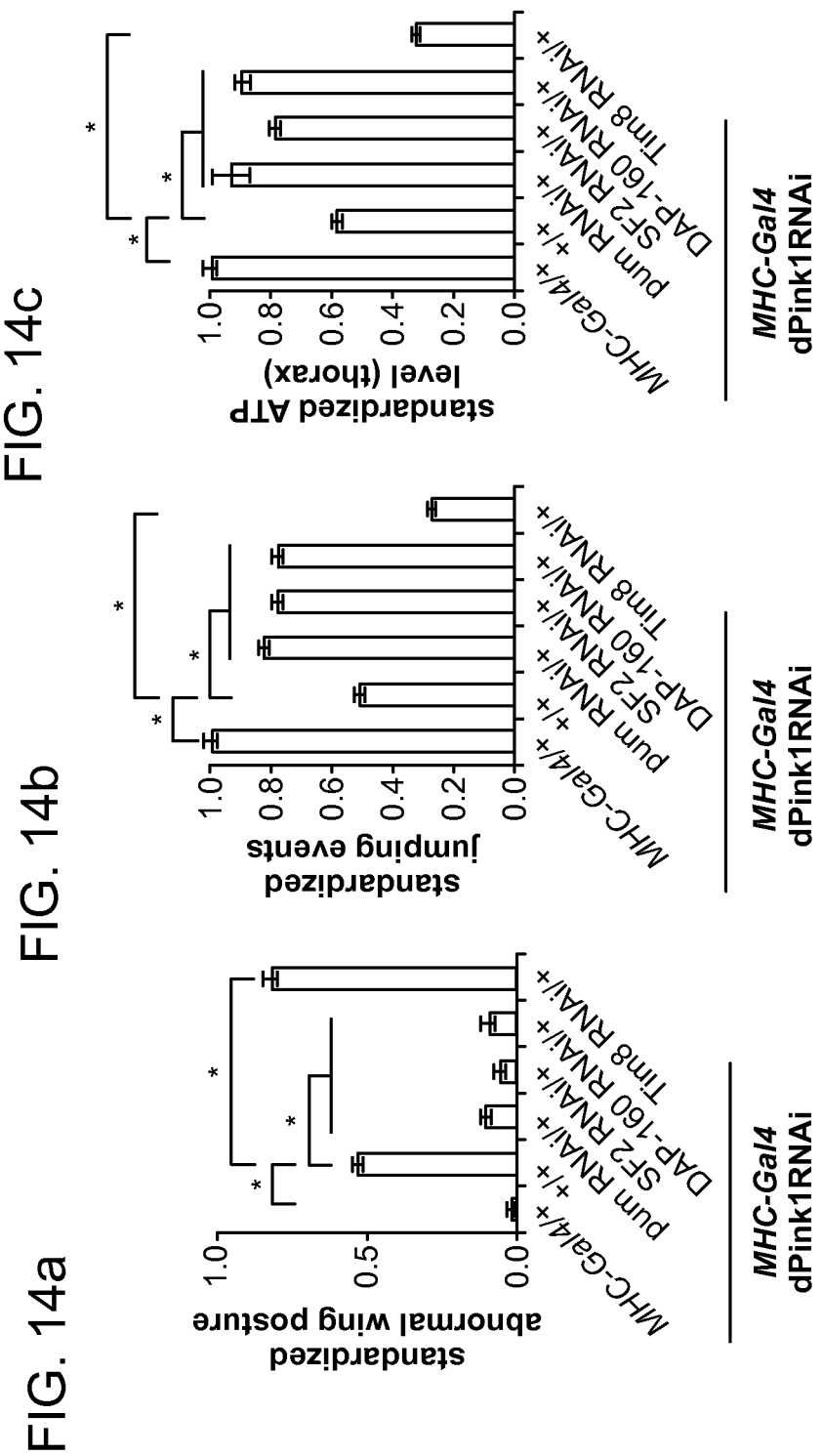
FIG. 14a-14c shows abnormal wing posture (FIG. 14a), jumping ability (FIG. 14b), and thoracic muscle ATP level (FIG. 14c) assays, showing rescue of dPINK1 RNAi phenotypes by RNAi-mediated knockdown of Pum, SF2, or DAP-160, but enhancement by Tim8 RNAi. All data were collected from three independent experiments for each genotype ($P<0.05$).
Figure 15:
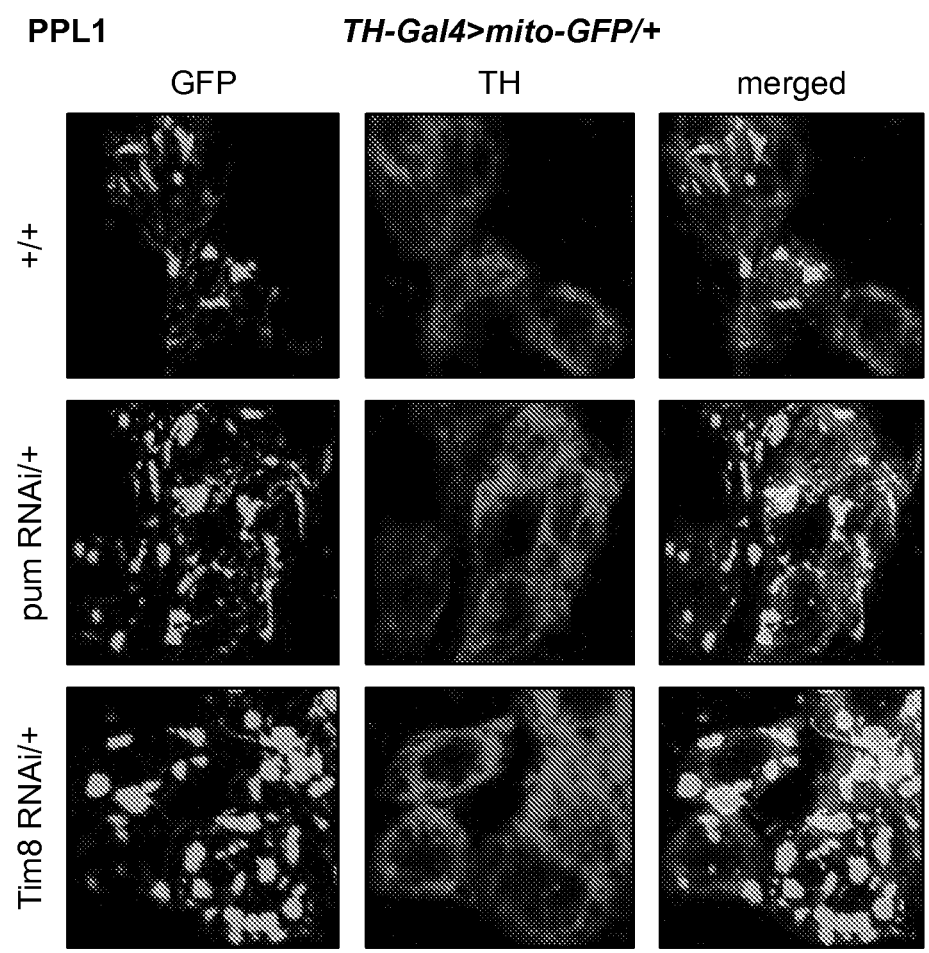
FIG. 15 shows the effects of Pum RNAi and Tim8 RNAi on mitochondrial morphology in DNs within the PPL1 clusters. TH-Gal4-driven Pum RNAi did not alter mitochondria morphology, whereas Tim8 RNAi causes large mitochondrial aggregate formation, similar to that seen in d PINK1$^{B9}$ null mutant DNs. TH-Gal4/+ serves as control. Mitochondria were labelled with mito-GFP. DNs were identified by anti-tyrosine hydroxylase (TH) immunostaining.

At the functional level, Pum and SF2 RNAi effectively rescued the abnormal wing posture, compromised jumping ability, reduced cellular ATP level, and DN loss seen in PINK1$^{B9}$ null mutant and PINK1-RNAi flies (FIG. 13a-d; FIG. 14a-c). In addition, Pum RNAi rescued the abnormal mitochondrial morphologies caused by PINK1 inactivation in thoracic muscles and DNs (FIG. 13e,f). In contrast, RNAi-mediated knockdown of Tim8, a subunit of the TIM complex involved in mitochondrial protein import, had largely opposite effects (FIG. 13a-f, FIG. 14a-c). Moreover, whereas Pum RNAi alone had no effect on mitochondria morphology (FIG. 13e, FIG. 15), TH-Gal4-driven Tim8 RNAi caused mitochondrial aggregation in DNs, phenocopying PINK1$^{B9}$ mutant. These data reinforces the idea that the effects of PINK1 on mitochondria-bound mRNAs may be functionally linked to the co-translational import of the encoded RCC proteins.

Figure 16:
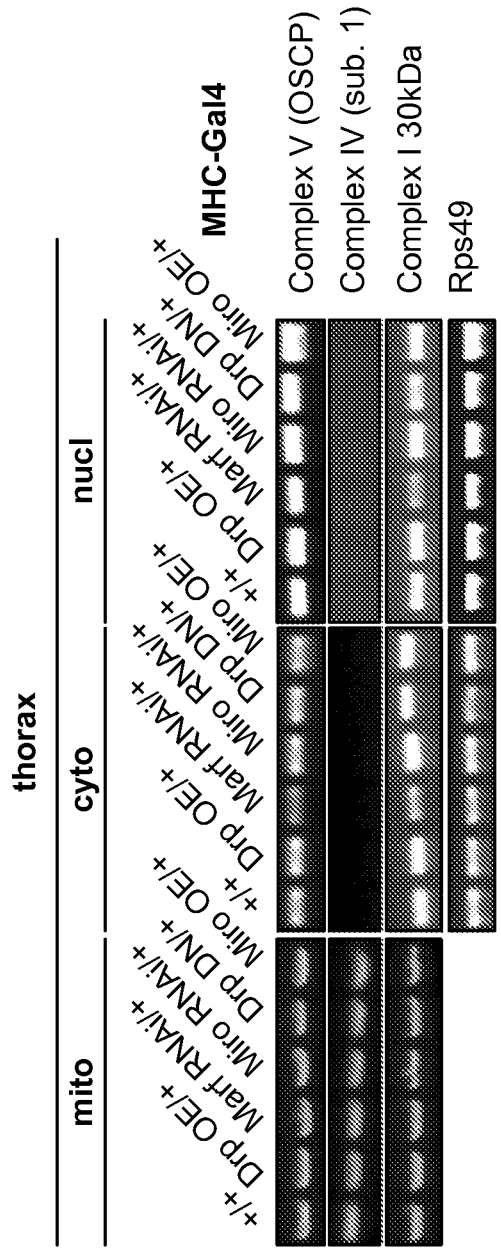
FIG. 16 shows that a lack of effect of altered mitochondria fission and fusion or transport on the mitochondrial recruitment of RCC mRNAs in thoracic muscle tissue. Loss- or gain-of-function of mitochondria fission/fusion (Drp, Marf) and mitochondrial transport (Miro) genes driven by the MHC-Gal4 driver did not alter the mitochondrial recruitment of RCC mRNAs. Complex IV (sub. 1) serves as control for purified mitochondria, and Rps49 for cytoplasmic and nuclear fractions.

PINK1 has been shown to regulate mitochondrial function through fission/fusion dynamics and transport (Yang, Y. et al. Pink1 regulates mitochondria dynamics through interaction with the fission/fusion machinery. *Proc Natl Acad Sci USA* 105, 7070-7075 (2008); Wang, X. et al. PINK1 and Parkin target Miro for phosphorylation and degradation to arrest mitochondria motility. *Cell* 147, 893-906 (2011); Liu, S. et al. Parkinson's disease-associated kinase PINK1 regulates Miro protein level and axonal transport of mitochondria. *PLoS Genet* 8, e1002537 (2012)). It was next tested whether defects in these mitochondrial processes could explain the PINK1 effect on RCC mRNAs. Loss- or gain-of-function of genes involved in mitochondrial fission/fusion or transport had no obvious effects on the mitochondrial recruitment of RCC mRNAs (FIG. 16). Together, these results establish a critical and direct role of PINK1 in regulating the localization and translation of mitochondria-bound RCC mRNAs.

These results reveal a novel and critical role of PINK1 in regulating the localization and translation of mitochondria-bound mRNAs encoding key mitochondrial proteins. Since similar effects were observed in human iDNs and in vivo *Drosophila* PD models, this newly identified function is likely to be fundamental to PINK1 pathogenesis. Given that the overwhelming majority of the mitochondrial proteome is nuclear-encoded and translated outside of mitochondria, tight regulation of the localization and translation of mito-chondria-bound mRNAs could serve a critical role in coordinating the nuclear and mitochondrial genomes during mitochondrial biogenesis, especially during stress conditions. Defects in this process are likely to contribute to the mitochondrial etiology of PD and other major age-related disorders (Wallace, D. C., A mitochondrial paradigm of metabolic and degenerative diseases, aging, and cancer: a dawn for evolutionary medicine. *Annu Rev Genet* 39, 359-407 (2005); Dawson, T. M. & Dawson, V. L. Molecular pathways of neurodegeneration in Parkinson's disease. *Science* 302, 819-822 (2003); Henchcliffe, C. & Beal, M. F. Mitochondrial biology and oxidative stress in Parkinson disease pathogenesis. *Nature Clin Pract Neurol* 4, 600-609 (2008)). These results further indicate that pharmacological agents targeting factors such as Pum will offer therapeutic benefits for PD and other mitochondrial disorders.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. A method of trans-differentiating a terminally differentiated target cell to a neuron comprising the step of introducing: (a) a LIM homeobox transcription factor (Lmx) agent that is LIM homeobox transcription factor, or a nucleic acid encoding the same, (b) a nuclear receptor subfamily 4 (NR4) agent that is a nuclear receptor subfamily 4 factor, or a nucleic acid encoding the same, (c) a c-Fos agent that is a c-Fos, or a nucleic acid encoding the same, and (d) an Early B Cell Factor (EBF) agent that is an EBF, or a nucleic acid encoding the same into the target cell under conditions suitable to cause the target cell to trans-differentiate into a neuron.

2. The method according to claim 1, wherein the Lmx agent is a Lmx1b agent.

3. The method according to claim 1, wherein the nuclear receptor agent is a Nurr1 agent.

4. The method according to claim 1, wherein the EBF agent is an EBF1 agent.

5. The method according to claim 1, wherein the terminally differentiated target cell is a non-neuronal somatic cell.

6. The method according to claim 5, wherein the somatic cell is a human somatic cell.

7. The method according to claim 5, wherein the somatic cell is a fibroblast.

8. The method according to claim 1, wherein the neuron is a dopaminergic neuron.

9. The method according to claim 1, wherein the LIM homeobox transcription factor agent is a nucleic acid encoding LIM homeobox transcription factor, the nuclear receptor subfamily 4 agent is a nucleic acid encoding a nuclear receptor subfamily 4 factor, the c-Fos agent is a nucleic acid encoding a c-Fos and the Early B Cell Factor (EBF) agent is a nucleic acid encoding an EBF.

10. The method according to claim 1, wherein the target cell is from a subject having Parkinson's Disease.

11. The method according to claim 1, wherein the target cell is a fibroblast and the neuron is a dopaminergic neuron.

* * * * *

SEQUENCE LISTING

<160> NUMBER OF SEQ ID NOS: 32

<210> SEQ ID NO 1
<211> LENGTH: 17
<212> TYPE: DNA
<213> ORGANISM: Artificial Sequence
<220> FEATURE:
<223> OTHER INFORMATION: synthetic polynucleotide

<400> SEQUENCE: 1
gagcgtattc ttggagc                                                    17

<210> SEQ ID NO 2
<211> LENGTH: 18
<212> TYPE: DNA
<213> ORGANISM: Artificial sequence -continued

```
<220> FEATURE:
<223> OTHER INFORMATION: synthetic polynucleotide

<400> SEQUENCE: 2
gcatcaacta cacgaccc                                                    18

<210> SEQ ID NO 3
<211> LENGTH: 18
<212> TYPE: DNA
<213> ORGANISM: Artificial sequence
<220> FEATURE:
<223> OTHER INFORMATION: synthetic polynucleotide

<400> SEQUENCE: 3
gatatggcgt ttccccgc                                                    18

<210> SEQ ID NO 4
<211> LENGTH: 19
<212> TYPE: DNA
<213> ORGANISM: Artificial sequence
<220> FEATURE:
<223> OTHER INFORMATION: synthetic polynucleotide

<400> SEQUENCE: 4
gatcagacga agaggggcg                                                   19

<210> SEQ ID NO 5
<211> LENGTH: 19
<212> TYPE: DNA
<213> ORGANISM: Artificial sequence
<220> FEATURE:
<223> OTHER INFORMATION: synthetic polynucleotide

<400> SEQUENCE: 5
ttgctgccgg tgaggcggg                                                   19

<210> SEQ ID NO 6
<211> LENGTH: 18
<212> TYPE: DNA
<213> ORGANISM: Artificial sequence
<220> FEATURE:
<223> OTHER INFORMATION: synthetic polynucleotide

<400> SEQUENCE: 6
cagcagactc aatgggcg                                                    18

<210> SEQ ID NO 7
<211> LENGTH: 19
<212> TYPE: DNA
<213> ORGANISM: Artificial sequence
<220> FEATURE:
<223> OTHER INFORMATION: synthetic polynucleotide

<400> SEQUENCE: 7
tatcagcgaa gtgctggcc                                                   19

<210> SEQ ID NO 8
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 8
caatccagct gtccagctcc                                                  20
```

<210> SEQ ID NO 9
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 9
gcgggaaatc gtgcgtgaca tt                                      22

<210> SEQ ID NO 10
<211> LENGTH: 24
<212> TYPE: DNA
<213> ORGANISM: Artificial sequence
<220> FEATURE:
<223> OTHER INFORMATION: synthetic polynucleotide

<400> SEQUENCE: 10
gatggagttg aaggtagttt cgtg                                    24

<210> SEQ ID NO 11
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 11
taaagaagct ggacaccgtg                                         20

<210> SEQ ID NO 12
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 12
atcaagagca aatccttaag ag                                      22

<210> SEQ ID NO 13
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 13
cctggatttg gaataatttc tc                                      22

<210> SEQ ID NO 14
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 14
tcagaatatc tatgttcagc tg                                      22

<210> SEQ ID NO 15
<211> LENGTH: 19
<212> TYPE: DNA
<213> ORGANISM: Artificial sequence
<220> FEATURE:
<223> OTHER INFORMATION: synthetic polynucleotide

```
<400> SEQUENCE: 15
tggaagccac tcctgtgtg                                         19

<210> SEQ ID NO 16
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 16
cactactgtt ccactactgc                                        20

<210> SEQ ID NO 17
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 17
gaacatgtcg cgctttgttc                                        20

<210> SEQ ID NO 18
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 18
ttgattctgc agcaaacgtt c                                      21

<210> SEQ ID NO 19
<211> LENGTH: 18
<212> TYPE: DNA
<213> ORGANISM: Artificial sequence
<220> FEATURE:
<223> OTHER INFORMATION: synthetic polynucleotide

<400> SEQUENCE: 19
gcaccaagca cttcatcc                                          18

<210> SEQ ID NO 20
<211> LENGTH: 18
<212> TYPE: DNA
<213> ORGANISM: Artificial sequence
<220> FEATURE:
<223> OTHER INFORMATION: synthetic polynucleotide

<400> SEQUENCE: 20
cgatctcgcc gcagtaaa                                          18

<210> SEQ ID NO 21
<211> LENGTH: 18
<212> TYPE: DNA
<213> ORGANISM: Artificial sequence
<220> FEATURE:
<223> OTHER INFORMATION: synthetic polynucleotide

<400> SEQUENCE: 21
tgttcccaag gcgccgac                                          18

<210> SEQ ID NO 22
```

```
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 22
agcctaagaa ggcggataag                                                   20

<210> SEQ ID NO 23
<211> LENGTH: 62
<212> TYPE: DNA
<213> ORGANISM: Artificial sequence
<220> FEATURE:
<223> OTHER INFORMATION: synthetic polynucleotide

<400> SEQUENCE: 23
ggaattccca gaccgctgat gagcctttgg taccaggctc atcagcggtc tgggggaatt       60
cc                                                                      62

<210> SEQ ID NO 24
<211> LENGTH: 62
<212> TYPE: DNA
<213> ORGANISM: Artificial sequence
<220> FEATURE:
<223> OTHER INFORMATION: synthetic polynucleotide

<400> SEQUENCE: 24
ggaattcccc cagaccgctg atgagcctgg taccaaaggc tcatcagcgg tctgggaatt       60
cc                                                                      62

<210> SEQ ID NO 25
<211> LENGTH: 62
<212> TYPE: DNA
<213> ORGANISM: Artificial sequence
<220> FEATURE:
<223> OTHER INFORMATION: synthetic polynucleotide

<400> SEQUENCE: 25
ggaattccca gaaagctctt gagtttttgg taccaaactc aagagctttc tgggggaatt      60
cc                                                                      62

<210> SEQ ID NO 26
<211> LENGTH: 62
<212> TYPE: DNA
<213> ORGANISM: Artificial sequence
<220> FEATURE:
<223> OTHER INFORMATION: synthetic polynucleotide

<400> SEQUENCE: 26
ggaattcccc cagaaagctc ttgagtttgg taccaaaaac tcaagagctt tctgggaatt      60
cc                                                                      62

<210> SEQ ID NO 27
<211> LENGTH: 62
<212> TYPE: DNA
<213> ORGANISM: Artificial sequence
<220> FEATURE:
<223> OTHER INFORMATION: synthetic polynucleotide

<400> SEQUENCE: 27
ggaattcgga gattgctgga catatattgg tacctatatg tccagcaatc tccgggaatt      60
cc                                                                      62
```

```
<210> SEQ ID NO 28
<211> LENGTH: 62
<212> TYPE: DNA
<213> ORGANISM: Artificial sequence
<220> FEATURE:
<223> OTHER INFORMATION: synthetic polynucleotide

<400> SEQUENCE: 28
ggaattcccg gagattgctg gacatatagg taccaatata tgtccagcaa tctccgaatt      60
cc                                                                    62

<210> SEQ ID NO 29
<211> LENGTH: 21
<212> TYPE: RNA
<213> ORGANISM: Artificial sequence
<220> FEATURE:
<223> OTHER INFORMATION: synthetic polynucleotide

<400> SEQUENCE: 29
ccagaaagcu cuugaguuuu u                                               21

<210> SEQ ID NO 30
<211> LENGTH: 21
<212> TYPE: RNA
<213> ORGANISM: Artificial sequence
<220> FEATURE:
<223> OTHER INFORMATION: synthetic polynucleotide

<400> SEQUENCE: 30
aaacucaaga gcuuucuggc g                                               21

<210> SEQ ID NO 31
<211> LENGTH: 21
<212> TYPE: RNA
<213> ORGANISM: Artificial sequence
<220> FEATURE:
<223> OTHER INFORMATION: synthetic polynucleotide

<400> SEQUENCE: 31
ccagccuccg uuucaccggu u                                               21

<210> SEQ ID NO 32
<211> LENGTH: 20
<212> TYPE: RNA
<213> ORGANISM: Artificial sequence
<220> FEATURE:
<223> OTHER INFORMATION: synthetic polynucleotide

<400> SEQUENCE: 32
aaccggugaa acggaggcug                                                 20
```